(12) United States Patent
Tyler et al.

(10) Patent No.: US 10,537,703 B2
(45) Date of Patent: Jan. 21, 2020

(54) SYSTEMS AND METHODS FOR TRANSDERMAL ELECTRICAL STIMULATION TO IMPROVE SLEEP

(71) Applicant: Thync Global, Inc., Los Gatos, CA (US)

(72) Inventors: William J. Tyler, Cave Creek, AZ (US); Alyssa M. Boasso, Brookline, MA (US); Hailey M. Mortimore, Boston, MA (US); Sumon K. Pal, Boston, MA (US); Jonathan Charlesworth, Menlo Park, CA (US)

(73) Assignee: Thync Global, Inc., Los Gatos, CA (US)

( * ) Notice: Subject to any disclaimer, the term of this patent is extended or adjusted under 35 U.S.C. 154(b) by 0 days.

(21) Appl. No.: 15/460,138

(22) Filed: Mar. 15, 2017

(65) Prior Publication Data

US 2017/0182285 A1 Jun. 29, 2017

Related U.S. Application Data

(63) Continuation-in-part of application No. PCT/US2016/012128, filed on Jan. 5, 2016, and a
(Continued)

(51) Int. Cl.
*A61M 21/02* (2006.01)
*A61N 1/36* (2006.01)
(Continued)

(52) U.S. Cl.
CPC ........... *A61M 21/02* (2013.01); *A61N 1/0456* (2013.01); *A61N 1/36025* (2013.01);
(Continued)

(58) Field of Classification Search
CPC ............... A61N 1/0456; A61M 21/00; A61M 2021/055; A61M 21/02
See application file for complete search history.

(56) References Cited

U.S. PATENT DOCUMENTS 3,255,753 A   6/1966 Wing
3,388,699 A * 6/1968 Webb .................. A61N 1/0408
                                                600/26
(Continued)

FOREIGN PATENT DOCUMENTS

CN       1204268 A   1/1999
CN       1607970 A   4/2005
(Continued)

OTHER PUBLICATIONS

Aston-Jones et al.; An integrative theory of locus coeruleus-norepinephrine function: adaptive gain and optimal performance; Annu. Rev. Neurosci.; 28: pp. 403-450; Jul. 21, 2005.
(Continued)

*Primary Examiner* — Carrie R Dorna
(74) *Attorney, Agent, or Firm* — Shay Glenn LLP

(57) ABSTRACT

Methods and apparatuses for improving sleep by transdermal electrical stimulation (TES). In general, described herein are methods for applying TES to a subject, and particularly the subject's head (e.g., temple/forehead region) and/or neck with an TES waveform adapted to improve sleep, including reducing sleep onset (falling to sleep) more quickly and/or lengthening the duration of sleep. TES waveform(s) particularly well suited to enhancing sleep are also described herein.

32 Claims, 31 Drawing Sheets

Related U.S. Application Data continuation-in-part of application No. 15/264,224, filed on Sep. 13, 2016, which is a continuation-in-part of application No. 14/558,604, filed on Dec. 2, 2014, now Pat. No. 9,440,070, which is a continuation-in-part of application No. 14/091,121, filed on Nov. 26, 2013, now Pat. No. 8,903,494, said application No. 15/264,224 is a continuation-in-part of application No. 15/170,878, filed on Jun. 1, 2016, and a continuation-in-part of application No. 14/715,470, filed on May 18, 2015, now Pat. No. 9,474,891, said application No. 15/264,224 is a continuation-in-part of application No. 14/715,476, filed on May 18, 2015, now Pat. No. 9,517,351, and a continuation-in-part of application No. 15/169,445, filed on May 31, 2016.

(60) Provisional application No. 62/308,845, filed on Mar. 15, 2016, provisional application No. 62/268,084, filed on Dec. 16, 2015, provisional application No. 62/213,949, filed on Sep. 3, 2015, provisional application No. 62/200,256, filed on Aug. 3, 2015, provisional application No. 62/190,211, filed on Jul. 8, 2015, provisional application No. 62/170,111, filed on Jun. 2, 2015, provisional application No. 62/169,522, filed on Jun. 1, 2015, provisional application No. 62/169,523, filed on Jun. 1, 2015, provisional application No. 62/168,615, filed on May 29, 2015, provisional application No. 62/100,004, filed on Jan. 5, 2015, provisional application No. 62/100,022, filed on Jan. 5, 2015, provisional application No. 62/099,950, filed on Jan. 5, 2015, provisional application No. 62/100,029, filed on Jan. 5, 2015, provisional application No. 62/099,960, filed on Jan. 5, 2015, provisional application No. 62/076,459, filed on Nov. 6, 2014, provisional application No. 62/075,896, filed on Nov. 6, 2014, provisional application No. 62/076,459, filed on Nov. 6, 2014, provisional application No. 62/002,910, filed on May 25, 2014, provisional application No. 61/994,860, filed on May 17, 2014, provisional application No. 61/907,394, filed on Nov. 22, 2013, provisional application No. 61/900,880, filed on Nov. 6, 2013, provisional application No. 61/888,910, filed on Oct. 9, 2013, provisional application No. 61/875,891, filed on Sep. 10, 2013, provisional application No. 61/875,424, filed on Sep. 9, 2013, provisional application No. 61/845,845, filed on Jul. 12, 2013, provisional application No. 61/841,308, filed on Jun. 29, 2013, provisional application No. 61/770,479, filed on Feb. 28, 2013, provisional application No. 61/767,945, filed on Feb. 22, 2013, provisional application No. 61/765,795, filed on Feb. 17, 2013, provisional application No. 61/729,851, filed on Nov. 26, 2012.

(51) Int. Cl.
*A61N 1/04* (2006.01)
*A61M 21/00* (2006.01)

(52) U.S. Cl.
CPC . *A61M 2021/0072* (2013.01); *A61M 2230/06* (2013.01); *A61M 2230/42* (2013.01); *A61M 2230/63* (2013.01)

(56) References Cited

U.S. PATENT DOCUMENTS

| | | |
|---|---|---|
| 3,620,219 A | 11/1971 | Barker |
| 3,648,708 A | 3/1972 | Haeri |
| 3,762,396 A * | 10/1973 | Ballentine .............. A61M 21/02 600/26 |
| 4,418,687 A | 12/1983 | Matsumoto et al. |
| 4,431,000 A | 2/1984 | Butler et al. |
| 4,646,744 A | 3/1987 | Capel |
| 4,664,117 A | 5/1987 | Beck |
| 4,865,048 A | 9/1989 | Eckerson |
| 5,144,952 A | 9/1992 | Frachet et al. |
| 5,183,041 A | 2/1993 | Toriu et al. |
| 5,335,657 A | 8/1994 | Terry et al. |
| 5,342,410 A | 8/1994 | Braverman |
| 5,397,338 A | 3/1995 | Grey et al. |
| 5,476,481 A | 12/1995 | Schondorf |
| 5,487,759 A | 1/1996 | Bastyr et al. |
| 5,514,175 A | 5/1996 | Kim et al. |
| 5,540,736 A | 7/1996 | Haimovich et al. |
| 5,573,552 A | 11/1996 | Hansjurgens |
| 5,578,065 A | 11/1996 | Hattori et al. |
| 5,593,427 A | 1/1997 | Gliner et al. |
| 5,738,647 A | 4/1998 | Bernhard et al. |
| 5,792,067 A | 8/1998 | Karell |
| 6,066,163 A | 5/2000 | John |
| 6,280,454 B1 | 8/2001 | Wang |
| 6,324,432 B1 | 11/2001 | Rigaux et al. |
| 6,445,955 B1 | 9/2002 | Michelson et al. |
| 6,463,328 B1 | 10/2002 | John |
| 6,516,227 B1 | 2/2003 | Meadows et al. |
| 6,526,318 B1 | 2/2003 | Ansarinia |
| 6,567,702 B1 | 5/2003 | Nekhendzy et al. |
| 6,731,987 B1 | 5/2004 | McAdams et al. |
| 6,983,184 B2 | 1/2006 | Price |
| 7,120,499 B2 | 10/2006 | Thrope et al. |
| 7,146,217 B2 | 12/2006 | Firlik et al. |
| 7,263,501 B2 | 8/2007 | Tirinato et al. |
| 7,376,467 B2 | 5/2008 | Thrope et al. |
| 7,422,555 B2 | 9/2008 | Zabara |
| 7,577,481 B2 | 8/2009 | Firlik et al. |
| 7,660,636 B2 | 2/2010 | Castel et al. |
| 7,801,600 B1 | 9/2010 | Carbunaru et al. |
| 7,891,615 B2 | 2/2011 | Bevirt |
| 7,949,403 B2 | 5/2011 | Palermo et al. |
| 8,029,431 B2 | 10/2011 | Tononi |
| 8,034,294 B1 | 10/2011 | Goldberg |
| 8,086,318 B2 | 12/2011 | Strother et al. |
| 8,097,926 B2 | 1/2012 | De Graff et al. |
| 8,116,875 B2 | 2/2012 | Osypka et al. |
| 8,121,695 B2 | 2/2012 | Gliner et al. |
| 8,150,537 B2 | 4/2012 | Tanaka et al. |
| 8,190,248 B2 | 5/2012 | Besio et al. |
| 8,197,276 B2 | 6/2012 | Egloff et al. |
| 8,204,601 B2 | 6/2012 | Moyer et al. |
| 8,239,030 B1 | 8/2012 | Hagedorn et al. |
| 8,265,761 B2 | 9/2012 | Siever |
| 8,280,502 B2 | 10/2012 | Hargrove et al. |
| 8,346,337 B2 | 1/2013 | Heller et al. |
| 8,380,315 B2 | 2/2013 | DeGiorgio et al. |
| 8,428,738 B2 | 4/2013 | Valencia |
| 8,463,383 B2 | 6/2013 | Sakai et al. |
| 8,494,625 B2 | 7/2013 | Hargrove |
| 8,494,627 B2 | 7/2013 | Bikson et al. |
| 8,506,469 B2 | 8/2013 | Dietrich et al. |
| 8,532,758 B2 | 9/2013 | Silverstone |
| 8,560,075 B2 | 10/2013 | Covalin |
| 8,571,651 B2 | 10/2013 | Ben-Ezra et al. |
| 8,583,238 B1 * | 11/2013 | Heldman .............. A61N 1/0492 607/45 |
| 8,583,256 B2 | 11/2013 | Tracey et al. |
| 8,612,005 B2 | 12/2013 | Rezai et al. |
| 8,639,343 B2 | 1/2014 | De Vos |
| 8,660,644 B2 | 2/2014 | Jaax et al. |
| 8,688,239 B2 | 4/2014 | Hartlep et al. |
| 8,843,210 B2 | 9/2014 | Simon et al. |
| 8,874,219 B2 | 10/2014 | Trier et al. |

(56) References Cited

U.S. PATENT DOCUMENTS

| | | |
|---|---|---|
| 8,903,494 B2 | 12/2014 | Goldwasser et al. |
| 8,983,621 B2 | 3/2015 | Hou et al. |
| 9,002,458 B2 | 4/2015 | Pal et al. |
| 9,014,811 B2 | 4/2015 | Pal et al. |
| 9,067,054 B2 | 6/2015 | Simon et al. |
| 9,168,374 B2 | 10/2015 | Su |
| 9,205,258 B2 | 12/2015 | Simon et al. |
| 9,233,244 B2 | 1/2016 | Pal et al. |
| 9,248,292 B2 | 2/2016 | Trier et al. |
| 9,333,334 B2 | 5/2016 | Jeffery et al. |
| 9,364,674 B2 | 6/2016 | Cook et al. |
| 9,393,401 B2 | 7/2016 | Goldwasser et al. |
| 9,393,430 B2 | 7/2016 | Demers et al. |
| 9,399,126 B2 | 7/2016 | Pal et al. |
| 9,415,219 B2 | 8/2016 | Simon et al. |
| 9,440,070 B2 | 9/2016 | Goldwasser et al. |
| 9,446,242 B2 | 9/2016 | Griffith |
| 9,474,891 B2 | 10/2016 | Demers et al. |
| 9,474,905 B2 | 10/2016 | Doan et al. |
| 9,517,351 B2 | 12/2016 | Charlesworth et al. |
| 9,655,772 B2 | 5/2017 | Smith et al. |
| 9,656,076 B2 | 5/2017 | Trier et al. |
| 9,700,725 B2 | 7/2017 | Zhu |
| 9,731,116 B2 | 8/2017 | Chen |
| 9,744,347 B2 | 8/2017 | Chen et al. |
| 9,764,133 B2 | 9/2017 | Thomas et al. |
| 9,782,587 B2 | 10/2017 | Trier et al. |
| 2001/0000187 A1 | 4/2001 | Peckham et al. |
| 2002/0116036 A1 | 8/2002 | Daignault et al. |
| 2003/0088279 A1 | 5/2003 | Rissmann et al. |
| 2003/0134545 A1 | 7/2003 | McAdams et al. |
| 2003/0171685 A1 | 9/2003 | Lesser et al. |
| 2003/0225323 A1 | 12/2003 | Kiani et al. |
| 2004/0019370 A1 | 1/2004 | Gliner et al. |
| 2004/0098065 A1 | 5/2004 | Hagglof et al. |
| 2004/0158305 A1 | 8/2004 | Axelgaard |
| 2004/0267333 A1 | 12/2004 | Kronberg |
| 2005/0165460 A1 | 7/2005 | Erfan |
| 2005/0267388 A1 | 12/2005 | Hanna |
| 2005/0283259 A1 | 12/2005 | Wolpow |
| 2006/0047215 A1 | 3/2006 | Newman et al. |
| 2006/0064139 A1 | 3/2006 | Chung et al. |
| 2006/0149119 A1 | 7/2006 | Wang |
| 2006/0190057 A1 | 8/2006 | Reese |
| 2006/0195159 A1 | 8/2006 | Bradley et al. |
| 2006/0206163 A1 | 9/2006 | Wahlstrand et al. |
| 2006/0247985 A1 | 11/2006 | Liamos et al. |
| 2007/0053466 A1 | 3/2007 | Klostermann |
| 2007/0088419 A1 | 4/2007 | Fiorina et al. |
| 2007/0097593 A1 | 5/2007 | Armstrong |
| 2007/0100275 A1 | 5/2007 | Fischer et al. |
| 2007/0173890 A1 | 7/2007 | Armstrong |
| 2007/0213790 A1 | 9/2007 | Nolan et al. |
| 2007/0276451 A1 | 11/2007 | Rigaux |
| 2008/0015641 A1 | 1/2008 | Armstrong et al. |
| 2008/0045882 A1 | 2/2008 | Finsterwald |
| 2008/0071626 A1 | 3/2008 | Hill |
| 2008/0097564 A1 | 4/2008 | Lathrop |
| 2008/0132974 A1 | 6/2008 | Strother et al. |
| 2008/0207985 A1* | 8/2008 | Farone ............... A61N 1/36021 600/15 |
| 2008/0208266 A1 | 8/2008 | Lesser et al. |
| 2008/0215113 A1 | 9/2008 | Pawlowicz |
| 2008/0275293 A1 | 11/2008 | Lattner et al. |
| 2008/0281368 A1 | 11/2008 | Bulkes et al. |
| 2008/0319505 A1 | 12/2008 | Boyden et al. |
| 2009/0048642 A1 | 2/2009 | Goroszeniuk |
| 2009/0054952 A1 | 2/2009 | Glukhovsky et al. |
| 2009/0082831 A1* | 3/2009 | Paul ................... A61N 1/0456 607/59 |
| 2009/0099623 A1 | 4/2009 | Bentwich |
| 2009/0112280 A1 | 4/2009 | Wingeier et al. |
| 2009/0177243 A1 | 7/2009 | Lebedev et al. |
| 2009/0210028 A1 | 8/2009 | Rigaux et al. |
| 2009/0240303 A1 | 9/2009 | Wahlstrand et al. |
| 2009/0270947 A1 | 10/2009 | Stone et al. |
| 2009/0287108 A1 | 11/2009 | Levy |
| 2010/0057154 A1 | 3/2010 | Dietrich et al. |
| 2010/0076533 A1 | 3/2010 | Dar et al. |
| 2010/0094375 A1 | 4/2010 | Donders et al. |
| 2010/0145399 A1 | 6/2010 | Johari et al. |
| 2010/0152817 A1 | 6/2010 | Gillbe |
| 2010/0256436 A1 | 10/2010 | Partsch et al. |
| 2010/0318168 A1 | 12/2010 | Bignetti |
| 2011/0029045 A1 | 2/2011 | Cevette et al. |
| 2011/0034756 A1* | 2/2011 | Hacking ............... A61M 21/02 600/26 |
| 2011/0077660 A1 | 3/2011 | Janik et al. |
| 2011/0082326 A1 | 4/2011 | Mishelevich et al. |
| 2011/0082515 A1 | 4/2011 | Libbus et al. |
| 2011/0093033 A1 | 4/2011 | Nekhendzy |
| 2011/0112394 A1 | 5/2011 | Mishelevich |
| 2011/0112590 A1 | 5/2011 | Wu et al. |
| 2011/0114191 A1 | 5/2011 | Wheater et al. |
| 2011/0137381 A1 | 6/2011 | Lee et al. |
| 2011/0144716 A1 | 6/2011 | Bikson et al. |
| 2011/0160811 A1 | 6/2011 | Walker |
| 2011/0172752 A1 | 7/2011 | Bingham et al. |
| 2011/0190846 A1 | 8/2011 | Ruffini et al. |
| 2011/0230701 A1 | 9/2011 | Simon et al. |
| 2011/0230702 A1 | 9/2011 | Honour |
| 2011/0230938 A1 | 9/2011 | Simon et al. |
| 2011/0270345 A1 | 11/2011 | Johnston et al. |
| 2011/0276112 A1 | 11/2011 | Simon et al. |
| 2011/0288610 A1 | 11/2011 | Brocke |
| 2011/0301683 A1 | 12/2011 | Axelgaard |
| 2011/0307029 A1* | 12/2011 | Hargrove ............... A61N 2/008 607/45 |
| 2011/0319950 A1 | 12/2011 | Sullivan |
| 2012/0016431 A1 | 1/2012 | Paul et al. |
| 2012/0029591 A1 | 2/2012 | Simon et al. |
| 2012/0029601 A1 | 2/2012 | Simon et al. |
| 2012/0109251 A1 | 5/2012 | Lebedev et al. |
| 2012/0149973 A1 | 6/2012 | Holloway |
| 2012/0165759 A1 | 6/2012 | Rogers et al. |
| 2012/0182924 A1 | 7/2012 | Gaines et al. |
| 2012/0184801 A1* | 7/2012 | Simon ................... A61N 2/006 600/14 |
| 2012/0185020 A1 | 7/2012 | Simon et al. |
| 2012/0209340 A1 | 8/2012 | Escribano |
| 2012/0209346 A1 | 8/2012 | Bikson et al. |
| 2012/0245409 A1 | 9/2012 | Liang |
| 2012/0245653 A1 | 9/2012 | Bikson et al. |
| 2012/0296390 A1 | 11/2012 | Nakashima et al. |
| 2012/0302912 A1 | 11/2012 | Moffitt et al. |
| 2012/0306628 A1 | 12/2012 | Singhal |
| 2013/0035734 A1 | 2/2013 | Soler et al. |
| 2013/0041235 A1 | 2/2013 | Rogers et al. |
| 2013/0060304 A1 | 3/2013 | La Tendresse et al. |
| 2013/0066395 A1 | 3/2013 | Simon et al. |
| 2013/0079659 A1 | 3/2013 | Akhadov et al. |
| 2013/0096641 A1 | 4/2013 | Strother et al. |
| 2013/0131551 A1 | 5/2013 | Raghunathan et al. |
| 2013/0158627 A1 | 6/2013 | Gozani et al. |
| 2013/0184779 A1 | 7/2013 | Bikson et al. |
| 2013/0204315 A1 | 8/2013 | Wongsarnpigoon et al. |
| 2013/0226275 A1 | 8/2013 | Duncan |
| 2013/0253613 A1 | 9/2013 | Salahovic et al. |
| 2013/0267761 A1 | 10/2013 | Bentwich |
| 2013/0282095 A1 | 10/2013 | Mignolet et al. |
| 2013/0304175 A1 | 11/2013 | Voegele et al. |
| 2013/0318168 A1 | 11/2013 | Demain et al. |
| 2013/0325096 A1 | 12/2013 | Dupelle et al. |
| 2013/0333094 A1 | 12/2013 | Rogers et al. |
| 2014/0031895 A1 | 1/2014 | Rahimi et al. |
| 2014/0128939 A1 | 5/2014 | Embrey et al. |
| 2014/0128944 A1 | 5/2014 | Stern et al. |
| 2014/0163645 A1 | 6/2014 | Dinsmoor et al. |
| 2014/0182350 A1 | 7/2014 | Bhavaraju et al. |
| 2014/0186807 A1 | 7/2014 | Rastatter et al. |
| 2014/0222102 A1 | 8/2014 | Lemus et al. |
| 2014/0257449 A1 | 9/2014 | Helmer |
| 2014/0275933 A1 | 9/2014 | Meyer et al. |
| 2014/0277324 A1 | 9/2014 | DiUbaldi et al. |

(56) References Cited

U.S. PATENT DOCUMENTS

| | | |
|---|---|---|
| 2014/0309709 A1 | 10/2014 | Gozani et al. |
| 2014/0336728 A1 | 11/2014 | Franke et al. |
| 2014/0371814 A1 | 12/2014 | Spizzirri et al. |
| 2015/0066104 A1 | 3/2015 | Wingeier et al. |
| 2015/0224310 A1 | 8/2015 | Sharma et al. |
| 2015/0230863 A1 | 8/2015 | Youngquist et al. |
| 2015/0257970 A1 | 9/2015 | Mucke et al. |
| 2015/0335877 A1 | 11/2015 | Jeffery et al. |
| 2016/0008632 A1 | 1/2016 | Wetmore et al. |
| 2016/0074657 A1 | 3/2016 | Kwan et al. |
| 2016/0279435 A1 | 9/2016 | Hyde et al. |
| 2016/0317809 A1 | 11/2016 | Pal et al. |
| 2016/0346530 A1 | 12/2016 | Jeffery et al. |
| 2016/0346545 A1 | 12/2016 | Pal et al. |
| 2017/0076414 A1 | 3/2017 | Egnal et al. |
| 2017/0252562 A1 | 9/2017 | Goldwasser et al. |
| 2018/0036533 A1 | 2/2018 | Yoo et al. |
| 2018/0272118 A1 | 9/2018 | Goldwasser et al. |

FOREIGN PATENT DOCUMENTS

| | | |
|---|---|---|
| CN | 1704131 A | 12/2005 |
| CN | 1842356 A | 10/2006 |
| CN | 101234233 A | 8/2008 |
| CN | 101244314 A | 8/2008 |
| CN | 201353374 Y | 12/2009 |
| CN | 102245253 A | 11/2011 |
| CN | 102725021 A | 10/2012 |
| CN | 102906752 A | 1/2013 |
| CN | 103517732 A | 1/2014 |
| EP | 502919 B1 | 11/1993 |
| EP | 801957 A1 | 10/1997 |
| EP | 09965358 A2 | 12/1999 |
| EP | 1529550 A1 | 5/2005 |
| EP | 1502623 B1 | 11/2007 |
| EP | 1551290 B1 | 8/2008 |
| EP | 2024018 A2 | 2/2009 |
| EP | 2314346 A1 | 4/2011 |
| EP | 1559369 B1 | 3/2012 |
| EP | 2069001 B1 | 2/2013 |
| JP | 49061984 A | 6/1974 |
| JP | 05031197 A | 2/1993 |
| JP | 10108913 A | 4/1998 |
| JP | 2001129100 A | 5/2001 |
| JP | 2001293097 A | 10/2001 |
| JP | 2002306604 A | 10/2002 |
| JP | 200310230 A | 1/2003 |
| JP | 2006192302 A | 7/2006 |
| JP | 3129187 U | 1/2007 |
| JP | 200985901 A | 4/2009 |
| JP | 2011118293 A | 6/2011 |
| WO | WO92/06737 A1 | 4/1992 |
| WO | WO93/17628 A1 | 9/1993 |
| WO | WO94/00188 A1 | 1/1994 |
| WO | WO94/00189 A1 | 1/1994 |
| WO | WO01/08071 A1 | 2/2001 |
| WO | WO01/78834 A1 | 10/2001 |
| WO | WO03/105945 A2 | 12/2003 |
| WO | WO2005/110531 A1 | 11/2005 |
| WO | WO2006/113801 A2 | 10/2006 |
| WO | WO2006/138702 A2 | 12/2006 |
| WO | WO2008/155114 A1 | 12/2008 |
| WO | WO2009/089014 A1 | 7/2009 |
| WO | WO2009/137683 A2 | 11/2009 |
| WO | WO2009/147599 A1 | 12/2009 |
| WO | WO2010/047834 A1 | 4/2010 |
| WO | WO2010/067145 A1 | 6/2010 |
| WO | WO2010/120823 A2 | 10/2010 |
| WO | WO2011/044176 A1 | 4/2011 |
| WO | WO2011/147546 A1 | 12/2011 |
| WO | WO2012/082960 A2 | 6/2012 |
| WO | WO2012/089588 A1 | 7/2012 |
| WO | WO2012/116407 A1 | 9/2012 |
| WO | WO2012/129574 A2 | 9/2012 |
| WO | WO2012/150600 A2 | 11/2012 |
| WO | WO2012/156051 A1 | 11/2012 |
| WO | WO2012/156052 A2 | 11/2012 |
| WO | WO2013/071307 A1 | 5/2013 |
| WO | WO2013/192582 A1 | 12/2013 |
| WO | WO2014/107624 A1 | 7/2014 |
| WO | WO2014/195516 A1 | 12/2014 |
| WO | WO2015/036420 A1 | 3/2015 |
| WO | WO2015/061663 A1 | 4/2015 |
| WO | WO2015/143053 A1 | 9/2015 |
| WO | WO2017/201525 A1 | 11/2017 |

OTHER PUBLICATIONS

Aston-Jones et al.; Role of locus coeruleus in attention and behavioral flexibility; Biological Psychiatry; 46(9); pp. 1309-1320; Nov. 1, 1999.

Axelgaard Manufacturing Co. Ltd.; Little PALS® (product information); 2 pgs.; printed Feb. 11, 2013 from http://wvvw.axelgaard.com/prod_little-pals.html.

Axelgaard Manufacturing Co. Ltd.; PALS® Platinum Blue (product information); 2 pgs.; printed Feb. 11, 2013 from http://www.axelgaard.com/prod_pals-platinum-blue.html.

Backhaus et al.; Sleep disturbances are correlated with decreased morning awakening salivary cortisol; Psychoneuroendocrinology; 29(9): pp. 1184-1191; Oct. 31, 2004.

Basta et al.; Chronic Insomnia and the Stress System; Sleep Medicine Clinics; 2(2): pp. 279-291; (Author Manuscript, 20 pages); Jun. 30, 2007.

Berlad et al.; Power spectrum analysis and heart rate variability in Stage 4 and REM sleep: evidence for state-specific changes in autonomic dominance; Journal of Sleep Research; 2(2): pp. 88-90; Jun. 1, 1993.

Berridge et al.; The locus coeruleus-noradrenergic system: modulation of behavioral state and state-dependent cognitive processes; Brain Research Reviews; 42(1); pp. 33-84; Apr. 30, 2003.

Brown et al.; Control of sleep and wakefulness; Physiological reviews; 92(3); pp. 1087-1187; Jul. 1, 2012.

Brown et al.;Locus ceruleus activation suppresses feedforward interneurons and reduces beta-gamma electroencephalogram frequencies while it enhances theta frequencies in rat dentate gyrus; Journals of Neuroscience; 25(8): pp. 1985-1991; Feb. 23, 2005.

Buchanan et al.; Salivary alpha-amylase levels as a biomarker of experienced fear; Communicative and Integrative Biology; 3(6); pp. 525-527; Nov. 1, 2010.

Buckley et al.; On the Interactions of the Hypothalamic-Pituitary-Adrenal (HPA) Axis and Sleep: Normal HPA Axis Activity and Circadian Rhythm, Exemplary Sleep Disorders; The Journal of Clinical Endocrinology and Metabolism; 90(5); pp. 3106-3114; May 1, 2005.

Buysse et al.; The Pittsburgh Sleep Quality Index: a new instrument for psychiatric practice and research; Psychiatric Research; 28(2); pp. 193-213; May 31, 1989.

Carter et al.; Tuning arousal with optogenetic modulation of locus coeruleus neurons; Nature Neuroscience; 13(12); pp. 1526-1533; Dec. 1, 2010.

Chaieb et al.; Transcranial alternating current stimulation in the low kHz range increases motor cortex excitability; Restor Neurol Neurosci; 29(3); pp. 167-175; Mar. 2011.

Cook et al.; Trigeminal nerve stimulation in major depressive disorder: acute outcomes in an open pilot study; Epilepsy and Behavior; 28(2): pp. 221-226; Aug. 31, 2013.

Coutinho et al.; Musical emotions: predicting second-by-second subjective feelings of emotion from low-level psychoacoustic features and physiological measurements; Emotion; 11(4); pp. 921-937; Aug. 2011.

DaSilva et al.; Electrode positioning and montage in transcranial direct current stimulation; J Vis Exp; 51; e2744; 11 pgs.; May 2011.

Degiorgio et al., Trigeminal nerve stimulation for epilepsy: long-term feasibility and efficacy; Neurology; 72(10): pp. 936-938; Mar. 10, 2009.

Degiorgio et al.; Randomized controlled trial of trigeminal nerve stimulation for drug-resistant epilepsy; Neurology; 80(9); pp. 786-791; Feb. 26, 2013.

(56) References Cited

OTHER PUBLICATIONS

Digitimer LTD.; DS2 and DS3 Isolated Stimulator (product information); 2 pgs.; downloaded from http://www.digitimer.com/research/stimulators/index.htm on Feb. 10, 2014.
Elder et al.; The cortisol awakening response—applications and implications for sleep medicine; Sleep Medicine Reviews; 18(3): pp. 215-224; Jun. 30, 2014.
Electozyme; Company and Product Information; 3 pgs.; printed Feb. 11, 2014 from http://electrozyme.com/applications/.
Eschenko et al.; Noradrenergic neurons of the locus coeruleus are phase locked to cortical up-down states during sleep; Cerebral Cortex; 22(2); pp. 426-435; Feb. 1, 2012.
Feurra et al.; Frequency specific modulation of human somatosensory cortex; Front Psychol; 2(13); 6 pgs.; Feb. 2011.
Franowicz et al.; Treatment with the noradrenergic alpha-2 agonist clonidine, but not diazepam, improves spatial working memory in normal young rhesus monkeys; Neuropsychopharmacology; 21(5); pp. 611-621; Nov. 1, 1999.
Garraway et al.; Modulatory actions of serotonin, norepinephrine, dopamine, and acetylcholine in spinal cord deep dorsal horn neurons; Journal of Neurophysiology; 86(5); pp. 2183-2194; Nov. 1, 2001.
GoFlow; tDCS Kit; product information; 9 pgs..; printed Feb. 10, 2014 (http://flowstateengaged.com/).
Golestanirad et al; Analysis of fractal electrodes for efficient neural stimulation; Frontiers in Neurengineering; 6(3); 10 pages; Jul. 2013.
Gracenote; Timeline-metadata-api; 3 pages; retrieved from the internet Jul. 7, 2015; (https://github.com/gracenote/timeline-metadata-api/blob/master/README.md).
Granger et al.; Salivary alpha-amylase in biobehavioral research: recent developments and applications; Annals of the New York Academy of Sciences; 1098(1); pp. 122-144; Mar. 1, 2007.
Grindhouse Wetware; Thinking Cap; product information; 1 pg.; printed Feb. 10, 2014 (http://www.grindhousewetware.com/thinkingcap.html).
Gummadavelli et al.; Neurostimulation to improve level of consciousness in patients with epilepsy. Neurosurgical Focus; 38(6); pp. E10; (manuscript version,14 pages); Jun. 2015.
Hajos et al.; Norepinephrine but not serotonin reuptake inhibitors enhance theta and gamma activity of the septo-hippocampal system; Neuropsychopharmacology; 28(5); pp. 857-864; May 1, 2003.
Hass et al.; Waking with the hypothalamus. Pflugers Arch R Eur. J. Physiol.; 463(1): pp. 31-42; Jan. 1, 2012.
Herwig et al.; Intracortical excitability is modulated by a norepinephrine-reuptake inhibitor as measured with paired-pulse transcranial magnetic stimulation; Psychopharmacology (Berl); 164(2): pp. 228-232; Nov. 18, 2002.
Hirotsu et al.; Interactions between sleep, stress, and metabolism; From physiological to pathological conditions; Sleep Science; 8(3); pp. 143-152; Nov. 2015.
Horvath et al.; Evidence that transcranial direct current stimulation (tDCS) generates little-to-no reliable neurophysiologic effect beyond MEP amplitude modulation in healthy human subjects: A systematic review; Neuropsychologia; 66: pp. 213-236; Jan. 31, 2015.
Just et al.; Bold responses to trigeminal nerve stimulation; Magnetic Resonance Imaging; 28(8): pp. 1143-1151; Oct. 31, 2010.
Kanai et al.; Frequency-dependent electrical stimulatioin of the visual cortex; Curr. Biol.; 18(23); pp. 1839-1843; Dec. 9, 2008.
Kubota et al.; Role of the brain stem in cardiovascular changes induced by stimulation of the trigeminal nerve; Anesthesia Progress; 36(4-5); pp. 236-237; Jul. 1989.
Lee et al.; Neuromodulation of Brain States; Neuron; 76(1): pp. 209-222. Oct. 4, 2012.
Leproult et al.; Sleep loss results in an elevation of cortisol levels the next evening; Sleep; 20(10): pp. 865-870; Oct. 1997.
Lovibond et al.; The structure of negative emotional states: Comparison of the Depression Anxiety Stress Scales (DASS) with the Beck Depression and Anxiety Inventories; Behaviour Research and Therapy; 33(3); pp. 335-343; Mar. 31, 1995.
Lu et al.; A putative flip-flop switch for control of REM sleep; Nature; 441 (7093): pp. 589-594; Jun. 1, 2006.
Magis et al.; Safety and patients' satisfaction of transcutaneous supraorbital neurostimulation (tSNS) with the Cefaly(R) device in headache treatment: a survey of 2,313 headache sufferers in the general population; The Journal of Headache and Pain, 14(1); pp. 95; (manuscript version, 8 pages) Dec. 1, 2013.
McGough et al.; An eight-week, open-trial, pilot feasibility study of trigeminal nerve stimulation in youth with attention-deficit/hyperactivity disorder; Brain Stimulation; 8(2); pp. 299-304; Apr. 30, 2015.
Meltzer et al; Direct comparison of two new actigraphs and polysomnography in children and adolescents; Sleep; 35(1); pp. 159-166; Jan. 1, 2012.
Nash et al.; Differential activation of the human trigeminal nuclear complex by noxious and non-noxious orofacial stimulation; Human Brain Mapping; 30(11); pp. 3772-3782; Nov. 1, 2009.
Nieuwenhuis et al.; Decision making, the P3, and the locus coeruleus-norepinephrine system; Psychological Bulletin; 131(4); pp. 510-532; Jul. 2005.
Parvizi et al.; Consciousness and the brainstem; Cognition; 79(1): pp. 135-160; Apr. 30, 2001.
Paulus, W.; Transcranial electrical stimulation (tES-tDCS; tRNS, tACS) methods; Neuropsychol Rehabil.; 21(5); pp. 602-617; Oct. 2011.
Penzel et al.; Dynamics of Heart Rate and Sleep Stages in Normals and Patients with Sleep Apnea; Neuropsychopharmacology; 28(S1); pp. S48-S53; Jul. 1, 2003.
Piquet et al.; Supraorbital transcutaneous neurostimulation has sedative effects in healthy subjects; BMC Neurology; 11(1); p. 135; (manual transcript, 8 pages); Oct. 28, 2011.
Plewnia et al.; Enhancement of human cortico-motoneuronal excitability by the selective norepinephrine reuptake inhibitor reboxetine; Neuroscience Letters; 330(3); pp. 231-234; Sep. 27, 2002.
Prausnitz; The effects of electric current applied to skin: a review for transdermal drug delivery; Advanced Drug Delivery Reviews; vol. 18; pp. 395-425; Feb. 8, 1996.
Pusch et al.; Electrical stimulation of the vestibular system prevents postoperative nausea and vomiting; Acta Annesthesiol Scand.; 44(9); pp. 1145-1148; Oct. 2000.
Riemann et al.; The hyperarousal model of insomnia: A review of the concept and its evidence; Sleep Medicine Reviews; 14(1); pp. 19-31; Feb. 28, 2010.
Rill et al.; Pedunculopontine arousal system physiology—implications for insomnia; Sleep Science; 8(2); pp. 92-99; Jun. 30, 2015.
Rohleder et al.; Psychosocial stress-induced activation of salivary alpha-amylase: an indicator of sympathetic activity; Annals of the New York Academy of Sciences; 1032(1); pp. 258-263; Dec. 1, 2004.
Saiote et al.; High-frequency TRNS reduces BOLD activity during visuomotor learning; PLOS one; 8(3); e59669; 8 pgs.; Mar. 2013.
Sara; The locus coeruleus and noradrenergic modulation of cognition; Nature Reviews Neuroscience; 10(3): pp. 211-223. Mar. 1, 2009.
Schmidt et al.; Adrenaline rush: the role of adrenergic receptors in stimulant-induced behaviors; Molecular Pharmacology; 85(4): pp. 640-650; Apr. 1, 2014.
Schutter et al.; Brain oscillations and frequency-dependent modulation of cortical excitability; Brain Stimulation; 4(2); pp. 97-103; Apr. 2011.
Seugnet et al.; Identification of a biomarker for sleep drive in flies and humans; Proceedings of the National Academy of Sciences; 103(52); pp. 19913-19918; Dec. 26, 2006.
Shiozawa et al.; Transcutaneous vagus and trigeminal nerve stimulation for neuropsychiatric disorders: a systematic review; Arquivos de neuro-psiquiatria; 72(7): pp. 542-547; Jul. 2014.
Siegel; Brain mechanisms that control sleep and waking Naturwissenschaften; 91(8); pp. 355-365; Aug. 1, 2004.
Somana et al.; Cerebellar afferents from the trigeminal sensory nuclei in the cat. Brain Res.; 38(1); pp. 57-64; Jan. 1980.

(56) References Cited

OTHER PUBLICATIONS

STD Pharmaceutical Products; Idrostar intophoresis machine (product and use information); 9 pgs.; Dec. 2011 (printed Feb. 11, 2014 from http://www.iontophoresis.info/instructions/).

Strassman et al; Response of brainstem trigeminal neurons to electrical stimulation of the dura; Brain Research; 379(2): pp. 242-250; Aug. 6, 1986.

Tanaka et al.; Salivary alpha-amylase and cortisol responsiveness following electrically stimulated physical stress in bipolar disorder patients; Neuropsychiatric Disease and Treatment; 8; pp. 1899-1905; Jan. 1, 2013.

Terney et al.; Increasing human brain excitability by transcranial high-frequency random noise stimulation; The Journal of Neuroscience; 28(52); pp. 14127-14155; Dec. 2008.

Thoma et al.; Acute stress responses in salivary alpha-amylase predict increases of plasma norepinephrine; Biological Psychology; 91(3): pp. 342-348; Dec. 31, 2012.

Tremblay et al.; Uncertain Outcome of Prefrontal tDCS; Brain Stimulation; 7(6): pp. 773-783; Dec. 31, 2014.

Trevizol et al.; Trigeminal Nerve Stimulation (TNS) for Generalized Anxiety Disorder: A Case Study; Brain Stimulation; 8(3): pp. 659-660; Jan. 1, 2015.

Trevizol et al.; Trigeminal Nerve Stimulation (TNS) for Posttraumatic Stress Disorder: A Case Study; Brain Stimulation; 8(3): pp. 676-678; Jan. 1, 2015.

Turi et al.; Both the cutaneous sensation and phosphene perception are modulated in a frequency-specific manner during transcranial alternating current stimulation; Restor. Neural. Neurosci.; 31(3); pp. 275-285; Jan. 2013.

Tyler et al.; Transdermal neuromodulation of noradrenergic activity suppresses psychophysiological and biochemical stress responses in humans; Scientific Reports; 5; (manual transcript, 22 pages); Feb. 8, 2015.

Tyler et al.; U.S. Appl. No. 61/550,334 entitled "Improvement of Direct Communication," filed Oct. 21, 2011.

Tyler et al.; U.S. Appl. No. 61/663,409 entitled "Device and Methods for Noninvasive Neuromodulation Using Targeted Transcranial Electrical Stimulation," filed Jun. 22, 2012.

Tyler et al.; U.S. Appl. No. 62/166,674 entitled "Systems and Methods for Suppression of Stress Responses by Transdermal Electrical Neuromodulation," filed May 26, 2015.

Upadhyay et al.; Noninvasive mapping of human trigeminal brainstem pathways; Magnetic Resonance in Medicine; 60(5): pp. 1037-1046; Nov. 1, 2008.

Van Stegeren et al.; Salivary alpha amylase as marker for adrenergic activity during stress: effect of betablockade; Psychoneuroendocrinology; 31(1); pp. 137-141; Jan. 31, 2006.

Voisin et al.; Nociceptive stimulation activates locus coeruleus neurones projecting to the somatosensory thalamus in the rat; The Journal of Physiology; 566( 3); pp. 929-937; Aug. 1, 2005.

Voss et al.; Induction of self awareness in dreams through frontal low current stimulation of gamma activity; Nature Neuroscience; 17(6); pp. 810-812; Jun. 1, 2014.

Watson et al.; Development and validation of brief measures of positive and negative affect: the PANAS scales; Jouranl of Personality and Social Psychology; 54(6); pp. 1063-1070; Jun. 1988.

Weiss et al; Validity of Activity-Based Devices to Estimate Sleep; Journal of Clinical Sleep Medicine : 6(4); pp. 336-342; Aug. 2010.

Goldwasser et al.; U.S. Appl. No. 15/264,224 entitled "Apparatuses and methods for neuromodulation," filed Sep. 13, 2016.

Charlesworth et al.; U.S. Appl. No. 15/384,249 entitled "Apparatuses and methods for transdermal electrical stimulation of nerves to modify or induce a cognitive state," filed Dec. 19, 2017.

Jeffery; U.S. Appl. No. 15/380,028 entitled "Electrodes having surface exclusions," filed Dec. 15, 2017.

Pal et al.; U.S. Appl. No. 14/956,193 entitled "Transdermal electrical stimulation devices for modifying or inducing cognitive state," filed Dec. 1, 2015.

Tyler et al.; U.S. Appl. No. 15/536,148 entitled "Methods and apparatuses for transdermal stimulation of the outer ear," filed Jun. 15, 2017.

Tyler et al.; U.S. Appl. No. 15/536,151 entitled "Systems and methods for transdermal electrical stimulation to improve sleep," filed Jun. 15, 2017.

\* cited by examiner

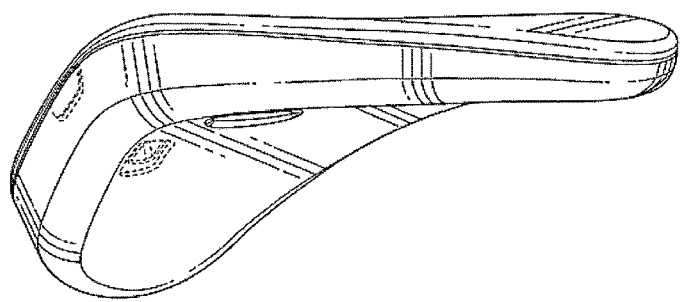
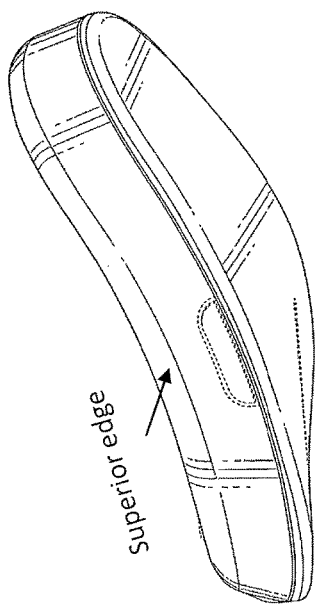
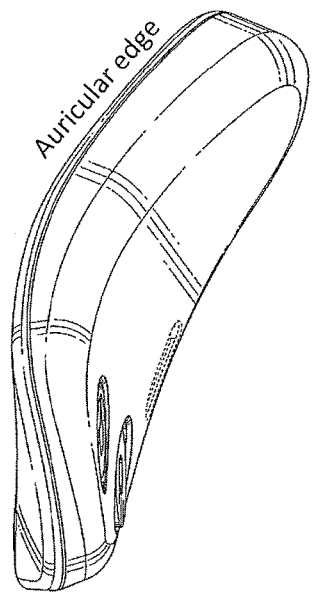
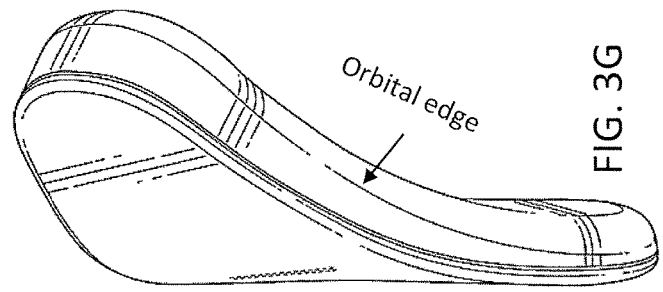
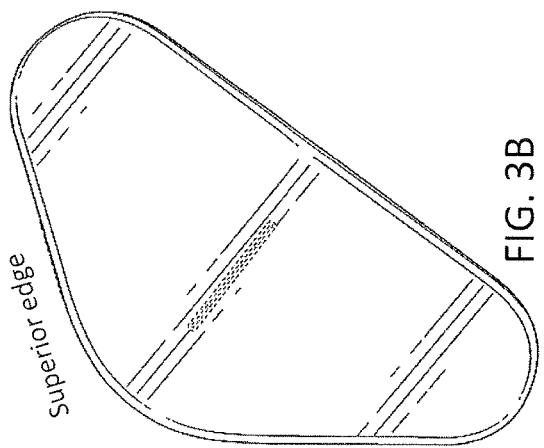
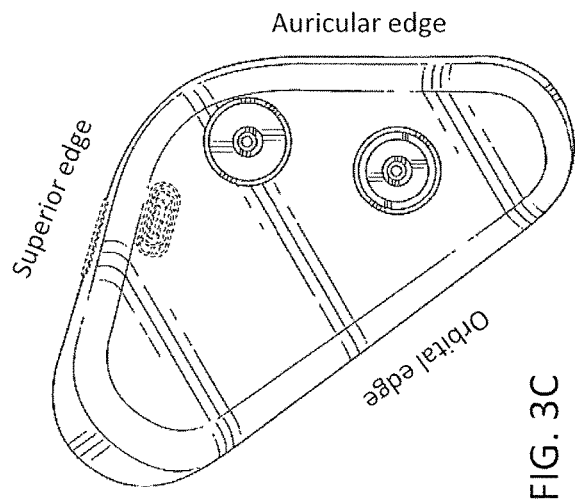

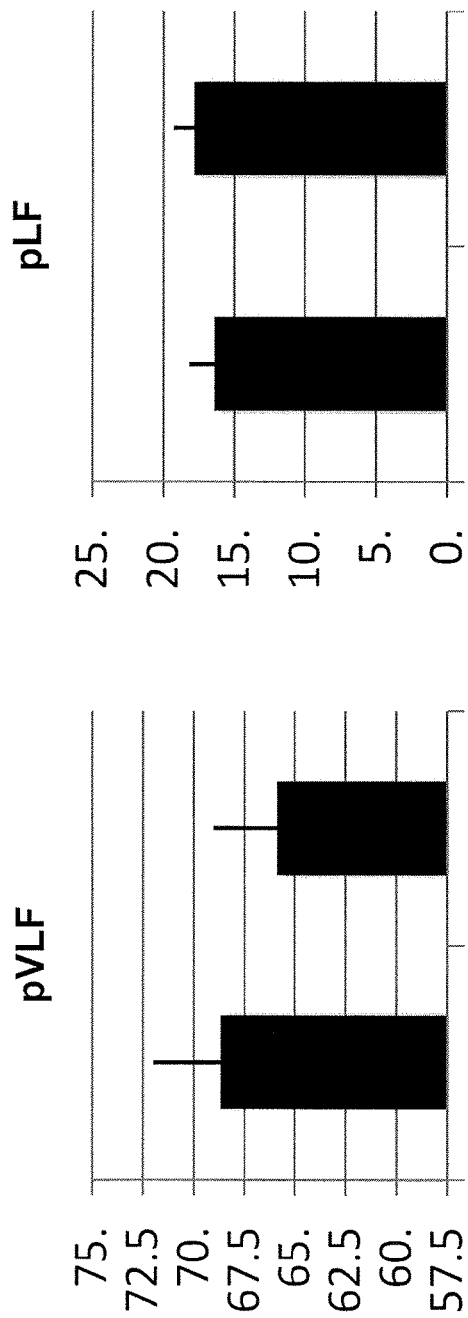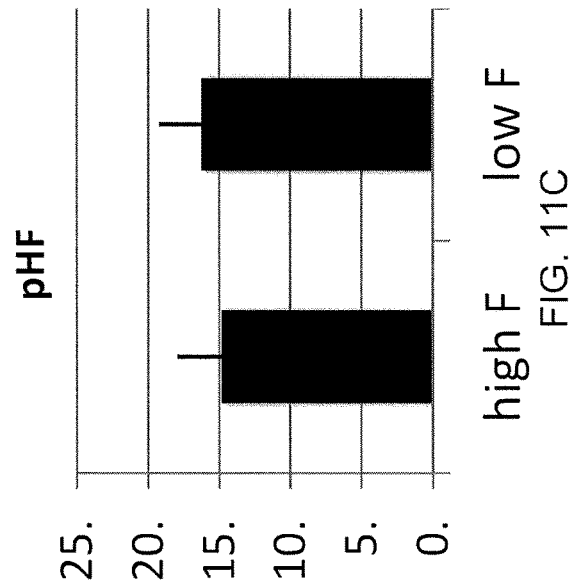
FIG. 11A  FIG. 11B  FIG. 11C

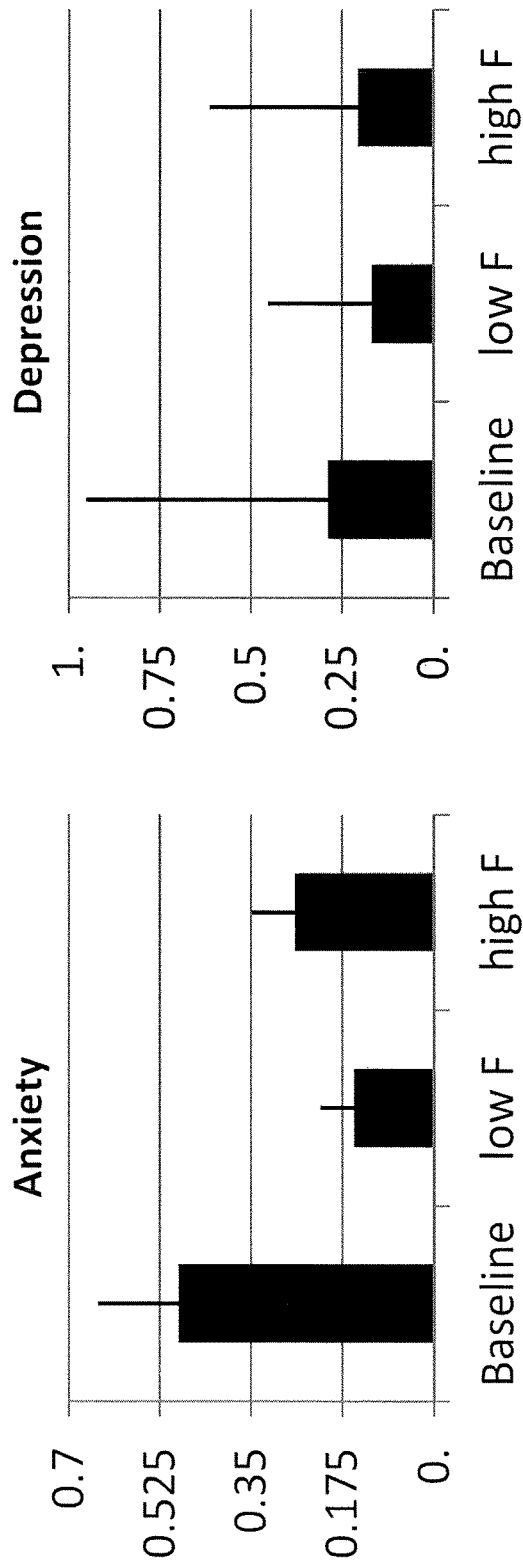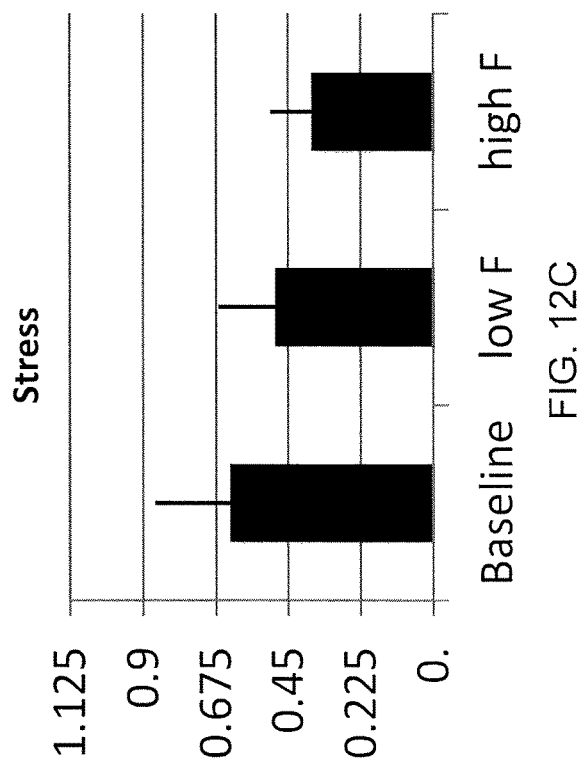
FIG. 12A
FIG. 12B
FIG. 12C

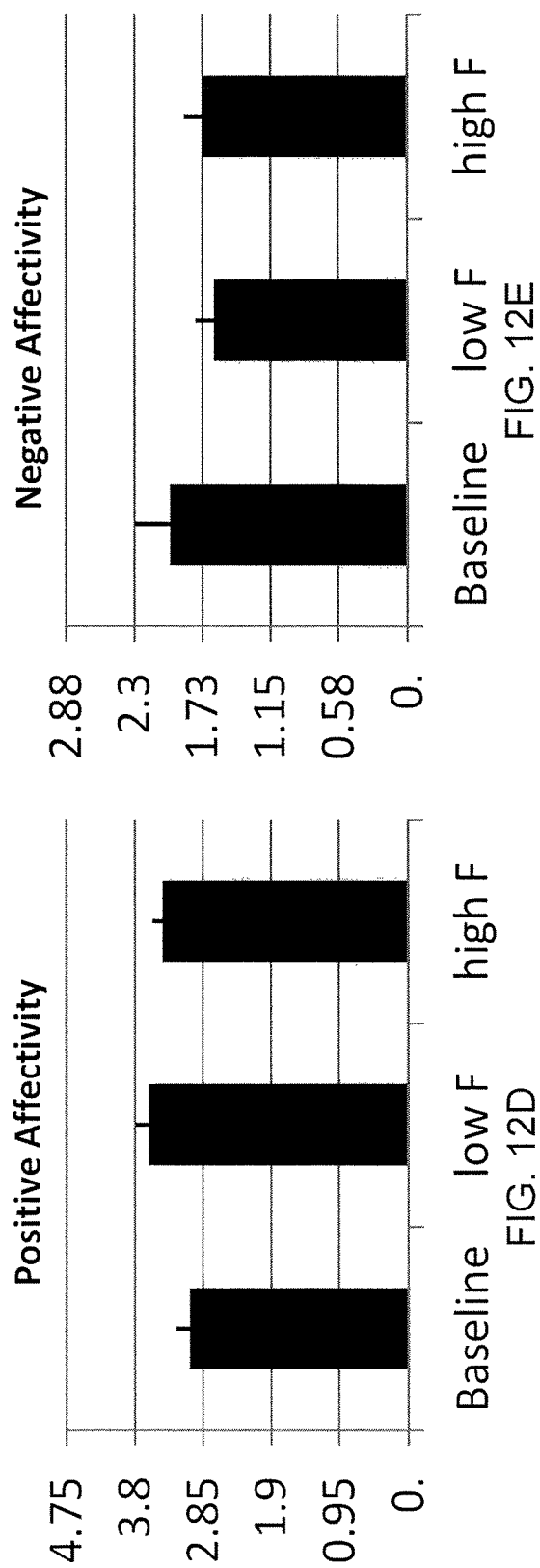
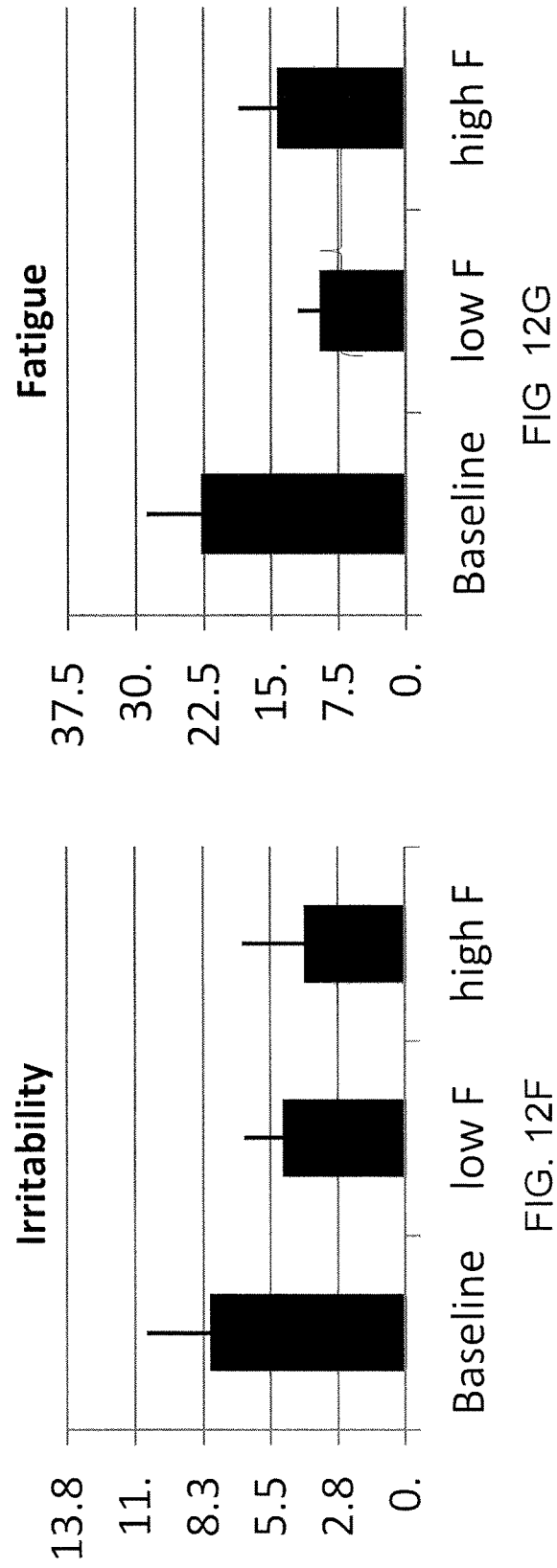

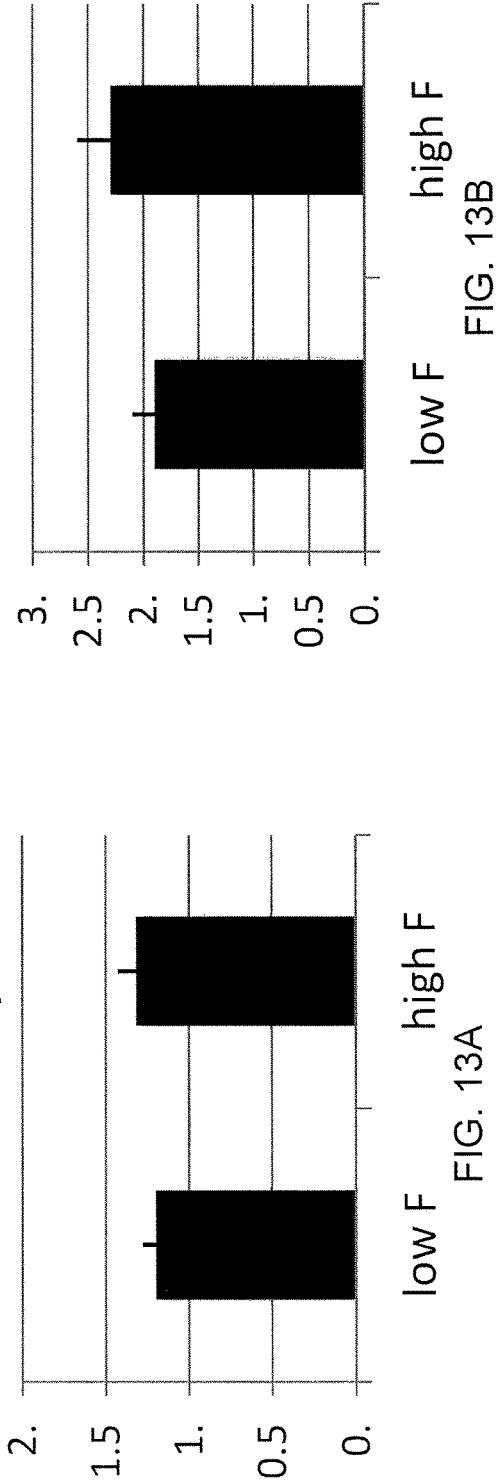
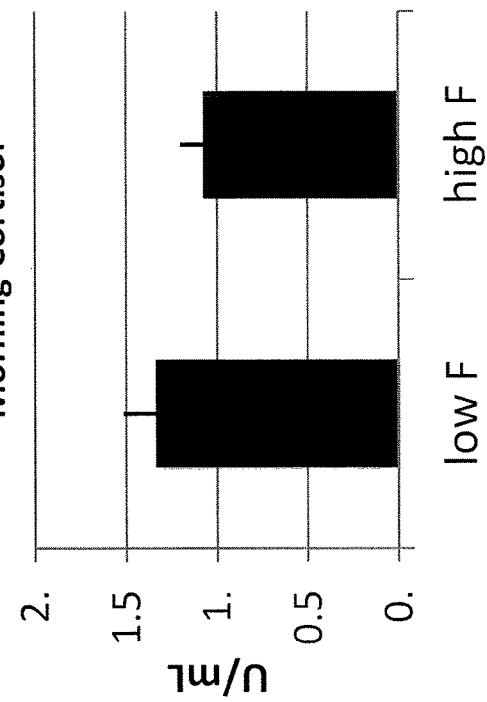
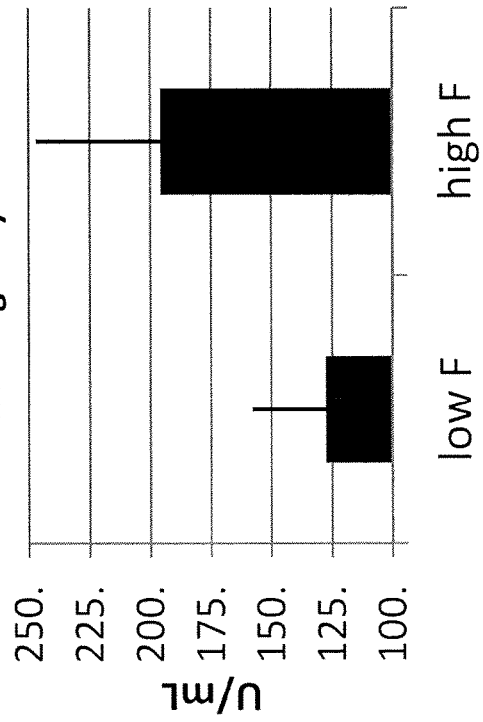
FIG. 13A
FIG. 13B
FIG. 14A
FIG. 14B

FIG. 15A

| | | | | | | | | | | | | | | | | |
|---|---|---|---|---|---|---|---|---|---|---|---|---|---|---|---|---|
| Duration (sec) | 3 | 27 | 60 | 60 | 2 | 3 | 63 | 2 | 30 | 58 | 2 | 18 | 28 | 10 | 60 | 5 |
| Frequency (Hz) | 11000 | 11000 | 11000 | 11000 | 11000 | 11000 | 11000 | 11000 | 11000 | 11000 | 11000 | 11000 | 11000 | 7500 | 6700 | 6700 |
| Current (mA) | 0 | 16 | 18 | 18 | 11 | 18 | 18 | 11 | 18 | 18 | 11 | 18 | 18 | 11 | 11 | 0 |
| Percent charge imbalance | 85 | 85 | 85 | 85 | 85 | 85 | 85 | 85 | 85 | 85 | 85 | 85 | 85 | 100 | 100 | 0 |
| Percent Duty Cycle | 41 | 41 | 41 | 41 | 41 | 41 | 41 | 41 | 41 | 41 | 41 | 41 | 41 | 38 | 38 | 0 |
| End time | 3 | 30 | 90 | 150 | 152 | 155 | 218 | 220 | 250 | 308 | 310 | 328 | 356 | 366 | 426 | 431 |

FIG. 15B

| Component Waveform # | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Duration | 2 | 28 | 30 | 60 | 1 | 4 | 65 | 1 | 20 | 69 | 1 | 20 | 59 | 1 | 20 | 59 | 30 |
| Freq. (Hz) | 11000 | 11000 | 11000 | 11000 | 11000 | 11000 | 11000 | 11000 | 11000 | 11000 | 11000 | 11000 | 11000 | 11000 | 11000 | 11000 | 7500 |
| Current (mA) | 1 | 16 | 19 | 19 | 12 | 19 | 19 | 11 | 19 | 19 | 19 | 12 | 19 | 19 | 12 | 19 | 12 |
| % Charge imb. | 85 | 85 | 85 | 85 | 85 | 85 | 85 | 85 | 85 | 85 | 85 | 85 | 85 | 85 | 85 | 85 | 100 |
| % Duty Cycle | 39 | 41 | 41 | 41 | 41 | 41 | 41 | 41 | 41 | 41 | 41 | 41 | 41 | 41 | 41 | 41 | 38 |
| End time | 2 | 30 | 60 | 120 | 121 | 125 | 190 | 191 | 211 | 280 | 281 | 301 | 360 | 361 | 381 | 440 | 470 |

| Component Waveform # | 18 | 19 | 20 | 21 | 22 | 23 | 24 | 25 | 26 | 27 |
|---|---|---|---|---|---|---|---|---|---|---|
| Duration | 30 | 30 | 60 | 0.4 | 59.6 | 0.4 | 59.6 | 0.4 | 39.6 | 5 |
| Freq. (Hz) | 7500 | 7500 | 6800 | 7500 | 6700 | 7500 | 6700 | 7500 | 6800 | 6800 |
| Current (mA) | 0 | 12 | 12 | 12 | 12 | 12 | 12 | 12 | 12 | 0 |
| % Charge imb. | 100 | 100 | 100 | 100 | 100 | 100 | 100 | 100 | 100 | 100 |
| % Duty Cycle | 38 | 38 | 38 | 38 | 38 | 38 | 38 | 38 | 38 | 38 |
| End time | 470 | 500 | 560 | 560.4 | 620 | 620.4 | 680 | 680.4 | 720 | 725 |

| Component Waveform # | 1 | 2 | 3 | 4 | 5 | 6 | 7 | 8 | 10 | 11 | 12 | 13 | 14 | 15 | 16 | 17 |
|---|---|---|---|---|---|---|---|---|---|---|---|---|---|---|---|---|
| Duration | 2 | 28 | 60 | 60 | 4 | 6 | 60 | 4 | 26 | 60 | 4 | 26 | 60 | 4 | 26 | 30 |
| Freq. (Hz) | 11000 | 11000 | 11000 | 10600 | 11000 | 11000 | 10600 | 11000 | 11000 | 10600 | 11000 | 11000 | 10600 | 11000 | 11000 | 7500 |
| Current (mA) | 1 | 16 | 19 | 19 | 11 | 16 | 19 | 11 | 19 | 19 | 11 | 19 | 19 | 11 | 19 | 1 |
| % Charge imb. | 90 | 90 | 90 | 90 | 90 | 90 | 90 | 85 | 90 | 90 | 85 | 90 | 90 | 85 | 90 | 100 |
| % Duty Cycle | 41 | 41 | 41 | 41 | 41 | 41 | 41 | 41 | 41 | 41 | 41 | 41 | 41 | 41 | 41 | 41 |
| End time | 2 | 30 | 90 | 150 | 154 | 160 | 220 | 224 | 250 | 310 | 314 | 340 | 400 | 404 | 430 | 460 |

| Component Waveform # | 18 | 19 | 20 | 21 | 22 | 23 | 24 | 25 | 26 | 27 | 28 | 29 | 30 | 31 | 32 | 33 |
|---|---|---|---|---|---|---|---|---|---|---|---|---|---|---|---|---|
| Duration | 40 | 60 | 2 | 58 | 2 | 58 | 2 | 58 | 10 | 30 | 30 | 30 | 4 | 16 | 80 | 5 |
| Freq. (Hz) | 7500 | 6700 | 7500 | 6700 | 7600 | 6700 | 7500 | 6700 | 11000 | 11000 | 11000 | 10500 | 11000 | 11000 | 10500 | 10800 |
| Current (mA) | 11 | 11 | 11 | 11 | 11 | 11 | 11 | 11 | 1 | 16 | 19 | 19 | 11 | 19 | 19 | 0 |
| % Charge imb. | 100 | 100 | 100 | 100 | 100 | 100 | 100 | 100 | 85 | 90 | 90 | 90 | 85 | 90 | 90 | 85 |
| % Duty Cycle | 39 | 39 | 39 | 39 | 39 | 39 | 39 | 39 | 39 | 41 | 41 | 41 | 43 | 41 | 41 | 41 |
| End time | 500 | 560 | 562 | 620 | 622 | 580 | 682 | 740 | 750 | 780 | 810 | 840 | 844 | 860 | 940 | 945 |

FIG. 15C

| Component Waveform # | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Duration | 1 | 59 | 75 | 30 | 90 | 30 | 120 | 30 | 90 | 30 | 30 | 60 | 30 | 90 | 30 | 120 |
| Freq. (Hz) | 9000 | 9000 | 9000 | 750 | 750 | 3600 | 3600 | 750 | 750 | 9000 | 9000 | 9000 | 750 | 750 | 3600 | 3600 |
| Current (mA) | 0 | 9.1 | 10.9 | 3 | 3.1 | 8 | 9.3 | 3.2 | 3.3 | 3 | 9.5 | 11.4 | 3.3 | 3.4 | 8.5 | 9.8 |
| % Charge imb. | 30 | 30 | 30 | 30 | 35 | 40 | 40 | 35 | 35 | 30 | 30 | 30 | 30 | 35 | 40 | 40 |
| % Duty Cycle | 50 | 50 | 50 | 35 | 40 | 40 | 40 | 35 | 40 | 50 | 50 | 50 | 35 | 40 | 40 | 40 |
| End time | 1 | 60 | 135 | 165 | 255 | 285 | 405 | 435 | 525 | 555 | 585 | 645 | 675 | 765 | 795 | 915 |

| Component Waveform # | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| Duration | 30 | 90 | 60 | 0.4 | 1.2 | 0.4 | 2 | 0.4 | 1.2 | 0.4 | 2 | 0.4 | 1.2 | 0.4 | 20 | 0.4 |
| Freq. (Hz) | 750 | 750 | 750 | 1300 | 1300 | 750 | 750 | 1600 | 1600 | 750 | 750 | 1800 | 1800 | 750 | 750 | 2000 |
| Current (mA) | 3.4 | 3.5 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 | 35 |
| % Duty Cycle | 35 | 40 | 40 | 40 | 40 | 40 | 40 | 40 | 40 | 40 | 40 | 40 | 40 | 40 | 40 | 40 |
| End time | 945 | 1035 | 1095 | 1095.4 | 1096.6 | 1097 | 1099 | 1099.4 | 1100.6 | 1101 | 1103 | 1103 | 1104.6 | 1105 | 1125 | 1125 |

| Component Waveform # | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|
| Duration | 1.2 | 0.4 | 2 | 0.4 | 1.2 | 0.4 | 2 | 0.4 | 1.2 | 0.4 | 2 | 0.4 | 1.2 | 0.4 | 101 |
| Freq. (Hz) | 2000 | 750 | 750 | 2000 | 2000 | 750 | 750 | 2000 | 2000 | 750 | 750 | 2000 | 2000 | 750 | 750 |
| Current (mA) | 4 | 4 | 4 | 4 | 4 | 4 | 4 | 4 | 4 | 4 | 4 | 4 | 4 | 4 | 4 |
| % Charge imb. | 35 | 35 | 35 | 35 | 35 | 35 | 35 | 35 | 35 | 35 | 35 | 35 | 35 | 35 | 35 |
| % Duty Cycle | 40 | 40 | 40 | 40 | 40 | 40 | 40 | 40 | 40 | 40 | 40 | 40 | 40 | 40 | 45 |
| End time | 1127 | 1127 | 1129 | 1129.4 | 1130.6 | 1131 | 1133 | 1133.4 | 1134.6 | 1135 | 1137 | 1137 | 1138.6 | 1139 | 1240 |

FIG. 16

| Component Waveform # | 1 | 2 | 3 | 4 | 5 | 6 | 7 |
|---|---|---|---|---|---|---|---|
| Duration (s) | 1 | 269 | 30 | 270 | 30 | 270 | 30 |
| Frequency (Hz) | 500 | 500 | 550 | 500 | 550 | 500 | 550 |
| Current (mA) | 0 | 3.5 | 3.5 | 3.5 | 3.5 | 3.5 | 3.5 |
| % charge imb. | 3% | 3% | 3% | 3% | 3% | 3% | 3% |
| % Duty Cycle | 25%-35%* | 25%-35%* | 25%-35%* | 25%-35%* | 25%-35%* | 25%-35%* | 25%-35%* |
| End time | 1 | 270 | 300 | 570 | 600 | 870 | 900 |

* User adjustable within this range

FIG. 17

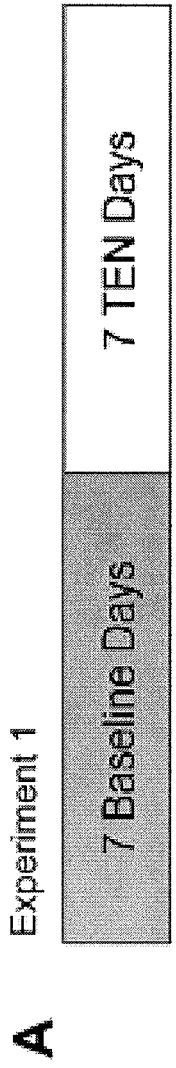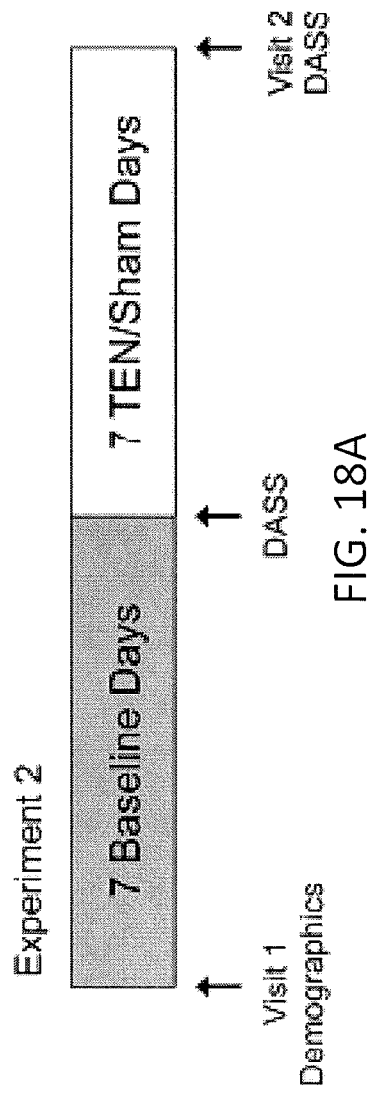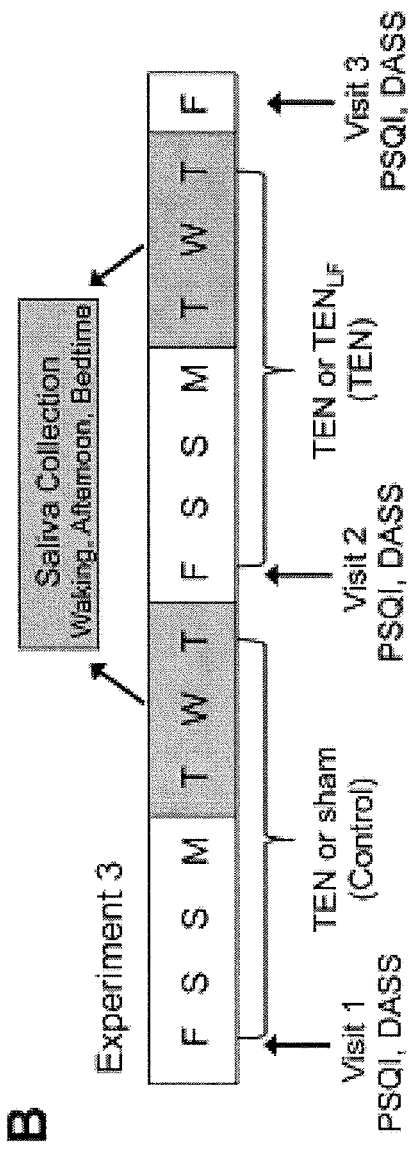
FIG. 18A
FIG. 18B

|  | Baseline M (SD) | TEN M (SD) | Scale |
|---|---|---|---|
| Drowsiness | 3.97 (1.63) | 2.89 (1.28)* | |
| Refreshment | 4.88 (1.89) | 5.79 (1.74)* | |
| Negative Affect | 2.23 (0.83) | 2.42 (0.85)* | PANAS |
| Positive Affect | 1.31 (0.27) | 1.17 (0.17)* | |
| Depression | 4.07 (5.35) | 3.43 (5.65) | |
| Anxiety | 3.10 (2.71) | 2.17 (3.12)* | DASS |
| Stress | 10.00 (6.96) | 5.87 (5.31)* | |

FIG. 20

|  | Sham Treatment Group | | TEN Treatment Group | |
| --- | --- | --- | --- | --- |
|  | Baseline M (SD) | Sham M (SD) | Baseline M (SD) | TEN M (SD) |
| Drowsiness | 4.35 (1.30) | 3.91 (1.15) | 4.69 (1.59) | 3.80 (1.63)* |
| Refreshment | 3.77 (1.06) | 3.89 (0.87) | 3.89 (0.76) | 4.41 (0.78)* |
| Negative Affect | 2.17 (0.58) | 2.30 (0.72) | 2.04 (0.52) | 2.26 (0.64) |
| Positive Affect | 1.40 (0.40) | 1.41 (0.51) | 1.28 (0.28) | 1.27 (.034)* |
| Sleep Quality | 4.58 (0.70) | 4.36 (0.96) | 4.51 (0.90) | 5.01 (0.89)* |
| # of Awakenings | 1.41 (1.23) | 1.20 (1.40) | 1.19 (0.84) | 0.75 (0.62)* |

FIG. 21

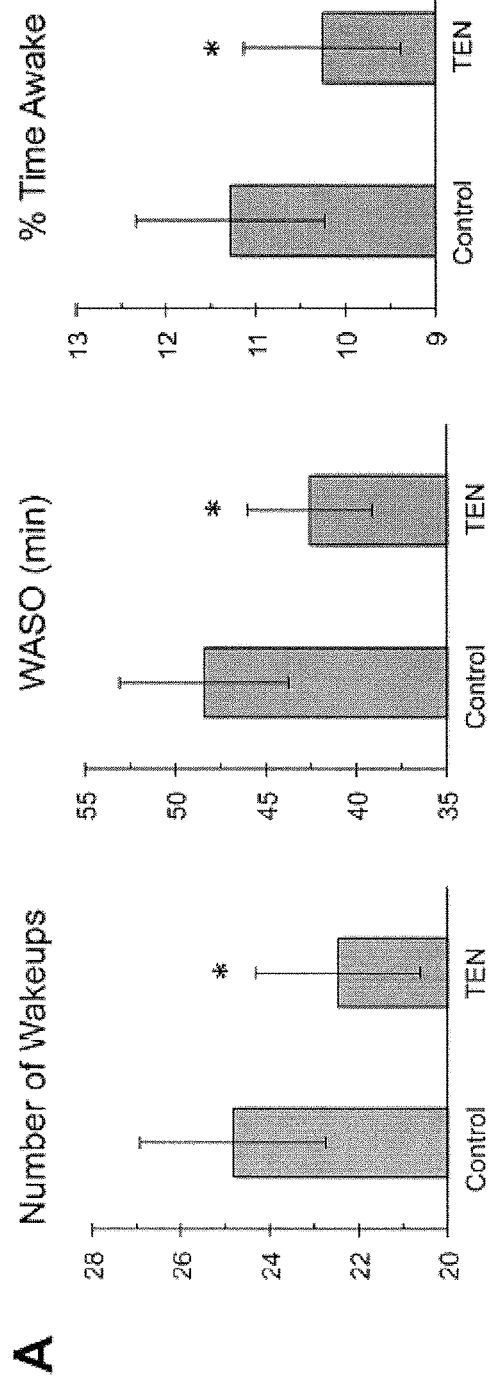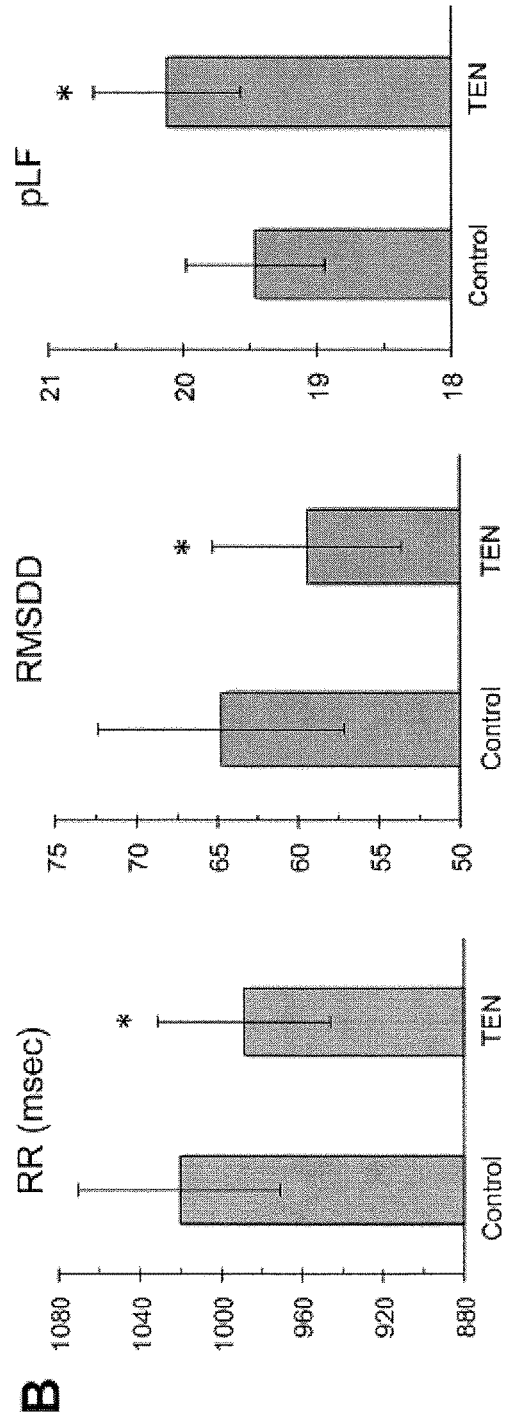
FIG. 24A
FIG. 24B

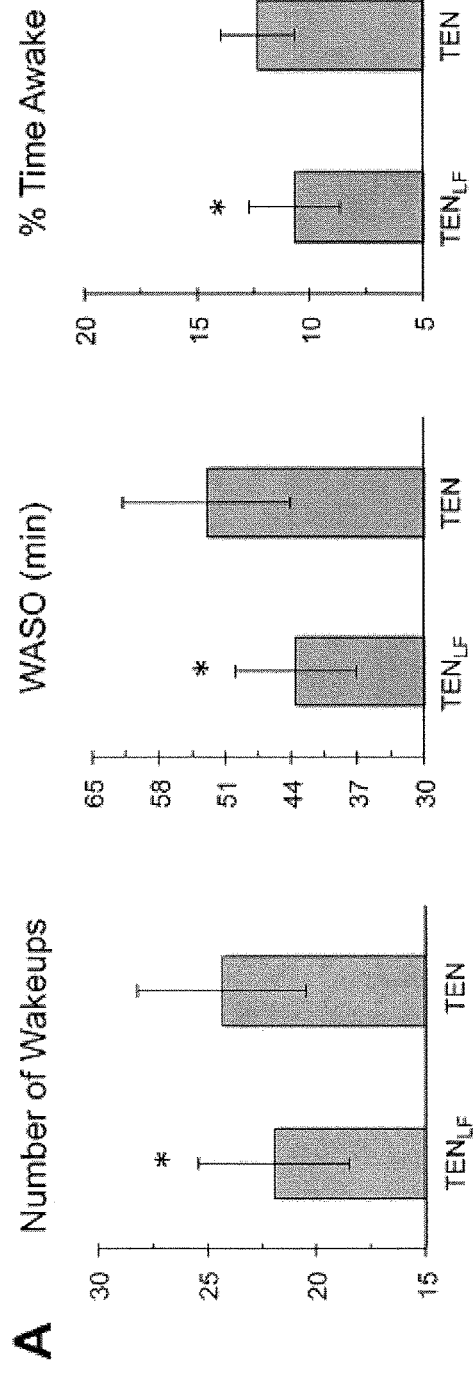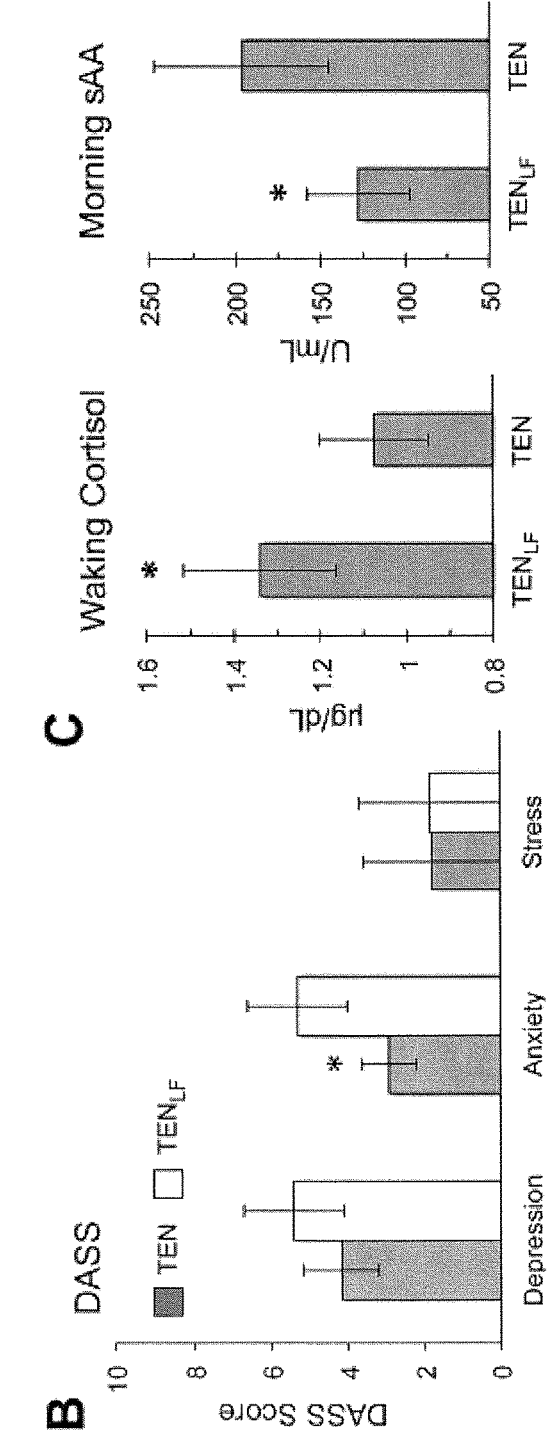
FIGS. 25A
FIGS. 25B
FIGS. 25C

SYSTEMS AND METHODS FOR TRANSDERMAL ELECTRICAL STIMULATION TO IMPROVE SLEEP

CROSS REFERENCE TO RELATED APPLICATIONS

This patent application claims priority to U.S. Provisional Patent Application No. 62/308,845, titled TRANSDERMAL ELECTRICAL NEUROMODULATION OF THE TRIGEMINAL SENSORY NUCLEAR COMPLEX IMPROVES SLEEP QUALITY AND MOOD," filed Mar. 15, 2016, which is herein incorporated by reference in its entirety.

This application also claims priority as a continuation-in-part of International Patent Application No. PCT/US2016/012128, titled "SYSTEMS AND METHODS FOR TRANSDERMAL ELECTRICAL STIMULATION TO IMPROVE SLEEP," filed Jan. 5, 2016, Publication No. WO 2016/111974, which claims priority to U.S. Provisional Patent Application No. 62/100,004, titled "SYSTEMS FOR TRANSDERMAL ELECTRICAL STIMULATION TO IMPROVE SLEEP AND METHODS OF USING THEM," filed Jan. 5, 2015, each of which are herein incorporated by reference in its entirety.

This application also claims priority as a continuation-in-part to U.S. patent application Ser. No. 15/264,224, titled "APPARATUSES AND METHODS FOR NEUROMODULATION," filed Sep. 13, 2016, which is a continuation-in-part of U.S. patent application Ser. No. 14/558,604, titled "WEARABLE TRANSDERMAL ELECTRICAL STIMULATION DEVICES AND METHODS OF USING THEM," filed Dec. 2, 2014, now U.S. Pat. No. 9,440,070, which is a continuation-in-part of U.S. patent application Ser. No. 14/091,121, titled "WEARABLE TRANSDERMAL ELECTRICAL STIMULATION DEVICES AND METHODS OF USING THEM," filed Nov. 26, 2013, now U.S. Pat. No. 8,903,494, which claims the benefit of U.S. Provisional Patent Application No. 61/729,851, titled "DISPOSABLE AND SEMI-DISPOSABLE TRANSCRANIAL ELECTRICAL STIMULATION SYSTEMS," filed Nov. 26, 2012; U.S. Provisional Patent Application No. 61/765,795, titled "TRANSCRANIAL ELECTRICAL STIMULATION SYSTEMS," filed Feb. 17, 2013; U.S. Provisional Patent Application No. 61/767,945, titled "TRANSCRANIAL NEUROMODULATION SYSTEMS," filed Feb. 22, 2013; U.S. Provisional Patent Application No. 61/770,479, titled "TRANSCRANIAL NEUROMODULATION CONTROLLER AND DELIVERY SYSTEMS," filed Feb. 28, 2013; U.S. Provisional Patent Application No. 61/841,308, titled "TRANSCRANIAL ELECTRICAL STIMULATIONS SYSTEMS," filed Jun. 29, 2013; U.S. Provisional Patent Application No. 61/845,845, titled "TRANSCRANIAL ELECTRICAL STIMULATION SYSTEMS AND METHODS," filed Jul. 12, 2013; U.S. Provisional Patent Application No. 61/875,424, titled "TRANSCRANIAL ELECTRICAL STIMULATION SYSTEMS AND METHODS," filed Sep. 9, 2013; U.S. Provisional Patent Application No. 61/900,880, titled "NEUROMODULATION CONTROL AND USER INTERFACE SYSTEMS," filed Nov. 6, 2013; U.S. Provisional Patent Application No. 61/875,891, titled "SYSTEMS AND METHODS FOR TRANSCRANIAL ELECTRICAL STIMULATION DURING A PERFORMANCE OR GROUP INVENT," filed Sep. 10, 2013; U.S. Provisional Patent Application No. 61/888,910, titled "TRANSCRANIAL ELECTRICAL STIMULATION SYSTEMS AND METHODS," filed Oct. 9, 2013; U.S. Provisional Patent Application No. 61/907,394, titled "TRANSCRANIAL ELECTRICAL STIMULATION SYSTEMS AND METHODS," filed Nov. 22, 2013. Each of these applications is herein incorporated by reference in its entirety.

U.S. patent application Ser. No. 14/558,604 also claims the benefit of U.S. Provisional Patent Application No. 62/076,459, titled "CANTILEVER ELECTRODES FOR TRANSDERMAL AND TRANSCRANIAL STIMULATION," filed Nov. 6, 2014, which is herein incorporated by reference in its entirety.

U.S. patent application Ser. No. 15/264,224 is also a continuation-in-part of U.S. patent application Ser. No. 15/170,878, titled "APPARATUSES AND METHODS FOR NEUROMODULATION," filed Jun. 1, 2016, Publication No. US-2016-0346545-A1, which claims priority to each of the following: U.S. Provisional Patent Application No. 62/169,522, titled "SYSTEMS AND METHODS FOR NEUROMODULATION TO TRANSFORM CONCURRENT SENSORY EXPERIENCES," filed Jun. 1, 2015; U.S. Provisional Patent Application No. 62/169,523, titled "APPARATUSES AND METHODS FOR NEUROMODULATION," filed Jun. 1, 2015; U.S. Provisional Patent Application No. 62/170,111, titled "SYSTEMS AND METHODS NEUROMODULATION WITH FACIAL AND MASTOID ELECTRODES," filed Jun. 2, 2015; and U.S. Provisional Patent Application No. 62/268,084, titled "SYSTEMS AND METHODS FOR NEUROMODULATION WITH FACIAL AND MASTOID ELECTRODES," filed Dec. 16, 2015. Each of these applications is herein incorporated by reference in its entirety.

U.S. patent application Ser. No. 15/264,224 is also a continuation-in-part of U.S. patent application Ser. No. 14/715,470, titled "TRANSDERMAL NEUROSTIMULATOR ADAPTED TO REDUCE CAPACITIVE BUILD-UP," filed May 18, 2015, now U.S. Pat. No. 9,474,891, which claims priority to U.S. Provisional Patent Application No. 62/002,910, titled "TRANSDERMAL ELECTRICAL STIMULATION ELECTRODE DEGRADATION DETECTION SYSTEMS AND METHODS OF USING THEM," filed May 25, 2014; U.S. Provisional Patent Application No. 62/076,459, titled "CANTILEVER ELECTRODES FOR TRANSDERMAL AND TRANSCRANIAL STIMULATION," filed Nov. 6, 2014; U.S. Provisional Patent Application No. 62/099,950, titled "CANTILEVER ELECTRODES FOR TRANSDERMAL AND TRANSCRANIAL STIMULATION," filed Jan. 5, 2015; U.S. Provisional Patent Application No. 62/075,896, titled "SYSTEMS AND METHODS FOR NEUROMODULATION," filed Nov. 6, 2014; U.S. Provisional Patent Application No. 62/099,960, titled "METHODS AND APPARATUSES FOR USER CONTROL OF NEUROSTIMULATION," filed Jan. 5, 2015; U.S. Provisional Patent Application No. 62/100,022, titled "WEARABLE TRANSDERMAL NEUROSTIMULATOR," filed Jan. 5, 2015. Each of these applications is herein incorporated by reference in its entirety.

U.S. patent application Ser. No. 15/264,224 is also a continuation-in-part of U.S. patent application Ser. No. 14/715,476, titled "METHODS AND APPARATUSES FOR AMPLITUDE-MODULATED ENSEMBLE WAVEFORMS FOR NEUROSTIMULATION," filed May 18, 2015, now U.S. Pat. No. 9,517,351, which claims priority to the following provisional patent applications: U.S. Provisional Patent Application No. 61/994,860, titled "SYSTEMS, DEVICES, AND METHODS FOR TRANSDERMAL ELECTRICAL STIMULATION WAVEFORM DESIGN AND USE," filed May 17, 2014, and U.S. Provisional Patent Application No. 62/100,029, titled "METHODS AND APPARATUSES FOR DELIVERY OF ENSEMBLE WAVEFORMS," filed Jan. 5, 2015. Each of these applications is herein incorporated by reference in its entirety.

U.S. patent application Ser. No. 15/264,224 is also a continuation-in-part of U.S. patent application Ser. No. 15/169,445, titled "METHODS AND APPARATUSES FOR TRANSDERMAL ELECTRICAL STIMULATION," filed May 31, 2016, Publication No. US-2016-0346530-A1, which claims priority to each of the following: U.S. Provisional Patent Application No. 62/168,615, titled "METHODS AND APPARATUSES FOR TRANSDERMAL ELECTRICAL STIMULATION," filed May 29, 2015; U.S. Provisional Patent Application No. 62/190,211, titled "METHODS AND APPARATUSES FOR TRANSDERMAL ELECTRICAL STIMULATION," filed Jul. 8, 2015; U.S. Provisional Patent Application No. 62/200,256, titled "METHODS AND APPARATUSES FOR TRANSDERMAL ELECTRICAL STIMULATION," filed Aug. 3, 2015; and U.S. Provisional Patent Application No. 62/213,949, titled "METHODS AND APPARATUSES FOR TRANSDERMAL ELECTRICAL STIMULATION," filed Sep. 3, 2015. Each of these applications is herein incorporated by reference in its entirety.

This application may also be related to one or more of the following applications: U.S. patent application Ser. No. 14/320,443, titled "TRANSDERMAL ELECTRICAL STIMULATION METHODS FOR MODIFYING OR INDUCING COGNITIVE STATE," filed Jun. 30, 2014, now U.S. Pat. No. 9,014,811; U.S. patent application Ser. No. 14/320,461, titled "TRANSDERMAL ELECTRICAL STIMULATION DEVICES FOR MODIFYING OR INDUCING COGNITIVE STATE," filed Jun. 30, 2014, now U.S. Pat. No. 9,002,458; U.S. patent application Ser. No. 14/639,015, titled "TRANSDERMAL ELECTRICAL STIMULATION DEVICES FOR MODIFYING OR INDUCING COGNITIVE STATE," filed Mar. 4, 2015, now U.S. Pat. No. 9,233,244; U.S. patent application Ser. No. 14/634,551, titled "METHODS FOR USER CONTROL OF NEUROSTIMULATION TO MODIFY A COGNITIVE STATE," filed Feb. 27, 2015, now U.S. Pat. No. 9,399,126. Each of these applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD OF THE INVENTION

This invention relates generally to methods and apparatuses for noninvasive neuromodulation, and more specifically to configurations and methods for transdermal electrical stimulation systems adapted to improve sleep and mood.

The present invention relates to methods and systems for transdermal electrical neuromodulation to modulate sleep. In particular described herein are neurostimulator apparatuses, generally wearable, configured to be applied to the user (e.g., the user's head and/or neck) to reduce sleep onset, lengthen sleep duration, improve sleep quality, and/or enhance the types and/or subtypes of sleep. In some variations these systems may improve sleep for subjects with sub-clinical or clinical sleep disturbances, including sleep disorders and sleep issues symptomatic to other diseases, disorders, or behaviors.

BACKGROUND

Sleep disturbances, including insomnia and sleeplessness, are known to affect a vast number of individuals. In addition, many individuals may wish to regulate or control their sleep as a lifestyle choice. Sleep disorders, as well sleep abnormalities symptomatic to a disorder, disease, behavior, or treatment (i.e. sleep issues that occur in response to ADHD treatment, chemotherapy, etc.) affect millions. Moreover, many individuals suffer from sub-clinical or undiagnosed sleep issues that severely affect health and well-being, causing a reduced quality of life. Currently, modulation of sleep and treatment of the symptoms of sleeping disorders is generally accomplished with pharmacological agents. Such agents may be expensive, have associated risk of overdose, and may have undesirable side effects. In addition some people are averse to using drugs to treat seemingly benign conditions such as insomnia and sleeplessness.

It would generally be advantageous to provide apparatuses (devices, systems) and methods for transdermal electrical stimulation for improving sleep. Specifically, there is a need for effective non-drug treatments (or enhancements for existing drug treatments) for sleep.

Described herein are transdermal electric stimulation (hereinafter "TES") apparatuses (devices and systems) and methods of using them that may be useful in treating sleep. TES (e.g., applied through scalp electrodes) has been used to affect brain function in humans. TES has been shown to improve motor control and motor learning, improve memory consolidation during slow-wave sleep, regulate decision-making and risk assessment, affect sensory perception, and cause movements. TES has been used therapeutically in various clinical applications, including treatment of pain, depression, epilepsy, and tinnitus. Despite the research to date on TES neurostimulation, existing methods and apparatuses for TES are lacking for applications related to the modulation of sleep.

For example, U.S. patent application Ser. No. 13/423,380 titled "DEVICE FOR CONVERTING MUSIC SIGNAL TO ELECTRICAL STIMULATION" by inventor Liang describes systems for adapting music therapy insomnia treatments by converting the analog auditory signal to a time-varying voltage signal delivered to transdermal electrodes targeting acupuncture points. However, audible waveforms of music appropriate for use as a musical therapy intervention for sleep are poorly adapted to transdermal electrical stimulation targeting peripheral nerves. An analog-adapted signal as described by Liang would likely lack high transient peak currents (i.e. pulsing) that may be effective for activating peripheral nerves, and further may be quite uncomfortable due to the presence of significant power in low frequencies (100 s of Hz) without duty cycle limitations.

U.S. patent application Ser. No. 12/616,513, titled "DEEP BRAIN STIMULATION FOR SLEEP AND MOVEMENT DISORDERS" by inventors Wu et al. describes an implantable electrical stimulation system targeting the substantia nigra to treat sleep disorders. The sleep stage of a patient is tracked and stimulation is modulated according to the patient's sleep stage. Such implantable systems have a greater cost and risk relative to noninvasive designs. Further, this invention requires some form of sleep tracking to modulate the applied electrical stimulation. It would be desirable to modulate sleep without requiring such tracking.

Similarly, U.S. Pat. No. 8,612,005 to inventors Rezai et al. titled "NEUROSTIMULATION FOR AFFECTING SLEEP DISORDERS" describes another technique for affecting a sleep disorder by stimulating a deep nucleus via an implanted electrode. Another implanted electrical treatment is described in U.S. Pat. No. 5,335,657 to inventors Terry Jr., et al. titled "THERAPEUTIC TREATMENT OF SLEEP DISORDER BY NERVE STIMULATION". This patent describes an implanted vagal nerve stimulator for treating sleep disorders.

Although non-invasive electrical stimulation devices to treat sleep have been proposed, such devices have not found wide use because they are not effective and/or they result in pain or discomfort during or after use. For example, U.S. Pat. No. 3,648,708 to inventor Haeri titled "ELECTRICAL THERAPEUTIC DEVICE" describes a device to be operated by a medical professional that delivers pulsed or alternating currents at lower frequencies (less than or equal to 250 Hz) for inducing relaxation or sleep. This invention is lacking at least due to the requirement for operation by a medical professional (unsuitability for self-actuation) and limitation to low frequencies that may limit the intensity of stimulation due to discomfort. Discomfort (e.g., due to skin irritation and/or muscle twitching) is believed to decrease with increasing frequency in a range above 250 Hz, thus low-frequency stimulation may be uncomfortable.

Similarly, U.S. Pat. No. 3,255,753 to inventor Wing titled "ELECTRICAL SLEEP MACHINE AND SLEEP INDUCING METHOD" uses a rechargeable battery to power an electrical stimulator and a self-timer as safety features that enable self-operation of the device. The pulses delivered are square pulses, generally less than 40 Hz. Such stimulation is likely to be uncomfortable and/or ineffective for inducing or improving sleep. Discomfort or pain invariably induces physiological arousal in a user and makes falling asleep more difficult.

U.S. Pat. No. 4,418,687 to inventors Matsumoto et al. titled "ELECTRIC SLEEP INDUCER" describes another low frequency (<14 Hz) electrical stimulator for inducing sleep by broadly inhibiting the cerebral cortex. This invention is inspired by the work by Gilyarovsky and colleagues in the mid-19th century that used low (<150 Hz) frequency stimulation to induce sleep.

U.S. Pat. No. 8,029,431 to inventor Tononi et al. titled "METHOD AND APPARATUS FOR PROMOTING RESTORATIVE SLEEP" also operates at brain rhythm (low frequencies), employing magnetic stimulation to entrain brain rhythms at slow-wave (delta) frequencies for enhancing restorative sleep. Such low-frequency magnetic systems may not target peripheral nerves (cranial nerves, vagal nerve, etc.) that can modulate autonomic function and brain state, but may operate under a different regime. Similarly, U.S. patent application Ser. No. 11/025,928 to inventor Wang titled "METHOD FOR MODERATION OF SLEEP DISORDER" describes methods for treating a sleep disorder using a magnetic head acupuncture headgear (see also U.S. Pat. No. 6,280,454 to Wang) for electrical stimulation at 0.3-3.4 kHz using many electrodes implanted on the scalp. These methods require a magnetic material, cap, or a large number of electrode locations making them difficult to operate and apply.

Finally, U.S. Pat. No. 5,792,067 to inventor Karell titled "APPARATUS AND METHOD FOR MITIGATING SLEEP AND OTHER DISORDERS THROUGH ELECTROMUSCULAR STIMULATION" describes a system and method of using an electrode placed on the user's palate or pharynx to mitigate snoring, apnea, etc. As implied by the title, this invention stimulates the muscles, e.g., within the oral cavity, to reduce snoring and/or apnea, and the internal (in the mouth) placement and the energy applied are likely to be uncomfortable, and does not directly modulate sleep (e.g., onset, duration, quality, etc.).

Thus, in general, it would be advantageous to provide apparatuses and methods for transdermal electrical stimulation for improving sleep that are both effective and comfortable for a user.

SUMMARY OF THE DISCLOSURE

The present invention relates to methods and apparatuses for improving sleep. Improving sleep may refer to reducing the time to fall asleep, including reducing sleep onset, increasing/causing drowsiness, and causing sleep. Improving sleep may also or alternatively include lengthening the duration of sleep or of certain portions of the sleep cycle (e.g., any of sleep stages: 1, 2, 3, 4 and REM sleep, slow wave sleep, etc.), reducing sleep interruptions (wakening), or the like.

In general, these methods may include applying the wearable TES applicator to the subject, and applying appropriate TES prior to falling asleep and/or during sleep. The TES applicator is typically applied by the patient herself, and in some variations the patient may manually adjust one or more of the TES waveform parameters to enhance comfort. The attachment sites for the electrodes may include at least one location on the head (e.g., the temple) and may also include a second location on the subject's head or neck (e.g., back of the neck). Alternatively two electrode locations may be on the neck; one electrode location may be on the subject's neck and a second electrode location may be below the neck; or two electrodes may be on the subject's skin below the neck.

For example, a method of non-invasively reducing sleep onset and increasing sleep duration may include attaching a first electrode to a subject's head or neck at a first location and a second electrode to the subject's head or neck at a second location, wherein the first and the second electrode are coupled to a transdermal electrical stimulation (TES) applicator worn by the subject. Once applied, the TES applicator may be used to apply an electrical stimulation between the first and second electrodes for a stimulation duration. The applied electrical stimulation may be an 'ensemble waveform' as described herein and described in U.S. application Ser. No. 14/715,476, filed May 18, 2015 (now Publication No. US-2015-0328461), previously incorporated by reference in its entirety. For example, the electrical stimulation may have a peak amplitude of greater than 3 mA, a frequency of greater than 250 Hz, and a duty cycle of greater than 10%. The application of the electrical stimulation may be continued for a stimulation duration of at least one minute to enhance sleepiness, sustain sleep or to enhance sleepiness and sustain sleep. For example, the stimulation duration (the time during which the TES waveform is being applied by the applicator) may be between 1 minute and 120 minutes, between 1 minute and 90 minutes, between 1 minute and 60 minutes, etc., or may be between any lower value (where the lower value may be 0.5, 1, 2, 3, 4, 5, 6, 7, 8, 9, 10, 11, 12, 13, 14, 15, 20, 25, 30, 35, 40, 45, 50, 55, 60, 75, 90, 105, 120, etc. minutes) and an upper value (where the upper value may be 2, 3, 4, 5, 6, 7, 8, 9, 10, 11, 12, 13, 14, 15, 20, 25, 30, 35, 40, 45, 50, 55, 60, 75, 90, 105, 120, 150, etc. minutes), and the lower value is always lower than the upper value.

The wearable TES applicator may be attached by any appropriate method, including adhesively attaching, attaching using a strap, attaching via a garment such as a hat, band, etc., attaching via a bandage or wrap, or the like. As mentioned, the first electrode may be attached to the subject's head, e.g., to the subject's temple region, forehead region, etc. The first electrode may be on or attached directly to the body of the wearable TES applicator. The second electrode may also be attached to the subject's head or neck; for example, the second electrode may be attached to the subject's neck above the subject's vertebra prominens.

Any of these methods may allow the subject (who may also be referred to as the user) to select a set of parameters for the electrical stimulation to be applied. Any individual or combination of parameters may be modulated/set by the user, and this modulation may be performed before and/or during the application of the stimulation. For example, a subject may modify one or more parameters such as: stimulation duration, frequency, peak amplitude, duty cycle, capacitive discharge on or off, and DC offset. The adjustment may be made within a fixed/predetermined range of values (e.g., for frequency, the subject may adjust the frequency between a minimum value, such as 250 Hz, and a maximum value, such as 40 kHz, or any sub-range therebetween).

The TES applicator may be worn (and energy applied) while the subject is awake, before sleeping, and/or while the subject sleeps. In some variations, the apparatus (including the first and second electrodes and TES applicator) may be removed prior to the subject sleeping.

TES ensemble waveforms appropriate for enhancing sleep are described in greater detail below. In general, these TES ensemble waveforms may be monophasic or biphasic (or both during different periods); in particular the sleep-improving TES ensemble waveforms may include biphasic electrical stimulation. This biphasic electrical stimulation may be asymmetric with respect to positive and negative going phases. Sleep-enhancing TES waveforms may also have a duty cycle (e.g., time on relative to time off) of between 10% and 90%, e.g., a duty cycle of between 30% and 60%. The peak amplitude of the applied current may also be controlled. In general, the peak amplitude may be greater than 3 mA (greater than 4 mA, greater than 5 mA, greater than 6 mA, greater than 7 mA, greater than 8 mA, etc. or between about 3 mA and about 30 mA, between 3 mA and 20 mA, between 5 mA and 30 mA, between 5 mA and 20 mA, etc.).

As mentioned above, any of the stimulation parameters (e.g., peak current amplitude, frequency, DC offset, percent duty cycle, capacitive discharge, etc.) may be changed during the ensemble waveform, so that sub-periods of different parameters may be consecutively applied. The frequency may be between 250 Hz and 40 kHz (e.g., a minimum of: 250, 300, 350, 400, 450, 500, 550, 600, 650, 700, 750, 800, 850, 900, 950, 1000, 1500, 2000, 3000, 4000, 5000, etc. Hz and a maximum of 350, 400, 450, 500, 550, 600, 650, 700, 750, 800, 850, 900, 950, 1000, 1500, 2000, 3000, 4000, 5000, 6000, 7000, 8000, 9000, 10000, 12000, 15000, 20000, 25000, 30000, 35000, 40000 Hz, where the minimum is always less than the maximum).

As mentioned, any appropriate stimulation duration may be used. For example, the step of continuing application of the electrical stimulation for a stimulation duration may include continuing for a stimulation duration of at least five minutes.

Any of the TES ensemble waveforms described herein may be modulated by amplitude modulation, using an appropriate AM carrier frequency. For example, applying the TES waveform(s) may comprise applying electrical stimulation having amplitude modulation, and the amplitude modulation may generally have a frequency of less than 250 Hz (e.g., between 0.01 Hz and 250 Hz, 1 Hz and 250 Hz, 5 Hz and 200 Hz, 10 Hz and 200 Hz, etc.).

In some variations, applying the TES sleep-improving ensemble waveform may include applying electrical stimulation having a burst mode. A bursting mode may include periods where the applied TES stimulation is quiescent ("off"). Note that although the majority of the examples described herein include the use of ensemble waveforms in which one or more (though often just one) stimulation parameter changes during different, predefined component waveforms that are sequentially applied as the ensemble waveform, in some variations only a single component waveform is applied. Similarly, a component waveform may vary continuously or discretely (by steps) for one or more component waveforms.

For example, described herein are methods of non-invasively reducing sleep onset that may include: placing a first electrode of a wearable transdermal electrical stimulation (TES) applicator on a subject's temple region and a second electrode on a back of the subject's neck; activating the wearable TES applicator to deliver a biphasic electrical stimulation between the first and second electrodes having a duty cycle of greater than 10 percent, a frequency of 250 Hz or greater, and an intensity of 3 mA or greater, wherein the biphasic electrical stimulation is asymmetric with respect to positive and negative going phases; and reducing sleep onset by applying the biphasic electrical stimulation between the first and second electrodes for 10 seconds or longer.

For example, a method of non-invasively inducing sleep in a subject may include: placing a first electrode of a wearable transdermal electrical stimulation (TES) applicator on the subject's skin on the subject's temple region and a second electrode on a back of the subject's neck above a vertebra prominens; activating the wearable TES applicator to deliver a biphasic electrical stimulation having a duty cycle of greater than 10 percent, a frequency of 250 Hz or greater, and an intensity of 3 mA or greater, wherein the biphasic electrical stimulation is asymmetric with respect to positive and negative going phases; and inducing sleep by applying the biphasic electrical stimulation between the first and the second electrodes for 10 seconds or longer.

A method of maintaining sleep in a subject may include: placing a first electrode of a wearable transdermal electrical stimulation (TES) applicator on the subject's skin on the subject's temple region and a second electrode on a back of the subject's neck above a vertebra prominens; activating the wearable TES applicator to deliver a biphasic electrical stimulation having a duty cycle of greater than 10 percent, a frequency of 250 Hz or greater, and an intensity of 3 mA or greater, wherein the biphasic electrical stimulation is asymmetric with respect to positive and negative going phases; and maintaining a state of sleep in the subject by applying the biphasic electrical stimulation between the first and second electrodes for 10 seconds or longer while the subject is asleep.

Any of the method components described above may be incorporated into any of these exemplary methods as well. For example, attaching the TES applicator and/or electrodes may refer to adhesively attaching, mechanically attaching or the like. In general, the TES applicator may be applied directly to the body (e.g., coupling the body to the skin or clothing of the patient directly) or indirectly, e.g., attaching to the body only by coupling with another member (e.g., electrode) that is already attached or attachable to the body.

In any of the methods described herein, the user may be allowed and/or required to select the waveform ensemble from a list of possible waveform ensembles, which may be labeled to indicate name, content, efficacy, and/or the like. As already mentioned, the subject may be permitted or allowed (e.g., using a wearable electronic and/or handheld electronic apparatus) to select and/or modify one or more parameters for the electrical stimulation to be applied, wherein the parameters may include one or more of: stimulation duration, frequency, peak amplitude, and duty cycle.

The electrodes and TES applicator may be worn while the subject sleeps, or removed prior to sleeping. For example, any of these methods may include removing the first and second electrodes and TES applicator prior to the subject sleeping.

In general, reducing sleep onset or inducing sleep may include: increasing drowsiness and/or increasing the desire to sleep. Activating may include delivering the biphasic electrical stimulation while the subject is awake. Thus, in any of these methods described herein, the method may include monitoring the subject's sleep. As mentioned, sleep may be monitored using the wearable TES applicator and/or using a separate monitor. For example, monitoring the subject's sleep may be done using the wearable TES applicator having a sensor coupled to the TES applicator to measure the subject's autonomic function, or communicating with the TES applicator (but separate). Monitoring may include one or more of: actimetry, galvanic skin resistance, heart rate, heart rate variability, or breathing rate. Monitoring may include monitoring the subject's sleep using a sensor that is worn by the subject, coupled to the subject's bed, or remotely monitoring the subject without physical contact with the subject.

Any of the methods described herein may be automatically or semi-automatically controlled, and may include processing of feedback from any of the sensors to regulate the application of TES, including modifying one or more TES waveform parameter based on the sensed values. For example, any of these methods may include automatically stopping activation of the wearable TES applicator when the subject is asleep based on a physiological measurement or sleep state monitoring, and/or automatically stopping activation of the wearable TES applicator when the subject is asleep following a fixed delay (e.g., 1 min, 2 min, 3 min, 4 min, 5 min, 6 min, 7 min, 8 min, 9 min, 10 min, 15 min, 20 min, etc.). Activating may include activating the wearable TES applicator when the subject is asleep based on a physiological measurement or sleep state monitoring.

Any of the methods described herein may be methods to treat a sleep disorder or a sleep-related disorder. For example, any of these methods may include a step of treating a sleep disorder in the subject. Examples of such sleep disorders include: idiopathic hypersomnia, insomnia, post-traumatic stress disorder, anxiety, emotional distress, depression, bipolar disorder, schizophrenia; restless leg syndrome and periodic limb movement disorder; circadian rhythm disorders; sleeping sickness; parasomnia; shift work and jet lag; and hypersomnia.

In any of these variations, the apparatus may be specifically adapted for comfort, convenience or utility during and before sleeping. For example, in apparatuses in which there is a visible (e.g., light) indicator such as an LED, screen, or the like, the light may be dimmed or turned off during operation and/or following operation, and/or when sleep is detected. For example, any of these methods may include dimming or turning off a visual indicator (e.g., an LED or screen) of the transdermal electrical stimulator when the wearable TES system is activated.

Although the stimulation parameters may be adjusted or modified by the subject wearing the apparatus, any of these method may include modifying, by a party that is not the subject, a stimulation parameter of the wearable TES device while the subject is sleep, wherein the stimulation parameter includes one or more of: stimulation duration, frequency, peak amplitude, duty cycle, capacitive discharge, DC offset, etc.

As mentioned, the apparatus and methods may also be adapted to automatically adapt stimulation parameters. For example, any of these methods may include automatically modifying a stimulation parameter of the wearable TES device based on the subject's sleep quality being below a threshold value, where sleep quality is defined by one or more of: sleep latency, amount and/or sequence of sleep stages, sleep amount, autonomic state, EEG activity, EMG activity, movements, and time during the day when sleep occurs, further wherein the stimulation parameter includes one or more of: stimulation duration, frequency, peak amplitude, duty cycle, capacitive discharge, DC offset, etc.

Any of these methods may also include automatically stopping, starting or modulating the wearable TES applicator based on a measure of sleep quality detected from the subject, where sleep quality is defined by one or more of: sleep latency, amount and/or sequence of sleep stages, sleep amount, time during the day when sleep occurs, and other sleep quality or quantity metric. The sleep quality used to start, stop, or modulate the transdermal electrical stimulation may be based on a measurement of one or more of the subject's: activity, stress, immune system function, autonomic state, or other physiological assessment.

Placing may comprise placing the first and second electrodes before or during a nap.

In operation, the wearable TES applicator may automatically or manually triggered to deliver the biphasic electrical stimulation when the subject wakes up. The apparatus may also be configured to transmit a notification (directly or via a user computing device) that reminds the subject to wear the TES applicator before bed, for example, transmitting a notification that reminds the subject to wear the TES applicator before bed based on input from a location sensor in the TES applicator or wirelessly connected to the TES applicator that detects when the subject is in their bedroom.

The methods described herein may also include providing a metric to the subject showing a sleep quality metric, wherein the sleep quality metric is one or more of: sleep onset time, length of sleep, sleep latency, total length or percentage of REM sleep, total length or percentage of NREM sleep, total length or percentage of slow wave (deep) sleep, length of sleep cycles, number and/or length of night awakenings, and morning wake time.

Any of the methods described herein may include automatically adjusting the biphasic electrical stimulation based on an average or detected amount of time before the subject falls asleep. The devices described herein may also be configured to perform any of these steps such as automatically adjusting the electrical stimulation.

In addition, any of the methods described herein may also include concurrently delivering a calming sensory stimulus when activating the wearable TES applicator, such as concurrently delivering a calming sensory stimulus when activating the wearable TES applicator, wherein the calming sensory stimulus is one or more of auditory stimulus, olfactory stimulus, thermal stimulus, and mechanical stimulus.

Also described herein are wearable transdermal electrical stimulation (TES) applicators for facilitating, inducing, and/or maintaining sleep in a subject. These apparatuses may be configured to perform any of the methods described herein. In general, these apparatuses may include: a body; a first electrode; a second electrode (the apparatuses may be part of a separate but attachable, e.g., disposable, electrode assembly that couples to the body); and a TES control module at least partially within the body. The TES control module may include a processor, a timer and a waveform generator, and the TES control module may be adapted to deliver an electrical (e.g., biphasic, asymmetric) stimulation signal for a stimulation duration (e.g., 10 seconds or longer) between the first and second electrodes. The electrical stimulation which may be a TES ensemble waveform, may have a duty cycle of greater than 10 percent, a frequency of 250 Hz or greater, and an intensity of 3 mA or greater, wherein the biphasic transdermal electrical stimulation is asymmetric with respect to positive and negative going phases. The wearable TES applicator may generally be lightweight (e.g., may weigh less than 50 grams, etc.). Any of the TES applicators described herein may include at least one sensor coupled to the body for sleep monitoring of the subject.

Any appropriate sleep-enhancing TES waveform(s) may be used. For example, the duty cycle may be between 10% and 90%. The transdermal electrical stimulation may have a frequency greater than 250 Hz, 500 Hz, 750 Hz, 5 kHz, etc. The transdermal electrical stimulation may comprise amplitude modulation, as discussed above, having a frequency of less than 250 Hz. The transdermal electrical stimulation may include a burst mode, such as a burst mode having a frequency of bursting that is less than 250 Hz.

Any of the apparatuses described herein may be specifically adapted for sleep, as mentioned above. In some variations this may include having the TES waveform(s) pre-programmed, and/or including feedback for monitoring the subject's sleep, and/or for using any sleep-related data on the subject in modifying/controlling the applied stimulation. The apparatus may include at least one sensor that measures the subject's autonomic function, wherein the measurement of autonomic function may measure one or more of: galvanic skin resistance, heart rate, heart rate variability, or breathing rate. The at least one sensor may comprise a sensor to detect the subject's movements (e.g., uniaxial or multi-axial accelerometer, etc.). A movement sensor may be configured to detect the subject's movements in communication with the controller; the movement sensor may be worn by the subject, coupled to the subject's bed, or may detect movements remotely without direct or indirect physical contact with the subject.

The TES control module may be configured to automatically stop delivery of the biphasic electrical stimulation when the subject is asleep based on a measurement from a sensor, for example, when the subject is asleep at a fixed delay (e.g., 1 min, 2 min, 3 min, 4 min, 5 min, 6 min, 7 min, 8 min, 9 min, 10 min, 12 min, 15 min, 30 min, 45 min, 1 hr, etc.).

The TES control module ("TES controller") may be configured to automatically start delivery of the biphasic electrical stimulation when the subject is asleep based on a physiological measurement derived from the at least one sensor.

Any of these devices may include a visual indicator (e.g., light, screen, etc., including LED(s), displays, etc.) that is configured to be turned down or turned off when the wearable TES system is activated.

The TES controller may also be configured to automatically stop, start or modify delivery of the biphasic electrical stimulation based on sleep quality being below a threshold value, wherein sleep quality is defined by a TES control module (or computing device communicatively connected to the TES control module) based on data from the at least one sensor and correspond to one or more of: sleep latency, amount and/or sequence of sleep stages, sleep amount, and time during the day when sleep occurs. The TES controller may also be configured to automatically or manually deliver the biphasic electrical stimulation if the subject wakes up.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 3B-3G illustrate another example of a neurostimulator as described herein.

FIGS. 11A-11C show heart rate variability (HRV) power in very low, low, and high frequency bands, respectively. Changes in heart rate variability may indicate modulation of the subject's autonomic nervous system. In these experiments, comparing between the two effective stimulation regimes (low F and high F), 10 subjects (n=10) were examined.

FIGS. 12A-12C illustrate anxiety, depression and stress, respectively, from patients (n=10) treated as shown above in FIG. 9. The measures are based on the DASS (Depression, Anxiety and Stress Scale), a clinical measure between 0 and 3.

FIGS. 12D-12G illustrate positive affectivity (FIG. 12D), negative affectivity (FIG. 12E), irritability (FIG. 12F), and fatigue (FIG. 12G) in the same patients described in FIGS. 12A-12C. Affectivity was measured on 5 point scale (FIGS. 12D and 12E), irritability was measured on a 0 to 3 scale (FIG. 12F) and fatigue was measured on a 0 to 10 scale (FIG. 12G).

FIGS. 13A and 13B illustrate a comparison between different (effective) sleep enhancing stimulation protocols on the number of naps (FIG. 13A) and in-the-moment stress (FIG. 13B).

FIGS. 14A and 14B compare measures of morning amylase and morning cortisol, respectively between different sleep-enhancing stimulation protocols. Both protocols are significantly different compared to baseline (not shown) and may be different from each other, consistent with the results shown in FIGS. 9-13B (amylase: p=0.036; cortisol: p=0.040). Morning saliva was assayed within 30 minutes of waking for each patient. There were no differences between patients in afternoon or evening cortisol.

FIG. 15A is a table with waveform parameters of another example of a "high F" ensemble waveform as described herein.

FIG. 15B is a table with another variation of an ensemble waveform similar to that shown in FIG. 15A.

FIG. 15C is a table with another variation of an ensemble waveform as shown in FIGS. 15A-15B.

FIG. 16 is a table showing another example of an ensemble waveform that may be adapted for use as a sleep enhancing TES waveform. This variation is consistent with the low F ensemble waveform described herein.

FIG. 17 is a table illustrating one example of a very low F ensemble waveform as described herein.

FIGS. 18A and 18B show experimental designs implemented for testing the effects of nightly repeated, self-administered transdermal electrical neuromodulation of trigeminal and cervical nerve sensory afferents on sleep and mood as described herein.

In FIG. 19A, depression, anxiety and stress are illustrated, while FIG. 19B shows exemplary effects on refreshment and drowsiness.

FIG. 20 is a table summarizing results from a first experiment illustrating the effects of nightly TEN on morning arousal, affect, and mental health.

FIG. 21 is a table summarizing results from a second experiment illustrating impact of nightly TEN and sham treatment on morning arousal, affect, and sleep quality compared to baseline nights.

In FIG. 22A, effects on depression and anxiety are compared. FIG. 22B illustrate effects on stress and sleep time.

FIGS. 24A and 24B are actigraphy graphs showing that TEN significantly improves sleep quality. FIG. 24A shows number of wakeups, WASO (min), and % time awake. FIG. 24B shows RR (msec), RMSDD and pLF.

FIGS. 25A-25C illustrate low-frequency TEN improves the efficacy of trigeminal and cervical afferent modulation for improving sleep quality. FIG. 25A shows the effect on number of wakeups, WASO (min), and % time awake, FIG. 25B shows the DASS and FIG. 25C shows the effect on waking cortisol and morning sAA.

DESCRIPTION OF THE INVENTION

Figure 1:
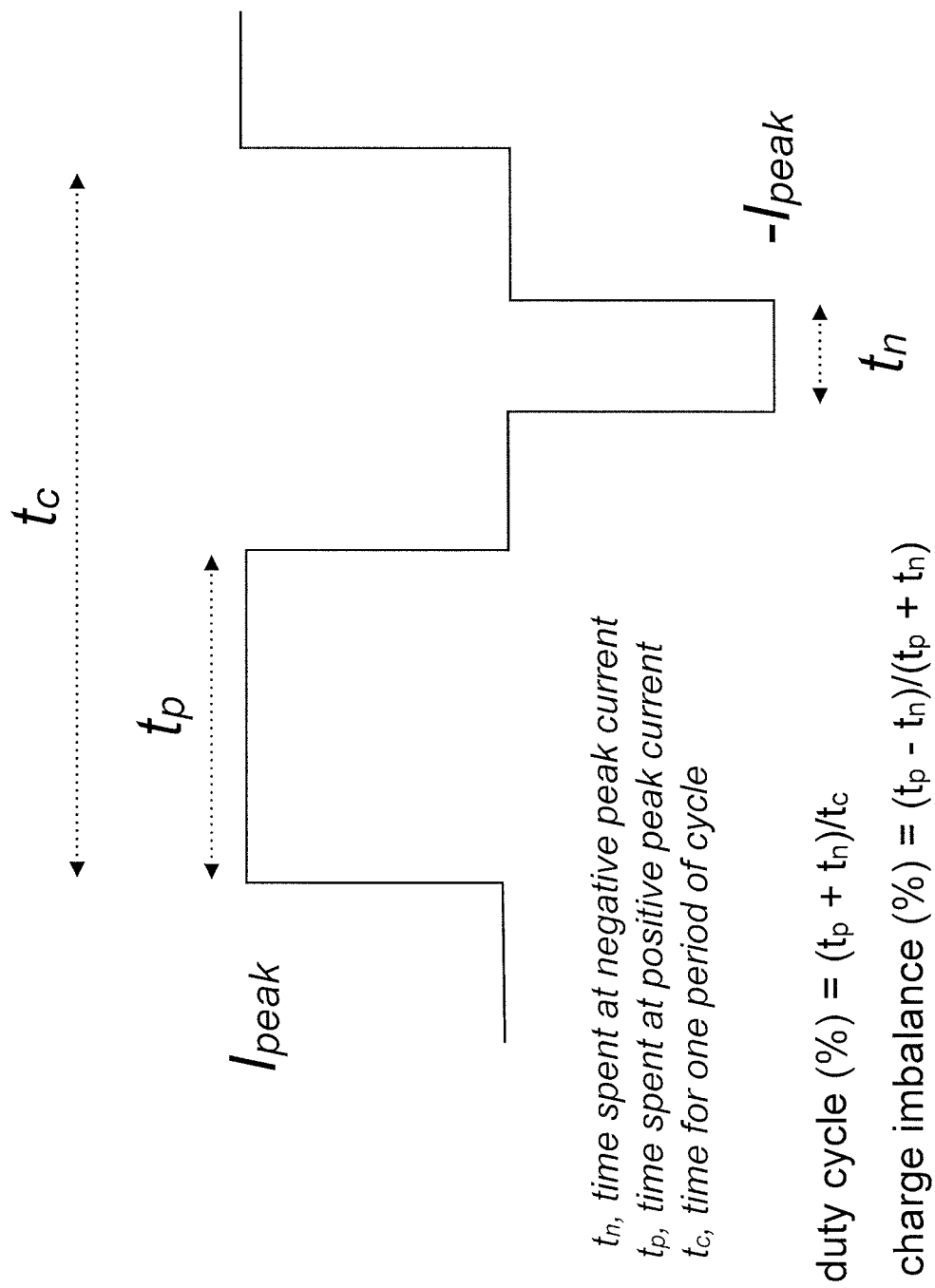
FIG. 1 schematically illustrates a base waveform which may be repeated and modified according to waveform parameters to form component waveforms which may be combined to form ensemble waveforms, as described herein.

In general, described herein are methods and apparatuses (devices and systems) for transdermal electrical stimulation (TES) to enhance sleep, including reducing sleep onset (e.g., increasing drowsiness, reducing sleep onset latency, and inducing sleep) and/or increasing the duration and/or quality of sleep in a subject. The quality of sleep may be related to the length and/or proportion of one or more sleep stages during a subject's sleeping session. In particular, as described herein, the TES may be applied during and/or immediately prior to (e.g., within 30 min, 25 min, 20 min, 15 min, 10 min, 5 min, etc.) a desired sleep time, such as when the subject is preparing or has prepared to sleep (e.g., lying down, etc.). The stimulation parameters of the applied TES (duration, amplitude, frequency, percent duty cycle, bipolar/unipolar, DC offset, AC component/AC frequency, presence of capacitance discharge, etc.) and location of stimulation on the subject (attachment site of the electrodes) as well as the function and feel of the TES applicator (weight, placement, and shape of the applicator) may affect the efficacy with respect to enhancing sleep, and are described herein.

As will be described in greater detail below, particular ranges of stimulation parameters (frequency, peak current amplitude, duty cycle) of TES waveforms applied using a wearable TES applicator worn on the subject's head and/or neck have been found to be effective, while stimulation outside of these parameters, and/or at different locations, may not be as effective. In general, stimulation at greater than 10% duty cycle (e.g., between 10 and 90%, between 20 and 80%, between 30 and 80%, etc.), at a frequency that is 100 Hz or greater (e.g., 150 Hz or greater, 200 Hz or greater, 250 Hz or greater, 300 Hz or greater, 400 Hz or greater, 500 Hz or greater, 600 Hz or greater, 700 Hz or greater, 750 Hz or greater, 800 Hz or greater, 1 kHz or greater, 2 kHz or greater, 5 kHz or greater, etc., and in particular, 250 Hz or greater), and a peak amplitude of 3 mA or greater (e.g., 4 mA or greater, 5 mA or greater, 6 mA or greater, 7 mA or greater, 8 mA or greater, 9 mA or greater, 10 mA or greater, etc.) are particularly effective. Because such stimulation parameters (e.g., low frequency at relatively high peak current amplitudes) may be painful and thus prevent drowsiness or sleep, it may be particularly useful to modulate the applied TES so that it can be comfortably tolerated, even before sleeping. For example, the applied TES waveform may be biphasic and in some variations asymmetric, with respect to positive and negative going phases. In some variations a capacitive discharge (e.g., a rapid depolarization component to discharge capacitance built up on the electrodes (and in the body) may be applied during the pulsed application (e.g., on each or a subset, e.g., during positive going pulses, negative pulses, etc., of the TES stimulation)).

Particular types of TES waveforms delivered to a subject (e.g., to the head and/or neck) may improve the quantity and quality of sleep. In such cases, users wake up feeling more rested, with a more positive mood, less anxiety, and less stress (both as self-reported and as assessed by biochemical assay of saliva). For example, 15 minute TES waveforms delivered through a wearable TES applicator attached with an anode at the forehead/temple area and cathode on the neck of a subject (delivering a pulsed waveform with variable frequency, generally between 250 Hz and 11 kHz at between 2-12 mA peak current in asymmetric, biphasic pulses) showed a significant improvement in sleep, e.g., reducing sleep onset (time to fall asleep), duration (lengthening the duration of sleep) and quality (e.g., self-reported assessments) of subject's sleep compared to baseline or to non-effective (sham) TES waveforms.

Described herein are methods and apparatuses for transdermal electrical stimulation (e.g., neurostimulation) using TES stimulation protocols and electrode configurations that facilitate the passage into sleep, accelerate the induction of sleep, improve the restorative quality of sleep, and/or enhance the likelihood of maintaining a state of sleep in a subject. Apparatuses described herein may generally include a neurostimulator for delivering transdermal electrical stimulation, appropriate dermal electrodes that connect electrically to the neurostimulator for transmitting the electrical stimulation to the subject, and, optionally, a controller unit that may be connected to the neurostimulator in a wired or wireless manner (including user computing devices such as a smartphone, tablet, wearable device (e.g. smartwatch or Google Glass), or computer). The TES apparatuses for improving sleep described herein are configured to deliver appropriate TES waveforms and to couple transdermal electrodes with an appropriate configuration for inducing a drowsy or sleeping state in a subject. Methods for improving sleep in a subject (e.g., one or more of: reducing sleep onset, facilitating the passage into sleep, inducing sleep, enhancing the likelihood of maintaining sleep, modifying the quality of sleep, etc.) using a TES system before or during sleep are described. Also described herein are wearable TES apparatuses (e.g., neurostimulators) that are configured specifically to enhance sleep.

These neurostimulators may be capable of autonomous function and/or controllable via a wired or wireless connection to a computerized user device (e.g. smartphone, tablet, laptop, other wearable device). The neurostimulator may be configured specifically to deliver stimulation within a range of parameters, including intensity and frequency, determined to be effective for inducing, enhancing, or promoting sleep while minimizing pain and discomfort due to the relatively large magnitude stimulation provided. For example, an apparatus (such as a TES applicator) may include a control module having circuitry (e.g., hardware), software and/or firmware that allows the apparatus to apply signals within an effective range, including, for example, one or more processors, timers, and waveform generators.

Relative to existing systems for transdermal electrical stimulation for improving sleep, the systems and methods described herein induce more powerful effects for treating and affecting (not limited to treatment or diagnosis of any medical condition) sleep. These apparatuses may use replaceable, disposable (e.g., consumable) electrodes and may also use appropriate electrical stimulation parameters; this combination may mitigate discomfort, enabling higher peak currents to be delivered for stimulating transdermally without delivering irritating or painful stimuli that may wake a subject. Higher peak currents typically provide a more robust effect.

A neurostimulation system as described herein may include two or more parts: (1) a lightweight (e.g., less than 100 g, less than 75 g, less than 50 g, less than 40 g, less than 30 g, less than 25 g, less than 20 g, etc.), wearable (or portable), neurostimulator device (neurostimulator) that is configured to be worn on a subject (generally on the head or neck) or portable and coupled to the subject and includes processor(s) and/or controller(s) to prepare the TES waveform(s) to be applied; and (2) a consumable/disposable electrode assembly to deliver the TES waveform(s) to the wearer. In some variations a third component may be a controller that is separate from but communicates with the neurostimulator. For example, in some variations the controller may be a user device that wirelessly communicates with the neurostimulator. In some variations the controller is a mobile telecommunications device (e.g., smartphone or tablet) being controlled by an application that sends instructions and exchanges 2-way communication signals with the neurostimulator. For example, the controller may be software, hardware, or firmware, and may include an application that can be downloaded by the user to run on a wireless-connectable (e.g., by Bluetooth) device (e.g., smartphone or tablet) to allow the user to select the waveforms delivered by the neurostimulator, including allowing real-time or short latency (e.g., less than one second, less than 500 ms, etc.) modulation of the delivered neurostimulation to enhance sleep as described herein. Alternatively, the electrodes may be reusable and integrated in a single assembly with a TES controller.

The methods and apparatuses described herein may induce a calm or relaxed mental state and may facilitate, induce, or maintain a state of sleep in a subject. This class of cognitive effects includes those associated with relaxation and a calm mental state, for example: a state of calm, including states of calm that can be rapidly induced (e.g., within about 5 minutes of starting delivery of the TES waveforms). In some variations, these effects may include a care-free state of mind; a mental state free of worry; induction of sleep; a slowing of the passage of time; enhanced physiological, emotional, or and/or muscular relaxation; enhanced concentration; inhibition of distractions; increased cognitive and/or sensory clarity; a dissociated state; a state akin to mild intoxication by a psychoactive compound (i.e. alcohol); a state akin to mild euphoria induced by a psychoactive compound (i.e. a morphine); the induction of a state of mind described as relaxed and pleasurable; enhanced enjoyment of auditory and visual experiences (i.e. multimedia); reduced physiological arousal; increased capacity to handle emotional or other stressors; a reduction in psychophysiological arousal as associated with changes in the activity of the hypothalamic-pituitary-adrenal axis (HPA axis) and/or reticular activating system and/or by modulating the balance of activity between the sympathetic and parasympathetic nervous systems generally associated with a reduction in biomarkers of stress, anxiety, and mental dysfunction; anxiolysis; a state of high mental clarity; enhanced physical performance; promotion of resilience to the deleterious consequences of stress; a physical sensation of relaxation in the periphery (i.e. arms and/or legs); a physical sensation of being able to hear your heart beating, and the like.

More interestingly, in some variations, the TES waveforms may enhance sleep as suggested herein shortly after the session (application of TES) has ended; during the session, sleepiness/relaxation may not be felt, and in fact the application may be mildly uncomfortable. The discomfort may be minimized as described herein, and may be short-lived; once application of these (typically lower frequency) stimulation waveforms has stopped, an enhancement of sleep may be affected.

The apparatuses (systems and devices) and methods described herein allow the reproducible enhancement of sleep, as described herein. The effect resulting from the methods and devices described may depend, at least in part, on the positioning of the electrodes. It may be particularly advantageous with the TES waveform parameters described herein to apply the electrodes on the subject's head, neck and head, or neck and elsewhere on the body other than the head. Described below are three configurations for enhancing sleep. These configurations are exemplary and are not meant to be limiting with regard to configurations that can induce these cognitive effects and thus improve sleep in a subject.

Figures 2A, 2B, 2C, 2D, 2E, 2F:
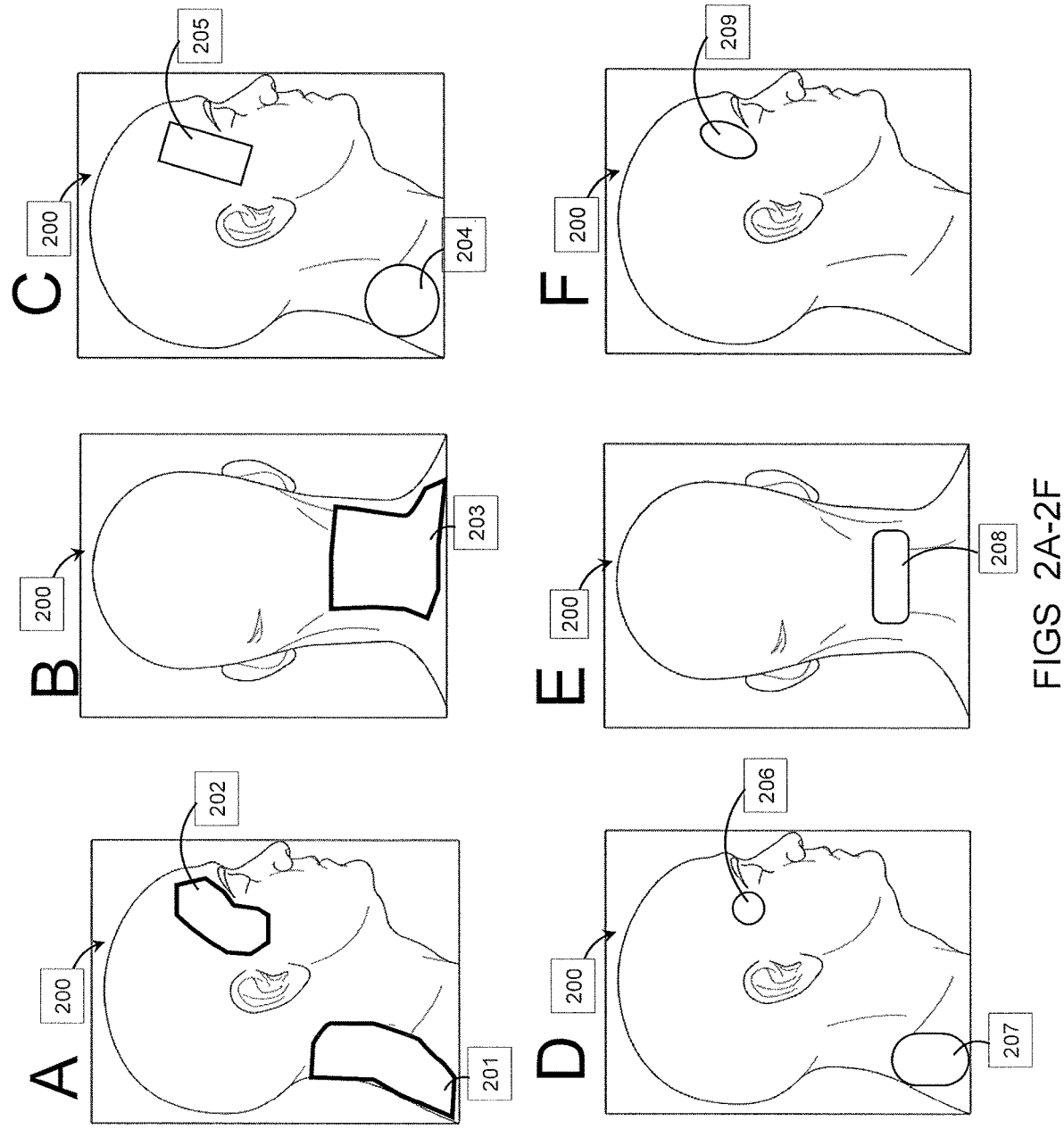
FIGS. 2A-2F show electrode positions for one configuration ("Configuration 3") on a model user head that may be used with the methods and apparatuses of enhancing sleep described herein.

FIGS. 2A-2F illustrate a first electrode configuration for enhancing sleep in a subject 200 and may be referred to herein for convenience as "configuration 3". A first electrode is positioned on the subject's skin near the subject's temple area (e.g., above and slightly to the right of the right eye, or to the left of the subject's left eye) and a second electrode is placed on the subject's neck (e.g., on a superior portion of the neck center as in FIG. 2E). Beneficial embodiments comprise electrodes for the neck having an area of at least about 20 cm$^2$ and an electrode having area at least about 10 cm$^2$ (optimally at least about 20 cm$^2$) near the right temple. TES stimulation of this region may result in enhancing a calm or relaxed mental state. FIGS. 2A and 2B show the broad outlines of effective areas for a temple electrode 202 and neck electrode 201, 203 (though the actual electrodes within these areas would be smaller than the regions outlined). For example, effective electrode size and positions may be as shown in FIG. 2C, wherein rectangular temple electrode 205 and circular electrode (on the right side of the neck) 204 are applied to the subject. In another example of effective electrode size and positions shown in FIG. 2D, a small circular temple electrode 206 and elongated oval electrode (on the right side of the neck) 207 are applied to the subject. In a third example of effective electrode size and positions shown in FIGS. 2E-2F, an oval temple electrode 209 and roughly rectangular electrode (centered on the superior portion of the neck) 208 are applied to the subject.

Figures 4A, 4B, 4C, 4D:
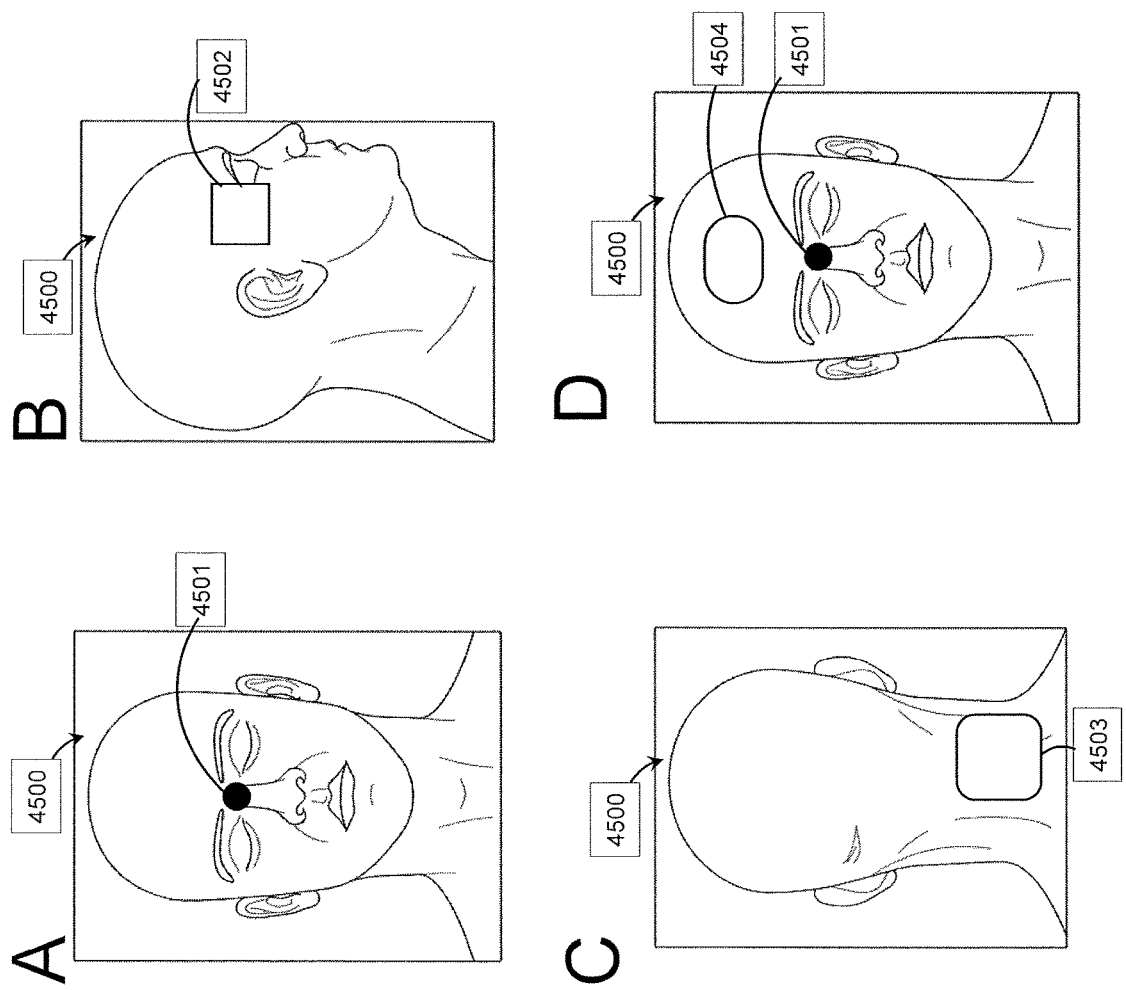
FIGS. 4A-4D show electrode positions for another configuration ("Configuration 4") on a model user head that may be used with the methods and apparatuses of enhancing sleep described herein.

FIGS. 4A-4D illustrate a second electrode configuration for enhancing sleep in subject 4500 and may be referred to herein for convenience as "configuration 4". A first electrode is positioned on the subject's skin near the bridge of the subject's nose 4501 and a second electrode is positioned on the subject's body further than a few inches from the first electrode 4502, 4503, 4504 (e.g., on the subject's head or neck, including the forehead or temple). One advantage of this configuration is that electrode placement is relatively easy for a user to do themselves. FIG. 4A shows model subject 4500 with a round anode electrode placed between the eyes on the bridge of the nose 4501. In a preferred embodiment, the anode electrode is less than 1" across and flexible in order to conform to the curvature of the area near the bridge of the nose of a subject. The anode electrode may be round, elliptical, square, rectangular, or an irregular shape configured for ease of placement on the curved areas of the nose. In a preferred embodiment, a second electrode (e.g., cathode) is located at a site selected from the list including, but not limited to: temple 4502 (as shown in FIG. 4B), forehead 4504 (FIG. 4C), neck 4503 (FIG. 4D), mastoid, shoulder, arm, or elsewhere on the face, head, neck, or body below the neck. A second electrode can be placed on either side of the body. In some embodiments, multiple cathode electrodes can be used. The forehead electrode can be easily affixed using a mirrored surface or front-facing smartphone (or tablet) camera, and the cathode positioning may not need to be precise.

Figures 8A, 8B, 8C, 8D:
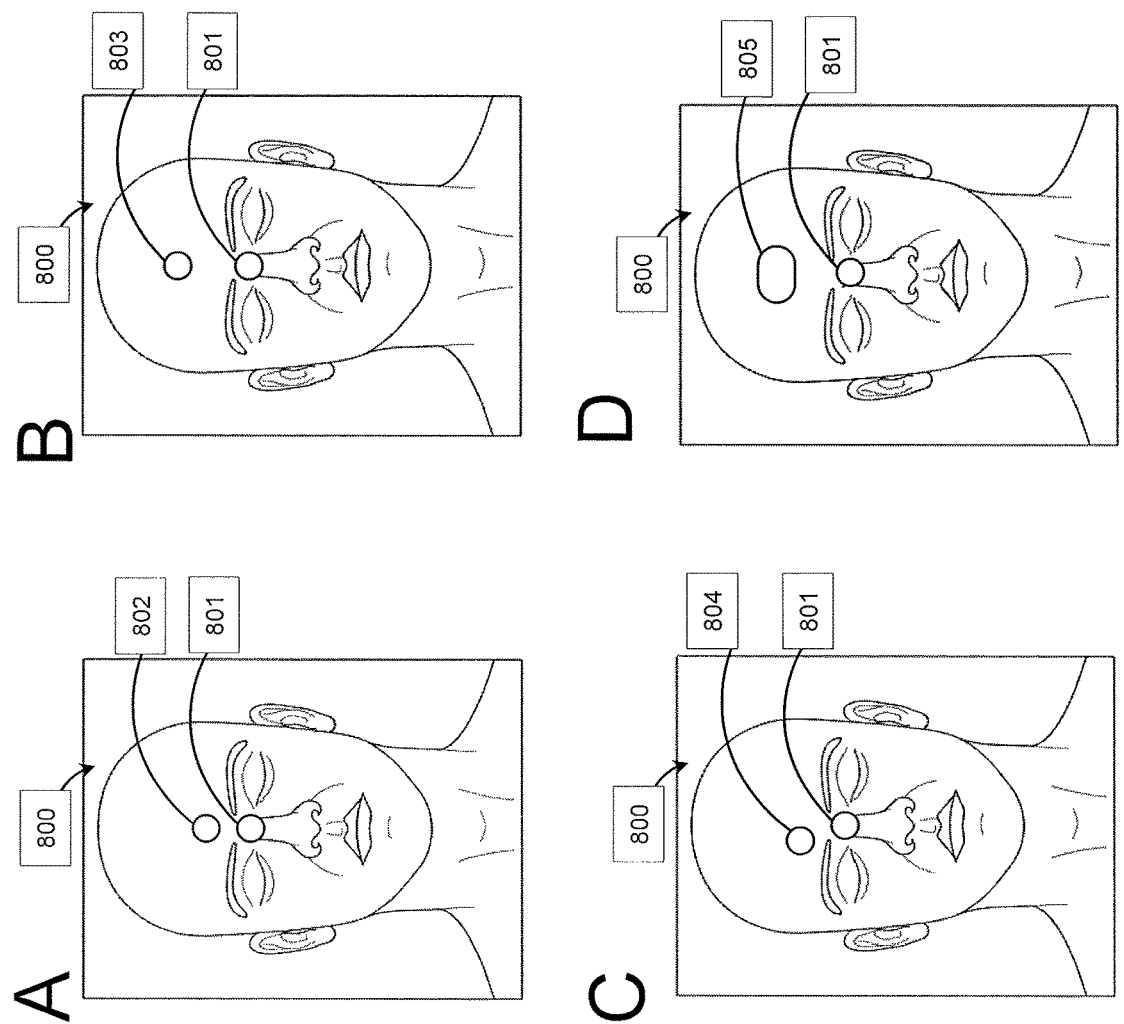
FIGS. 8A-8D show electrode positions for another configuration ("Configuration 6") on a model user head that may be used with the methods and apparatuses of enhancing sleep described herein.

FIGS. 8A-D illustrate a third electrode configuration for enhancing sleep in a subject 800 and may be referred to herein for convenience as "configuration 6". According to an embodiment, subjects treated with TES using Configuration 6 experience different forms of neuromodulation with distinct cognitive effects depending on the waveform and intensity delivered. In embodiments, systems and methods for TES using Configuration 6 electrically couple an electrode to the subject 800 between the eyes at the bridge of the nose 801 ('nasal' electrode) and a second electrode near the midline on the forehead, superior to the nasal electrode. In an embodiment, the nasal electrode is an anode and the forehead electrode is a cathode. The more superior electrode may be medial and close to the bridge of the nose 802 (FIG. 8A), medial and more superior relative to the bridge of the nose 803 (FIG. 8B), shifted left or right relative to the midline and superior to the bridge of the nose 804 (FIG. 8C), or larger and more superior relative to the bridge of the nose 805 (FIG. 8D). In contrast to other configurations, the anode and cathode can be switched and the beneficial neuromodulation effects still achieved in subjects. In a preferred embodiment, systems and methods with this electrode configuration deliver different electrical stimulation waveforms to achieve distinct cognitive effects. TES using an alternating (or pulsed biphasic) transdermal electrical stimulation current at a frequency between 3 kHz and 15 kHz (i.e. between 3 kHz and 5 kHz) at an intensity greater than 4 mA induces neuromodulation in a subject with cognitive effects including, but not limited to, those in the following list: increased drowsiness; increased desire to sleep: induction of sleep; induction of a relaxed state of mind; and induction of a calm state of mind. TES using an alternating transdermal electrical stimulation current at a frequency less than 3 kHz (preferably between 750 Hz and 1 kHz) at an intensity greater than 1 mA induces neuromodulation with cognitive effects including, but not limited to, those in the following list: increased energy and enhanced wakefulness, and is thus not a beneficial set of waveform parameters to use with this configuration for facilitating, inducing, or maintaining a state of sleep.

Alternative electrode configurations for inducing or enhancing sleep include: a first electrode on the neck and a second electrode on the shoulder (i.e. deltoid, upper arm, etc.); one electrode on each shoulder (i.e. deltoid, upper arm, etc.); and two electrodes on the neck.

Figure 7:
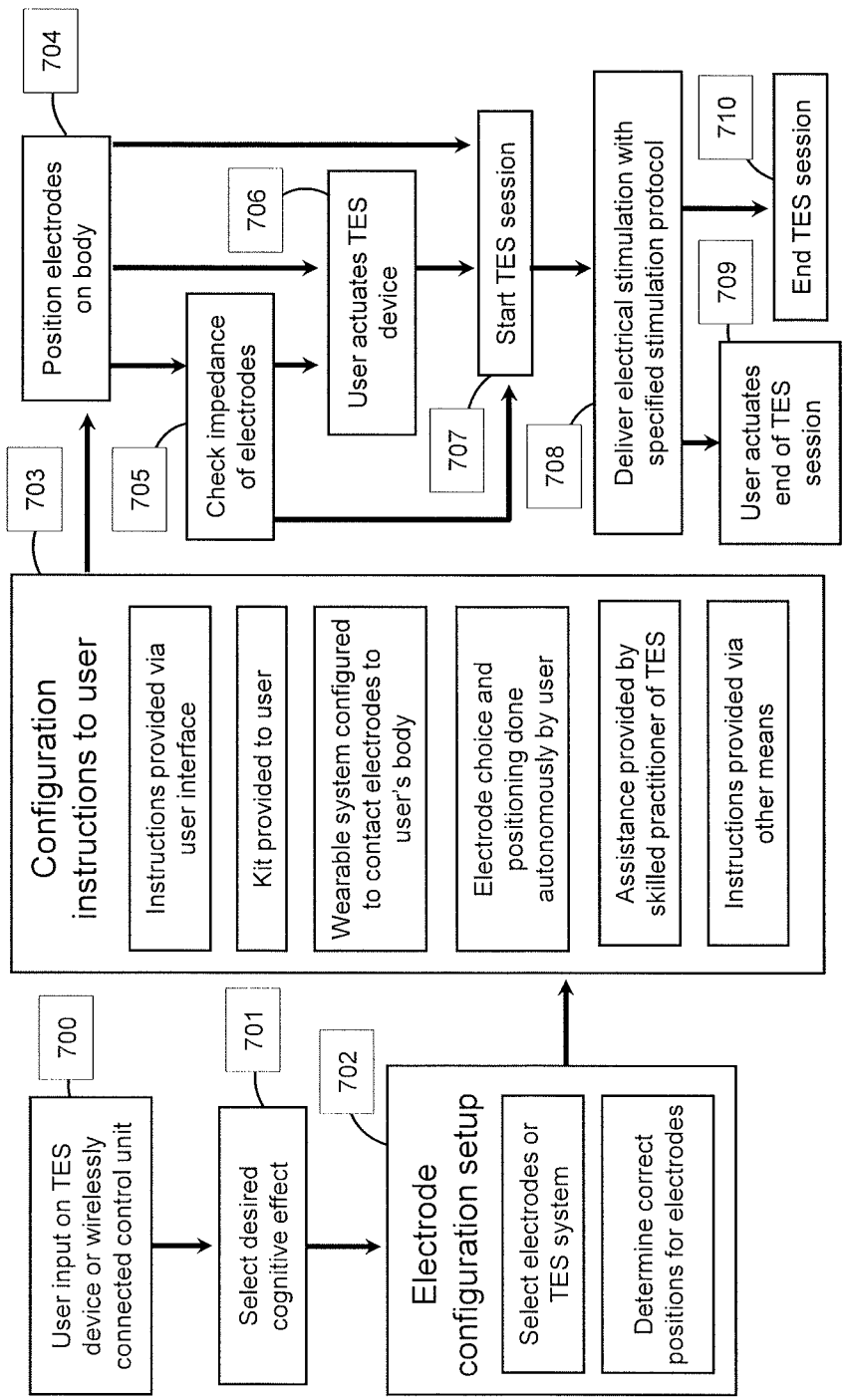
FIG. 7 shows a workflow for configuring, actuating, and ending a TES session.

FIG. 7 shows an exemplary workflow for configuring, actuating, and ending a TES session for improving sleep. According to an embodiment of the present invention, user input on TES device or wirelessly connected control unit 700 is used to select desired cognitive effect 701 which determines electrode configuration setup 702 to achieve the desired cognitive effect, including selection of electrodes or a TES system that contains electrodes and determination of correct positions for electrodes. As described above, configurations 3, 4, and 6 are three exemplar configurations beneficial for improving sleep. In an embodiment, configuration instructions to user 703 are provided by one or more ways selected from the list including but not limited to: instructions provided via user interface; kit provided to user; wearable system configured to contact TES electrodes to appropriate portions of a user's body; electrode choice and positioning done autonomously by user (e.g. due to previous experience with TES); assistance provided by skilled practitioner of TES; and instructions provided via other means.

Based on these instructions or knowledge, a user or other individual or system positions electrodes on body 704. In some embodiments, the TES session starts 707 automatically after electrodes are positioned on the body. In other embodiments, the impedance of the electrodes 705 is checked by a TES system before the TES session starts 707. In some embodiments, after impedance of the electrodes 705 is checked by a TES system, user actuates TES device 706 before the TES session starts 707. In other embodiments, after positioning electrodes on the body 704 the user actuates the TES device 706 to start the TES session 707. Once the TES session starts, the next step is to deliver electrical stimulation with specified stimulation protocol 708. In some embodiments, a user actuates end of TES session 709. In other embodiments, the TES session ends automatically when the stimulation protocol completes 710.

Figure 5:
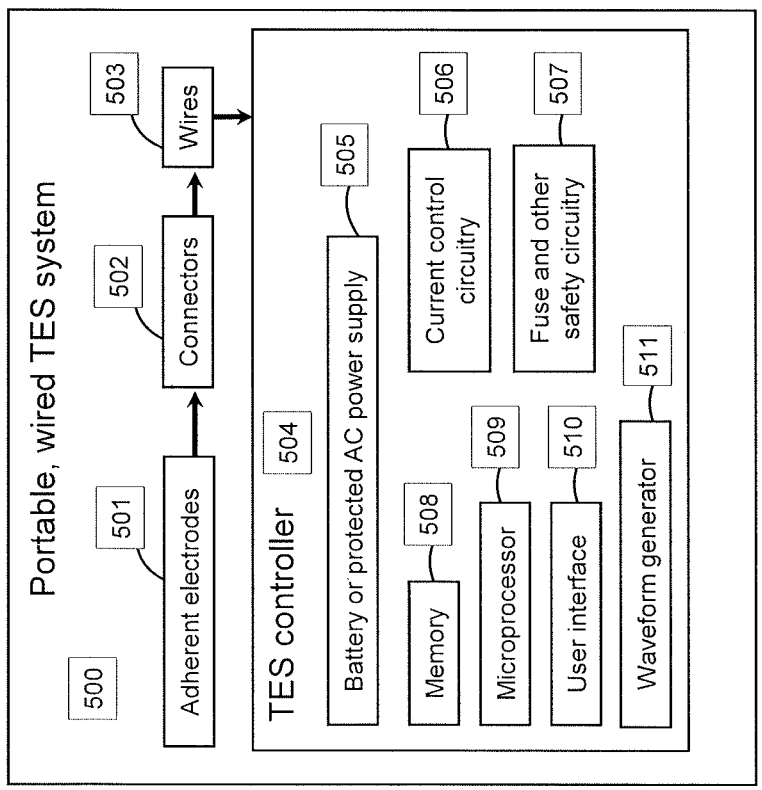
FIG. 5 shows components of a portable, wired TES neurostimulator system.

FIG. 5 shows a schematic illustration of a portable, wired TES neurostimulator 500. According to an embodiment, adherent electrodes 501 connect to TES controller 504 via connectors 502 and wires 503. TES controller 504 has several components including battery or protected AC power supply 505, fuse and other safety circuitry 507, memory 508, microprocessor 509, user interface 510, current control circuitry 506, and waveform generator 511.

Figure 6:
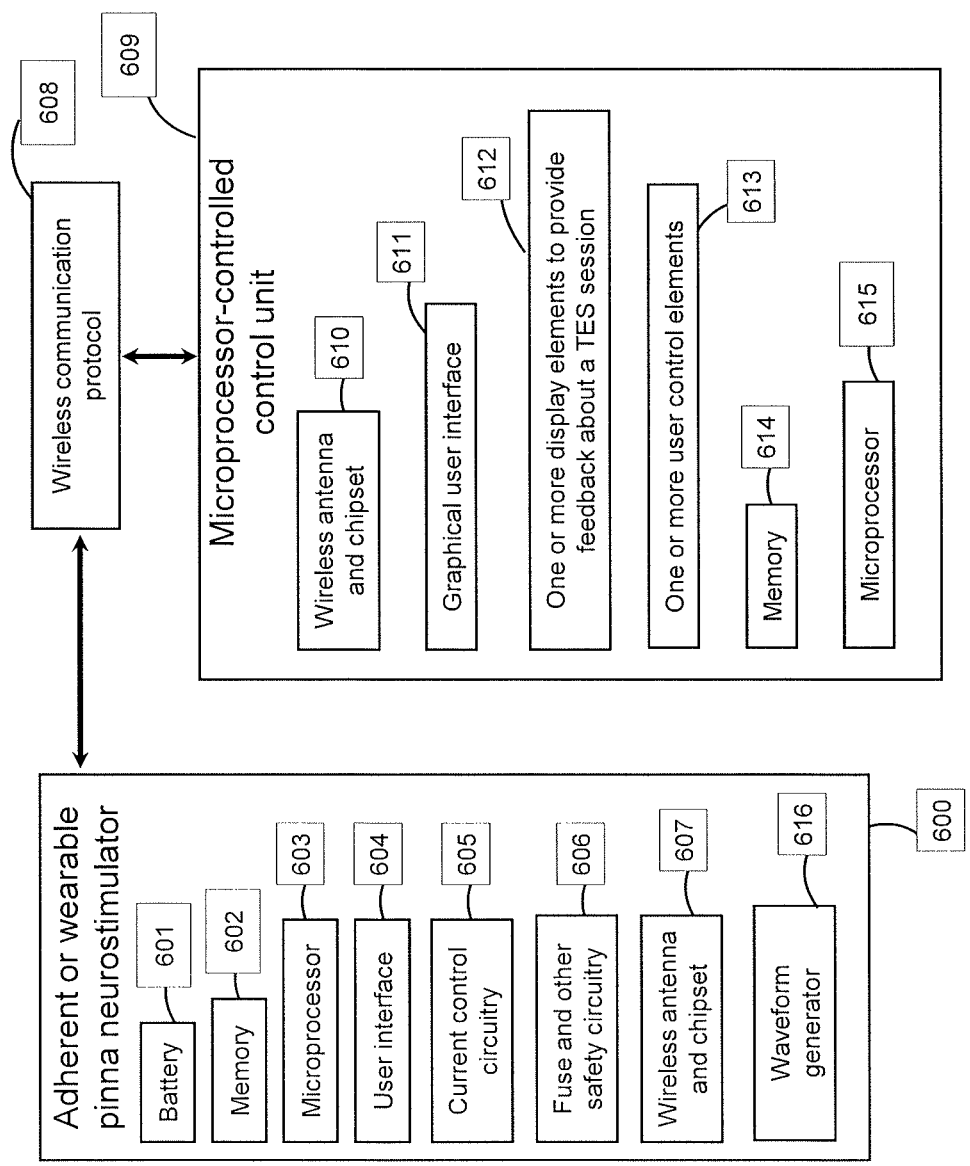
FIG. 6 shows components of a TES neurostimulator system that connects wirelessly to a control unit comprising a microprocessor.

FIG. 6 shows an embodiment of a TES system comprising adherent or wearable TES neurostimulator 600 that communicates wirelessly with microprocessor-controlled control unit 609 (e.g. a smartphone running an Android or iOS operating system such as an iPhone or Samsung Galaxy, a tablet such as an iPad, a personal computer including, but not limited to, laptops and desktop computers, or any other suitable computing device). In this exemplary embodiment, adherent or wearable neurostimulator 600 holds two or more electrodes in dermal contact with a subject with one or more of: an adhesive, a shaped form factor that fits on or is worn on a portion of a user's body (e.g. a headband or around-the-ear 'eyeglass' style form factor). In an exemplar embodiment, adherent or wearable neurostimulator 600 comprises components: battery 601, memory 602, microprocessor 603, user interface 604, current control circuitry 605, fuse and other safety circuitry 606, wireless antenna and chipset 607, and waveform generator 616. Microprocessor-controlled control unit 609 includes components: wireless antenna and chipset 610, graphical user interface 611, one or more display elements to provide feedback about a TES session 612, one or more user control elements 613, memory 614, and microprocessor 66. In an alternate embodiment the neurostimulator 600 may include additional or fewer components. One of ordinary skill in the art would appreciate that neurostimulator could be comprised of a variety of components, and embodiments of the present invention are contemplated for use any such component.

An adherent or wearable neurostimulator 600 may be configured to communicate bidirectionally with wireless communication protocol 608 to microprocessor-controlled system 609. The system can be configured to communicate various forms of data wirelessly, including, but not limited to, trigger signals, control signals, safety alert signals, stimulation timing, stimulation duration, stimulation intensity, other aspects of stimulation protocol, electrode quality, electrode impedance, and battery levels. Communication may be made with devices and controllers using methods known in the art, including but not limited to, RF, WIFI, WiMax, Bluetooth, BLE, UHF, NHF, GSM, CDMA, LAN, WAN, or another wireless protocol. Pulsed infrared light as transmitted for instance by a remote control is an additional wireless form of communication. Near Field Communication (NFC) is another useful technique for communicating with a neuromodulation system or neuromodulation puck. One of ordinary skill in the art would appreciate that there are numerous wireless communication protocols that could be utilized with embodiments of the present invention, and embodiments of the present invention are contemplated for use with any wireless communication protocol.

Adherent or wearable neurostimulators 609 may or may not include a user interface 604 and may be controlled exclusively through wireless communication protocol 608 to control unit 609. In an alternate embodiment, adherent or wearable neurostimulator 609 does not include wireless antenna and chipset 607 and is controlled exclusively through user interface 604. One skilled in the art will recognize that alternative neurostimulator systems can be designed with multiple configurations while still being capable of delivering electrical stimulation transdermally into a subject.

In general, any appropriate neurostimulation system may use (and/or be configured to use or operate with) the ensemble waveforms as described herein for enhancing sleep. FIGS. 3A, and 3B-3M describe and illustrate an example of a neurostimulation system (neurostimulator, electrodes, controller) that may be used. For example, a neurostimulation system may include a lightweight, wearable, neurostimulator device (neurostimulator) that is configured to be worn on the head and a consumable/disposable electrode assembly; in addition a device that may be worn and/or held by the user ("user device") which includes a processor and wireless communication module may be used to control the application of neurostimulation by the wearable neurostimulator. The neurostimulator and/or user device may be particularly adapted to deliver the ensemble waveforms as described herein. For example, the user device may present a list of ensemble waveforms and allow the user to select among them in order to select a desired cognitive effect. The ensemble waveforms may be ordered by the desired effect (e.g., enhancing sleep onset, improving sleep quality, etc.) and/or by time and/or by ranking, etc. Further, the user device may be adapted to communicate with the wearable neurostimulator and may transmit an identifier of the selected ensemble waveform, and/or waveform parameters that define all of a portion (e.g., component waveforms or portions of component waveforms) of the ensemble waveform, as well as any user adjustments such as user modification to the perceived intensity to be used to modify the actual waveforms delivered by, for example, attenuating the ensemble waveform parameters. Thus, for example, the user device may be configured to send, and the neurostimulator to receive, the ensemble waveform parameters (duration, ramping parameter/ramping time, capacitive discharge parameters, current amplitude, frequency, percent duty cycle, percent charge imbalance, etc.).

The user device may also be referred to herein as a controller, and the controller (user device or user computing device) is typically separate from but communicates with the neurostimulator. For example, in some variations the controller may be a user device that wirelessly communicates with the neurostimulator. In some variations the controller is a mobile telecommunications device (e.g., smartphone or tablet) or wearable electronics (e.g., Google glass, smart watch, etc.), being controlled by an application that sends instructions and exchanges 2-way communication signals with the neurostimulator. Any of these embodiments may be referred to as handheld devices, as they may be held in a user's hand or worn on the user's person. However, non-handheld control user devices (e.g., desktop computers, etc.) may be used as well. The user device may be a general purpose device (e.g., smartphone) running application software that specifically configures it for use as a controller, or it may be a custom device that is configured specifically (and potentially exclusively) for use with the neurostimulators described herein. For example, the controller may be software, hardware, or firmware, and may include an application that can be downloaded by the user to run on a wireless-connectable (i.e. by Bluetooth) device (e.g., handheld device such as a smartphone or tablet) to allow the user to select the waveforms delivered by the neurostimulator, including allowing real-time modulation of the delivered neurostimulation to modify the user's cognitive state as described herein.

The neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., >3 mA, greater than 4 mA, greater than 5 mA, between 5 mA and 40 mA, between 5 mA and 30 mA, between 5 mA and 22 mA, etc.), and a frequency of >100 Hz (e.g., between 750 Hz and 25 kHz, between 750 Hz and 20 kHz, between 750 Hz and 15 kHz, etc.), the current is typically biphasic and is charge imbalanced, and has a duty cycle of between 1-90% (e.g., between 10-90%, between 30-80%, between 30-60%, etc.). One or more of these characteristics may be changed during stimulation over timescales of every few seconds to minutes as the ensemble waveform shifts between subsequent component waveforms.

Figure 3A:
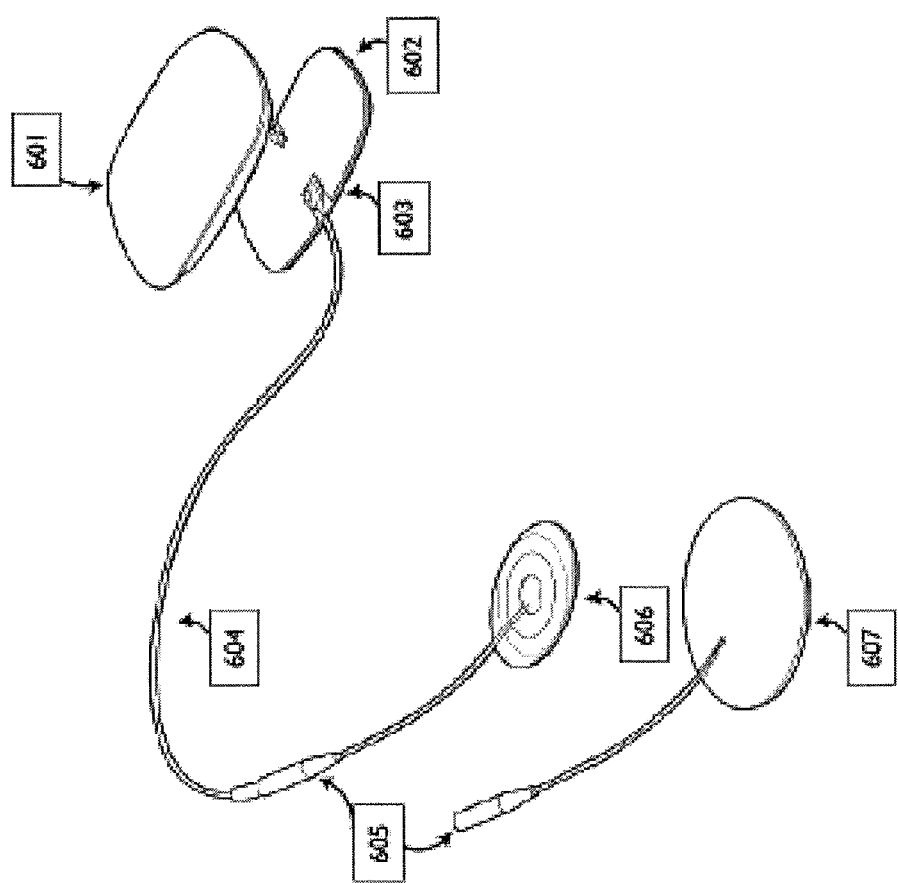
FIG. 3A illustrates one example of a neurostimulator that may be configured for use with (and may deliver) the ensemble waveforms described herein.
Figure 3H:
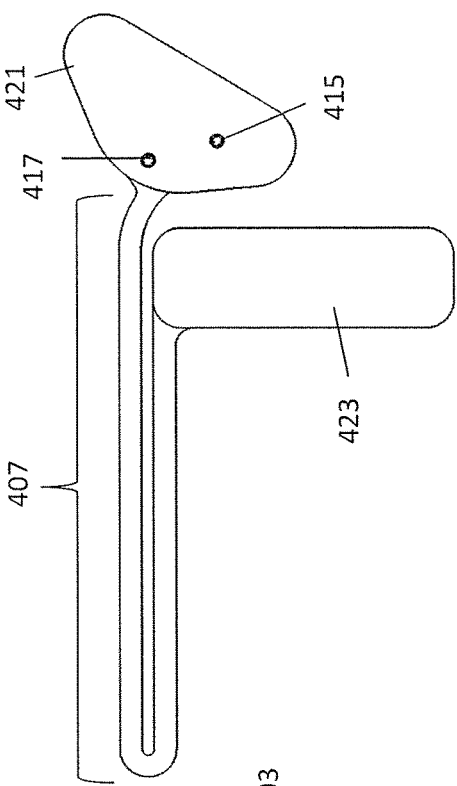
FIGS. 3H-3K illustrates a first example of one variation of an electrode assembly.
Figure 3J:
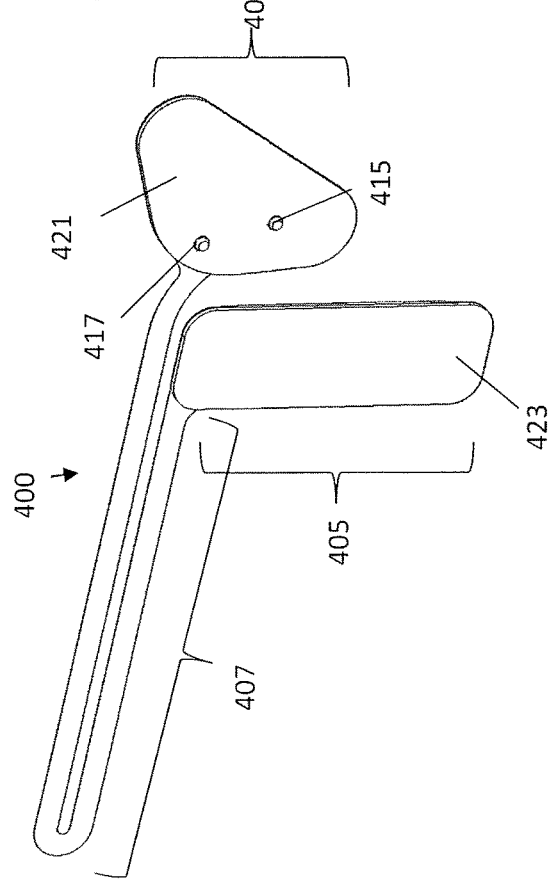
Figure 3I:
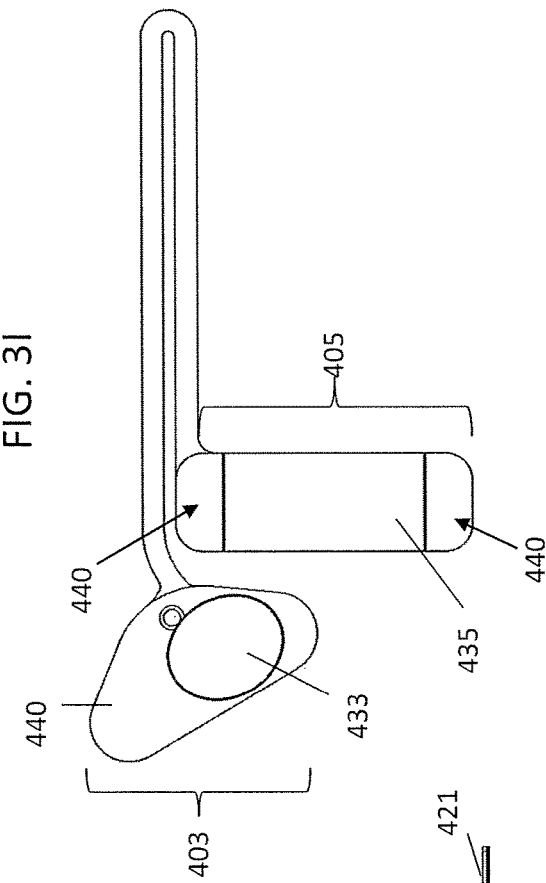
Figure 3K:
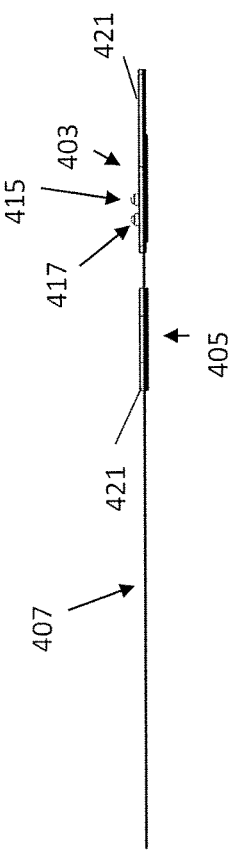
Figure 3M:
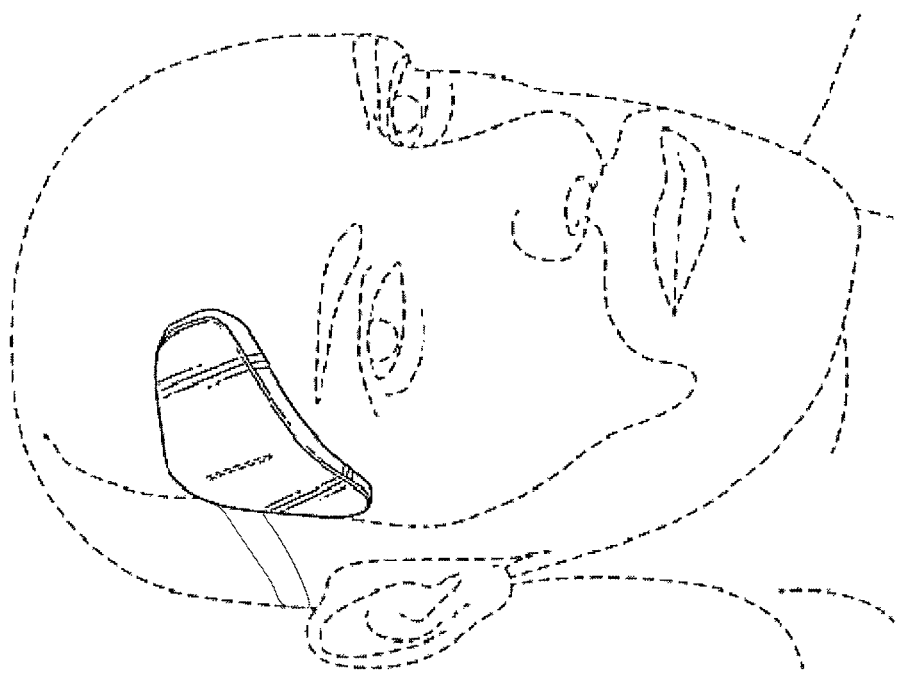
FIG. 3M illustrates the neurostimulator device worn on the subject's head.

When worn, the system may resemble the system shown in FIG. 3M, having an electrode assembly attached at two locations (points or regions) on the subject's head and/or neck) and a neurostimulator attached to the electrode assembly, as shown; in some variations a separate controller may be attached to coordinate the application of stimulation.

As will be described in greater detail herein, the neurostimulator may be lightweight (e.g., less than 30 g, less than 25 g, less than 20 g, less than 18 g, less than 15 g, etc.), and self-contained, e.g. enclosing the circuitry, power supply, and wireless communication components such as a rechargeable battery and charging circuit, Bluetooth chip and antenna, microcontroller, and current source configured to deliver waveforms with a duration of between 10 seconds and tens of minutes. A neurostimulator may also include safety circuitry. The neurostimulator may also include circuits to determine that the electrode is attached and what "kind" of electrode it is (i.e., for configuration 3 vs. configuration 4; or indicating the batch and/or source of manufacture, etc.). FIGS. 3A and 3B-3G illustrate two variations of a neurostimulator.

For example, FIG. 3A illustrates a first example of a neurostimulator as described herein. In FIG. 3A, the neurostimulator is shown with a pair of electrodes attached. A first electrode 601 is coupled directly to the body 603 of the TES applicator 602, and a second electrode 606 is connected by a cable or wire 604 to the body 603 of the applicator 602. These electrodes are separate from each other, and may be replaceable/disposable. Different shaped electrodes 607 may be used with the same re-usable neurostimulator. The neurostimulator in this example includes a rigid outer body, to which the pair of electrodes is attachable, making electrical contact via one or more plug-type connectors.

FIGS. 3B-3G illustrate another embodiment of a neurostimulator as described herein. In this variation the neurostimulator is also a lightweight, wearable neurostimulator that attaches to an electrode, and includes contacts for making an electrical connection with two (or potentially more) electrically active regions (e.g., anodic and cathodic regions) on the electrode(s). However, in this example, the neurostimulator is configured to operate with a cantilevered electrode apparatus, and to attach both mechanically and electrically to the electrode apparatus at a region that is off-center on the bottom (underside or skin-facing side) of the neurostimulator, allowing one end region to be held securely to the skin while the other edge region is not pinned in this way. The "floating" end may therefore adjust slightly to different curvatures of the head, even while the electrode assembly (which may be flexible) is securely held to the skin. Thus, this cantilevered attachment mechanism may enhance comfort and adjustability of the device. In addition, the neurostimulator device may be configured specifically so that it can be comfortably worn at the user's temple, even in users wearing glasses. For example, the apparatus may be configured so that the skin-facing side (which connects to the electrode assembly via one or more connectors) is curved with a slightly concave surface having a slight twist angle. This curve shape may help the apparatus fit more snugly (more uniformly) to the surface of the temple. In addition, one end of the device (the end to be positioned in-line with the edge of the user's eye and the user's ear) may be thinner (e.g., less than 2 cm, less than 1.5 cm, less than 1 cm, less than 0.8 cm, etc.) than the opposite end, which may be worn higher up on the temple.

For example, FIGS. 3B-3G illustrate front, back, left side, right side, top and bottom perspective views, respectively of a variation of a neurostimulation device (neurostimulator or electrical stimulator) that may be used with cantilever electrode apparatuses. The overall shape of the neurostimulator may be triangular, and particularly the surface of the neurostimulator (though curved/concave and twisted) adapted to connect to the electrode apparatus and face the patient may be three-sided (e.g., roughly triangular). This roughly triangular shape may include rounded edges, and the thickness of the stimulator (in the direction perpendicular to the surface contacting the cantilever electrode apparatus) may vary, e.g., be thinner along one side, and particularly the side (the portion between the orbital edge and the auricular edge) that will extend laterally from the edge of the eye in the direction of the ear. This shape may also be beneficial when helping to fit/be worn on most people in a region of the face/head that tends to not have hair. Both adhesive and conductive hydrogel that may cover an active electrode region function more effectively on skin with little or no hair. This thin lower corner (the orbital/auricular corner)

may fit between the eyebrow and hairline, while the wider portion is positioned up in the forehead area where there is less likely to be hair.

In FIGS. 3B-3G the various edges of the neurostimulator are labeled, based on where the apparatus will be worn by the subject, as is illustrated in FIG. 3M. In general, the side of the unit worn toward the ear is the auricular edge, the side worn highest on the forehead is the superior edge, and the side worn nearest the eye/eyebrow is the orbital edge. The overall shape of the neurostimulator is triangular (including rounded edges). As used herein triangular includes shapes having rounded/smooth transitions between the three sides, as illustrated. The subject-facing surface is specifically contoured to fit in the predefined orientation, making it difficult or impossible for a subject to misapply, and risk placing the active region of the attached cantilever electrode apparatus in the wrong place. When attaching the cantilever electrode apparatus to the neurostimulator, the cantilever electrode apparatus may flex or bend so that it is contoured to match the curved and twisted surface. This surface is a section of a saddle shape, in which there is an axis of curvature around which the surface is concavely curved, and an axis of twisting, which may distort the curved surface (the two axes may be different or the same).

Within the housing, any of the neurostimulators described herein may include a processor (e.g., microprocessor) or controller, a wireless communication module that is connected to the processor, and a power source (e.g., battery, etc.). The power source may be configured to provide power to the internal circuitry and/or the circuitry driving current between anodic and cathodic regions of the electrodes when worn by the user. The power supply may be a high-voltage power supply, e.g., able to provide up to 60 V across these electrode terminals. In general, the apparatus may also include circuitry that is configured to regulate the energy (e.g., current) delivered as required by the processor, which may in turn receive instructions via the wireless communications module from a controller. The controller may also communicate information, and in particular information about the electrodes, including confirming that the electrode assembly is connected and/or what type (e.g., calm, energy, make/model, batch, etc.) of electrode assembly is attached, and an indicator of the contact with the user's skin (e.g., conductance, a parameter proportional to conductance, or a value from which an estimate of the conductance of the electrode(s) may be derived).

The electrode assembly may mechanically and/or electrically connect to the neurostimulator, e.g., by snapping to the underside of the neurostimulator at one or more (e.g., two) connectors such as snap receivers. Thus in some variations the neurostimulator may be held onto the subject's (user's) head by the electrode assembly; the electrode assembly may be adhesively connected to the user's head and/or neck to form an electrical contact with the desired regions on the user, and the neurostimulator may be connected e.g., adhesively and/or electrically, to the electrode assembly. As described below, the connectors between the neurostimulator and the electrode assembly may be positioned in a particular and predetermined location that allows the neurostimulator to be robustly connected to the electrode assembly and therefore the user's head/neck without disrupting the connection, and while permitting the system to be worn on a variety of different body shapes.

Electrode assemblies are generally described in detail below, along with specific examples and variations. In particular, described herein are electrode assemblies that are thin (e.g., generally less than 4 mm, less than 3 mm, less than 2 mm, less than 1 mm, etc. thick, which may not include the thickness of the connectors that may extend proud from the thin electrode assembly), and flexible, and may be flat (e.g., formed in a plane). For example, they may be printed on a flex material, such as the material used to print a flex circuit. In use, they can be wrapped around the head to contact it in at least two locations (e.g. at the temple and on the back of the neck). The electrode assembly may include a connector (electrical and/or mechanical) that extends proud of the otherwise flat/planar surface to connect the active regions of the electrode assembly to the neurostimulator. For example, the neurostimulator may be mechanically and electrically connected by one or more snaps extending from the front of the electrode assembly. In some examples, one snap connects to a first active electrode region (anodic or cathodic region) that is surrounded by an adhesive to adhere the active region to the user's head. A second electrode region (anodic or cathodic) on a separate part of the electrode assembly may be electrically connected to the other connector. For example, the second electrode region may be adapted to fit either on a region across the user's neck at the base of the hairline, e.g., near the midline of the neck (calm electrode configuration).

The electrode apparatus may be printed (e.g., by flexographic printing, laser printing with conductive ink, silk-screening, etc.) on a flexible (e.g. plastic) substrate (flex substrate) and may also include a pair of connectors (snaps) on the side opposite the skin-facing electrodes. The electrode active regions on the back of the assembly may include a layer of conductor (e.g., silver), over which a layer of Ag/AgCl is placed that is sacrificial and acts as a pH buffer. A next layer of hydrogel overlays the Ag/AgCl electrode so that it can uniformly transfer charge across the active region into the skin. A portion of the electrode assembly around the active electrode area may have an adhesive that permits good contact with a user's skin.

There may be multiple configurations (e.g., shapes) of the electrode assembly, and, as described in greater detail herein, the electrode assembly may generally be formed on a flexible material ('flex circuit' material) and mechanically and electrically connected to the neurostimulator.

FIGS. 3H-3K illustrate one variation of a cantilever electrode apparatus ("electrode apparatus") that may be used with a neurostimulator and may be worn on a subject's head. This variation is adapted to connect to a user's temple region and the back of a user's neck. In this example, the cantilever electrode apparatus 400 includes a plurality of electrode portions (two are shown) 403, 405. In FIG. 3H, a front perspective view is shown. The front side is the side that will face away from the subject when worn. The cantilever electrode apparatus is thin, so that the electrode portions include a front side (visible in FIGS. 3H and 3I) and a back side (visible in FIG. 3K). As shown in the side view of FIG. 3J, the device has a thin body that includes the electrode portions 403, 405 as well as an elongate body region 407 extending between the two electrode portions. The elongate body is also thin (having a much larger diameter and height than thickness). The thickness is shown in FIG. 3J.

In this example, two connectors 415, 417 (electrical and mechanical connectors, shown in this example as snaps) extend from the front of the cantilever electrode apparatus. The front of the first electrical portion 403 may also include an optional foam and/or adhesive material 421 through which the snaps extend proud of the first electrical portion. The first electrical portion is shaped and sized so that the snaps will connect to plugs (ports, holders, opening, female mating, etc.) on the electrical stimulator. As described above, the connectors may be separated by between about 0.6 and about 0.9 inches (e.g., between about 0.7 and about 0.8 inches, etc., shown in FIGS. 3H-3K as about 0.72 inches). The second electrode portion may also include a foam or backing portion 423. This foam/backing region may be optional. In some variations the separation between the connectors is not limited to 0.7 to 0.8, but may be larger (e.g., between 0.7 and 1.2 inches, 0.7 and 1.1 inches, 0.7 and 1.0 inches, 0.7 and 0.9 inches, etc.) or smaller (e.g., between 0.2 and 0.7, 0.3 and 0.7, 0.4 and 0.7, 0.5 and 0.7, 0.6 and 0.7 inches, etc.).

FIG. 3K shows a back view of this first example of a cantilever electrode apparatus. In this example, the first 403 and second 405 electrode portions are also shown and include active regions 433, 435. The active regions are bordered by adhesive 440. The first 403 electrode portion includes, on the back (patient-contacting) side, a first active region 433, which is bounded, e.g., around its entire circumference, or at least on, by an adhesive 440. The active region may include a conductive material (e.g., electrically conductive gel). Similarly, the back of the second electrode portion 405 includes the second active region 435 surrounded on two sides by an adhesive material 440 that extends to the edge of the electrode region. The adhesive may be any biocompatible adhesive that can releasably hold the material to the skin.

In general the elongate body region connecting the two electrode portions may be any appropriate length, but is generally longer than a few inches (e.g., longer than about 2 inches, longer than about 3 inches, longer than about 4 inches, longer than about 5 inches, longer than about 6 inches, longer than about 7 inches, longer than about 8 inches, longer than about 9 inches, etc.). The elongate body region may also be bent or curved, as illustrated in FIGS. 3H-3K. The bend or curve, in which the elongate body may even double back on itself, may allow the material to flex or bend to allow it to be adjustably positioned over and/or around the subject's head, as shown in FIGS. 3L and 3M, for example.

Figure 3L:
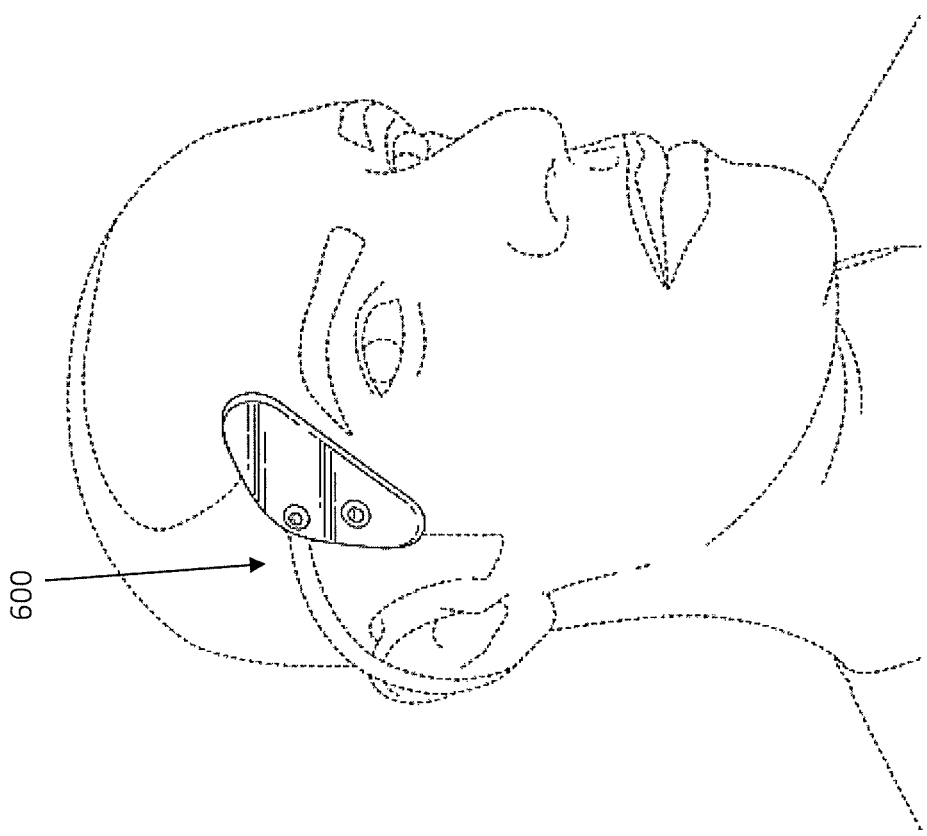
FIG. 3L illustrates the application of an electrode assembly that may be worn on the subject's head, and/or head and neck to enhance sleep.

FIG. 3L illustrates a cantilever electrode apparatus (similar to those shown in FIGS. 1A and 4A) worn on a subject's head. As illustrated, the apparatus is positioned with the first electrode portion adhesively attached at the temple region and a second electrode portion attached to a region behind the head (e.g., neck region, not shown). A neurostimulator (not shown in FIG. 3L) may be attached to the cantilever electrode apparatus either before or after it is applied to the subject. As shown in FIG. 3M, the neurostimulator may be attached to the front side of the cantilever electrode apparatus by snapping onto the proud connectors, while the elongate body region 407 is bent to extend behind the subject's head and down to a portion on the midline of the back of the patient's neck. Both the first electrode portion and the second electrode portion may be adhesively held with the electrically active regions against the skin, allowing the neurostimulator to apply energy, and in particular the waveforms as described in application Ser. No. 14/320,443, titled "TRANSDERMAL ELECTRICAL STIMULATION METHODS FOR MODIFYING OR INDUCING COGNITIVE STATE," filed Jun. 30, 2014, and herein incorporated by reference in its entirety.

In use, a user may interact with a controller (e.g., a smartphone controlled by application software/firmware) that pairs with the neurostimulator (e.g. by Bluetooth). The user may operate the controller to select the operational mode, e.g., the type of cognitive effect to be induced, including enhancing the quality of sleep or reducing sleep onset latency, and/or the device could automatically detect based on the configuration of an electrode to which the apparatus is attached. The user may select, for example, from a set of ensemble waveforms which ensemble waveform to execute. There may be separate waveforms to evoke a desired experience/effect (e.g., "calm" ensemble waveforms for reducing anxiety so that a subject may fall asleep vs. "drowsy" ensemble waveforms that are likely to induce sleep in a subject). An ensemble waveform may generally be between about 3-90 min (e.g., between about 3-60 min, between about 5-60 min, between about 5-40 min, etc., between about 3-25 minutes, etc.) long, or longer (e.g., greater than 3 min, greater than 5 min, greater than 10 min, greater than 12 min, etc.). In general, an ensemble waveform may be broken up into segments with specific pulsing parameters, e.g., current amplitude, frequency, duty cycle, charge imbalance, shorting/capacitive discharge, etc., and these parameters may change at pre-specified times for subsequent component waveforms. Once the user selects an ensemble waveform, the user can start the neurostimulation and the user can control or change the perceived intensity (e.g., by dialing the perceived intensity up or down), pause, or stop the session using the phone (app). In general, the perceived intensity can be scaled by the user between 0-100% of a target perceived intensity (e.g., a target current, frequency, duty cycle, charge imbalance, and/or shorting/capacitive discharge), using a control such as one or more buttons, sliders, dials, toggles, etc., that may be present on the controller (e.g., smartphone) in communication with the neurostimulator. The controller may also allow a user to activate ("on demand") a waveform configuration that is designed to evoke a predetermined response. For example, the control device could be adapted to display one or more icons to trigger phosphenes or an intensification of the perceived cognitive effect or skin sensation intensity. In addition, the controller may be configured to allow the user to press an icon to help in applying the electrode apparatus and/or neurostimulator. For example, activating this control may cause the smartphone to activate a front-facing camera on the phone to help the user to attach the apparatus to the head. During or after a session, a user can access help screens, a profile page, social sharing interfaces (i.e. tweet your experience), feedback about a session, and analysis & history of previous use. In general, the system may also be configured to pass data to and from the controller and/or the neurostimulator and to/from a remote server via the Internet. These data may include user information, waveform data, information about the function or state of the hardware device or electrode assembly, etc.

The neurostimulator may apply an ensemble waveform for about 3-30 min (or longer) that is made up of different "blocks" having repeated waveform characteristics; the waveform ensemble may include transition regions between the different blocks. In general, at least some of the waveform blocks (and in some variations most or all of them) generally have a current amplitude of >3 mA (e.g., between 5 mA and 40 mA, between 5 mA and 30 mA, between 5 mA and 22 mA, etc.), and a frequency of >100 Hz (e.g., between 250 Hz and 15 kHz, between 750 Hz and 25 kHz, between 750 Hz and 20 kHz, between 750 Hz and 15 kHz, etc.), the current is typically biphasic and is charge imbalanced, and has a duty cycle of between 1-90% (e.g., between 10-90%, between 30-80%, between 30-60%, etc.). One or more of these characteristics may be changed during stimulation over timescales of every few seconds to minutes. FIG. 1 shows an exemplary cycle of a waveform for TES comprising a positive-going pulse of duration $t_p$, a negative-going pulse of duration $t_n$, and a total pulse duration of $t_c$. As shown in FIG. 1 the peak of the positive- and negative-going pulses may be equal (absolute value). The duty cycle percentage may be defined as $(t_p+t_n)/t_c$ and the charge imbalance percentage may be defined as $(t_p-t_n)/(t_p+t_n)$.

In general, the TES control module may be specifically adapted to deliver a biphasic electrical stimulation signal of 10 seconds or longer between the first and second electrodes, where the signal has a frequency of 100 Hz or greater (e.g., 200 Hz or greater, 400 Hz or greater, 450 Hz or greater, 500 Hz or greater, 600 Hz or greater, 700 Hz or greater, etc.; optimally 750 Hz or greater, including 1 kHz or greater, 2 kHz or greater, 3 kHz or greater, 4 kHz or greater, 5 kHz or greater, 7.5 kHz or greater, 10 kHz or greater, 20 kHz or greater, etc.) and an intensity of 2 mA or greater (e.g., 3 mA or greater, 4 mA or greater, 5 mA or greater, 6 mA or greater, 7 mA or greater, 8 mA or greater, 9 mA or greater, 10 mA or greater, etc.). The control module may also be configured to reduce pain when applying the stimulation by controlling the duty cycle (e.g., the percent of time that the current applied is non-zero, and/or greater than zero), e.g. so that the duty cycle of the applied energy is greater than 10 percent (e.g., greater than 15 percent, greater than 20 percent, greater than 30 percent) and less than 90 percent (e.g., less than 75 percent, greater less than 70 percent, less than 60 percent). In addition, the control module may be configured so that the applied current is biphasic and/or is not charge balanced (e.g., has a DC offset, also referred to as DC bias, so that the mean amplitude of the applied waveform is non-zero). Alternatively or in addition, the control module (TES control module) may be configured to deliver waveforms biphasically asymmetric (i.e. not having the same pulse in the positive and negative direction) and/or to discharge capacitance built up on the electrodes (and in the body), e.g., by occasionally or periodically "shorting" the electrodes, and/ or by applying an opposite current(s). In general, a control module may be configured to generate stimulation that includes these parameters, and may be configured to prevent stimulation outside of these parameters, in order to avoid inducing pain.

Described herein is a method of enhancing sleep, including facilitating falling asleep (e.g., reducing sleep onset time, increasing drowsiness, facilitating the passage into sleep in a subject, etc.), Such methods may generally include: placing a first electrode of a wearable transdermal electrical stimulation (TES) applicator on the subject's skin in a first region (e.g., on a temple region on a first side of the subject's body); placing a second electrode of the TES applicator on a second location (e.g., on the back of the subject's neck above the vertebra prominens); activating the wearable TES applicator to deliver a transdermal electrical stimulation having a duty cycle of greater than 10 percent, a frequency of 250 Hz or greater, and an intensity of 3 mA or greater. The biphasic transdermal electrical stimulation may be asymmetric with respect to positive and negative going phases; and facilitating the passage into sleep by applying the biphasic transdermal electrical stimulation between the first and second electrodes for 10 seconds or longer.

Also described herein are methods of inducing sleep in a subject, which may include: placing a first electrode of a wearable transdermal electrical stimulation (TES) applicator on the subject's skin (e.g., on a temple region on a first side of the subject's body); placing the second electrode on the subject (e.g., on the back of the subject's neck above the vertebra prominens); activating the wearable TES applicator to deliver a transdermal electrical stimulation having a duty cycle of greater than 10 percent, a frequency of 250 Hz or greater, and an intensity of 3 mA or greater. The stimulation may be biphasic transdermal electrical stimulation that is asymmetric with respect to positive and negative going phases. The method may generally include inducing sleep by applying the biphasic transdermal electrical stimulation between the first and second electrodes for 10 seconds or longer.

Also described herein is a method of maintaining sleep in a subject, the method comprising: placing a first electrode of a wearable transdermal electrical stimulation (TES) applicator on the subject's skin on a temple region on a first side of the subject's body; placing the second electrode on the back of the subject's neck above the vertebra prominens; activating the wearable TES applicator to deliver a transdermal electrical stimulation having a duty cycle of greater than 10 percent, a frequency of 250 Hz or greater, and an intensity of 5 mA or greater, wherein the biphasic transdermal electrical stimulation is asymmetric with respect to positive and negative going phases; and maintaining a state of sleep in the subject by applying the biphasic transdermal electrical stimulation between the first and second electrodes for 10 seconds or longer while the subject is asleep.

As mentioned above, any of the portable transdermal electrical stimulation (TES) applicators descried herein for facilitating, inducing, and/or maintaining sleep in a subject may include: a body; a first electrode; a second electrode; and a TES control module at least partially within the body and comprising a processor, a timer and a waveform generator, wherein the TES control module is adapted to deliver a biphasic electrical stimulation signal of 10 seconds or longer between the first and second electrodes having a duty cycle of greater than 10 percent, a frequency of 250 Hz or greater, and an intensity of 3 mA or greater, wherein the biphasic transdermal electrical stimulation is asymmetric with respect to positive and negative going phases.

For example, a wearable transdermal electrical stimulation (TES) applicators for facilitating, inducing, and/or maintaining sleep in a subject may include: a body; a first electrode; a second electrode; a TES control module at least partially within the body and comprising a processor, a timer and a waveform generator, wherein the TES control module is adapted to deliver a biphasic electrical stimulation signal of 10 seconds or longer between the first and second electrodes having a duty cycle of greater than 10 percent, a frequency of 250 Hz or greater, and an intensity of 3 mA or greater, wherein the biphasic transdermal electrical stimulation is asymmetric with respect to positive and negative going phases; and a wireless receiver connected to the TES control module; wherein the wearable TES applicator weighs less than 50 grams.

Any of these apparatuses may be specifically adapted for use as a sleep-modifying apparatus. For example, in some variations, the apparatus includes one or more sensor that determine the sleep state (e.g., awake, asleep, drowsy, etc.) of the subject wearing the apparatus. Sensors may include one or more accelerometers, heart rate sensors, electroencephalogram (EEG) sensors, electromyogram (EMG, including electrooculogram EOG), etc. As used herein, a sensor may also include hardware and/or software for interpreting and/or modifying the resulting signals, including but not limited to filtering physiological signals, amplifying physiological signals, etc.

The methods and apparatuses (devices, systems) described herein may use a TES waveform having one or more characteristics from the list including: a duty cycle between 30% and 60%; a frequency greater than 5 kHz or greater than 10 kHz; an amplitude modulation, including amplitude modulation with a frequency less than 250 Hz; and a burst mode wherein stimulation pauses intermittently (i.e. on for 100 ms, off for 900 ms; on for 500 ms, off for 500 ms; and other more complex pulsing patterns, including chirping and patterns repeating at 250 Hz or lower frequency).

The methods and apparatuses (devices, systems) described herein are useful for facilitating the passage into sleep and/or inducing sleep and may include inducing one or more of the following states in the subject: increased drowsiness; increased desire to sleep: and enhanced state of calmness and carefreeness (i.e. reduced anxiety) when preparing to fall asleep, attempting to fall asleep, or actually passing into a state of sleep.

The apparatuses (devices, systems) described herein may be activated while the subject is awake (before they fall asleep) or may be put on by the user before sleep but not activated until after the user has fallen asleep. For embodiments configured to deliver TES before a subject falls asleep, a visual indicator (i.e. LED or screen) of the transdermal electrical stimulator (or a connected user device such as a smartphone running an app that controls the transdermal electrical stimulator) may be turned down or turned off when the wearable TES system is activated for facilitating the passage into sleep of the subject.

Some versions of the methods and systems described herein include sleep monitoring of the subject. Sleep monitoring may comprise using a sensor (which may be included as part of the apparatus or used along with the apparatus) to measure a subject's brain rhythms (i.e. EEG), autonomic function (including sensors to measure one or more of: galvanic skin resistance, heart rate, heart rate variability, or breathing rate), and/or movements, including movement sensors worn by the subject, coupled to the subject's bed, or configured to detect movements remotely without direct or indirect physical contact with the subject (i.e. via ultrasound or a microphone). Variations of the systems and methods described herein may further comprise an automatic modification of a transdermal electrical stimulation waveform based on the amount of time required for a subject to fall asleep. Thus, any of the apparatuses described herein may be configured to feed the sensor information back to control (e.g., turn on/off) and/or modify the TES stimulation applied.

For example, in some embodiments of the invention, a subject will fall asleep within a short period of time (i.e. less than 15 minutes; less than 10 minutes; less than 5 minutes). A TES stimulation may stop automatically when the subject is asleep, as detected by a sleep monitoring function and related components of the system. For example, TES may automatically stop when the subject is asleep at a fixed delay (alarm mode), based on a sleep state (or series of sleep states) experienced by the user, or by control of a third party (i.e. a sleep clinic technician who controls the system remotely via an Internet connection). In another example, TES may be automatically or manually (i.e. from a quick start button that can be pressed quickly and easily to minimize likelihood of waking) triggered if a subject wakes up, even briefly, so that the subject can get back to sleep quickly.

In some variations of the systems and methods described herein, a TES waveform may be started, stopped, or modified based on sleep quality being below a threshold value, where sleep quality is defined by one or more of: sleep latency, amount and/or sequence of sleep stages, sleep amount, and time during the day when sleep occurs. The sleep quality measurement may be a measurement of sleep quality from the current bout of sleep and/or from one or more previous bouts of sleep. In other variations of the systems and methods described herein, a TES waveform may be started, stopped, or modified based on a measurement of the subject's physiology or cognitive state including but not limited to: activity, stress, immune system function, diet, and mood. The methods and apparatuses (devices, systems) described herein may be configured for use before or during a nap and/or to enhance the function of the immune system (i.e. by improving the quality and/or quantity of slow-wave sleep in the subject).

In addition to 'lifestyle' applications (i.e. for general use by subjects, not for treating or diagnosing any medical condition), the TES apparatuses (systems, devices) and methods described herein for facilitating, inducing, and/or maintaining sleep in a subject may be used to treat a sleep disorder in a patient, including but not limited to: insomnia, including insomnias as a symptom of a psychiatric or mood disorder such as post-traumatic stress disorder, anxiety, emotional distress, depression, bipolar disorder, or schizophrenia; restless leg syndrome and periodic limb movement disorder; circadian rhythm disorders; sleeping sickness; parasomnia; shift work and jet lag; and hypersomnia. The TES apparatuses (systems, devices) and methods described herein for facilitating, inducing, and/or maintaining sleep in a patient may also be used to treat a disorder, disease, or symptom not generally described as a sleep disorder but for which sleep abnormalities occur in the patient, including but not limited to: post-traumatic stress disorder, a neurodegenerative disease such as Alzheimer's disease, a neurodevelopmental disorder such as Down syndrome, autism spectrum disorder, and Rett's syndrome; alcoholism; drug addiction; menopause; pregnancy; menstruation; attention-deficit disorders, including attention-deficit hyperactivity disorder; medication that affects the ability to fall asleep, including chemotherapeutic agents; and age-related sleep changes.

The systems and methods described herein may further comprise a notification that reminds the subject to wear a neurostimulator before bed and configure it for improving sleep. For example, the notification to the subject may be based on input from a location sensor in the neurostimulator or a device wirelessly connected to the neurostimulator to detect that a user is in their bedroom and a clock to determine whether the user is in their bedroom during a time when they generally go to sleep. In other embodiments, the system or method may further comprise a calming sensory stimulus (i.e. an auditory stimulus, including binaural beat, and olfactory stimuli) and/or may further comprise an alarm that wakes a subject during an identified phase of light sleep to remind the user to remove the sleep-promoting TES system.

When a subject wakes (i.e. in the morning), feedback may be provided to the subject showing how the subject's use of transdermal electrical stimulation before and/or during sleep affected a sleep quality metric selected from the group including but not limited to: sleep onset time, length of sleep, sleep latency, total length or percentage of REM sleep, total length or percentage of NREM sleep, total length or percentage of slow wave (deep) sleep, length of sleep cycles, number and/or length of night awakenings, and morning wake time.

EXAMPLES

As mentioned above, in general the use of certain TES waveforms applied prior to sleeping may improve the quantity and/or quality of sleep. In the morning, users typically wake up feeling more rested, with a more positive mood, less anxiety, and less stress (both as self-reported and as assessed by biochemical assay of saliva). FIGS. 9-14B illustrate exemplary data comparing various TES waveform that may be used to enhance sleep, including comparing to a control ("baseline") stimulation in which only sham TES was applied.

Figure 9:
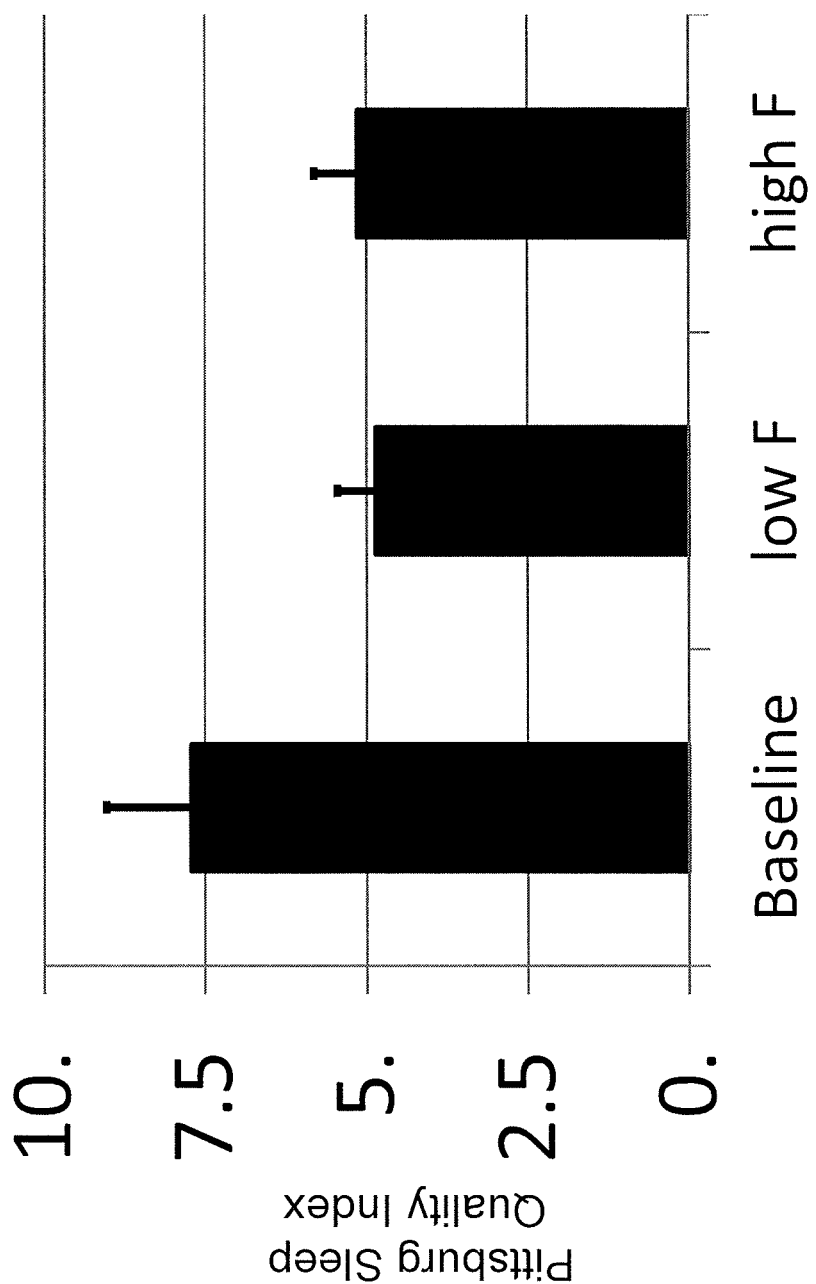
FIG. 9 is a graph showing an improvement in overall sleep (using the Pittsburgh Sleep Quality Index, PSQI) following the methods described herein in a user population (n=10). Higher scores (e.g., PSQI of greater than 5, up to a maximum score of 21) are considered a poor sleep quality. Subjects used for this study had a PSI of just over 5. Following treatment with either of two experimental TES protocols ("low F" or "high F"), the PSQI scores improved.

For example, FIG. 9 illustrates an example of an overall assessment of the effect of two exemplary TES waveforms within a range of parameter values found to enhance sleep, compared to baseline. Comparison is made using the Pittsburgh Sleep Quality Index (PSQI). In this example, the assessments compared, in a 1-week crossover design with no washout period, baseline (no TES before sleep) and two different 15-minute TES waveforms delivered through a configuration wherein an anode is at the forehead/temple area and cathode on the neck of a subject, similar to that shown in FIGS. 2A-2F. One waveform tested was referred to as 'high F' (or alternatively as 'Program B' or relaxCES) and is a pulsed waveform with variable frequency, generally between 3 kHz and 11 kHz. FIGS. 15A-15C describe three example of complete ensemble waveforms that may be similar to the "high F" TES waveforms used.

The tables shown in FIGS. 15A-15C lists the waveform parameters for each of the component waveforms. In this example the ensemble waveform is configured with short circuiting on (meaning that a capacitive discharge pulse occurs in the opposite direction after each of the biphasic pulses). In one example, the system transfers chunks (e.g., 400 ms segments) securely between the user device and the worn neurostimulator every about 400 ms (or on multiples of about 400 ms), including the neurostimulation start frequency, end frequency, starting amplitude, end amplitude, start duty cycle, end duty cycle, start percent charge imbalance, end charge imbalance, etc. The timing of wireless communication chunks at about 400 ms should not be construed as limiting the timing of communication between a controller unit and the neurostimulator. FIG. 15B illustrates a second example of a calm ensemble waveform having a slightly longer running time, running over 12 minutes. Similarly, 15C illustrates a third example of a calm ensemble waveform having a yet longer running time (over 16 minutes).

A second waveform tested in this study was referred to as 'low F' (or alternatively as 'Program A'). This second waveform has a lower pulsing frequency, variable but generally 750 Hz. FIG. 16 illustrates an example of a TES ensemble waveform such as the low F variations described herein.

In FIG. 9, a comparison of PSQI for n=10 subjects examined between baseline (no TES), high F and low F ensemble waveforms show a significant improvement of both low F and high F waveforms compared to baseline (and to other TES waveforms having parameters outside of the ranges described herein, data not shown). In general, a PSQI of greater than 5 is considered to reflect poor sleep quality.

In addition to the low F and high F parameters, acute studies performed in the afternoon used alternative 15 minute TES ensemble waveforms with even lower frequency, e.g., 500 Hz, pulsing (full set of parameters below). Surprisingly, 5 of 10 people fell asleep during the 15 minute vibe. This effect appears to be stronger for lower frequencies (e.g., low F') compared to higher frequency ('high F') ensembles, for which subjects tend to fall asleep after the vibe completes (though it is not that uncommon to fall asleep during a sleep-inducing waveform). Subject's self-reported feeling increased sleepiness (e.g., very heavy drowsy physical feelings, "face is extremely relaxed, words are slowed down and shoulders drop," feeling as though the subject woke up from a nap physically relaxed and mentally alert, etc.). In this example, the parameters (for 'very low F' stimulation) included stimulating at 500 Hz for a 15 min ensemble, having a peak current of 3.5 mA. The (illustrated in the table of FIG. 17) had a frequency of 500 Hz for 4 min and 30 sec, switching to a frequency of 550 Hz for 30 seconds (and repeating for 3 cycles of this). The duty cycle, as defined above, was 25 to 35% depending on patient comfort (they could self-adjust). The charge imbalance as defined above as the percent DC offset (see FIG. 1) was 3%. Capacitive discharging was set to "on" so that a brief capacitive discharging pulse was emitted during a portion of each positive- or negative-going pulse.

In each of the sleep studies discussed herein the subject ages ranged between 18 and 50 years old. Subjects were monitoring using one or more sleep sensors (e.g., 7 wore Actigraph sleep sensors, Phillips Actiwatch; 7 wore HRV monitor, Polar chest strap). Integrated sensors (e.g., motion sensors, etc.) in the wearable apparatus could alternatively or additionally be used. In some examples, the procedure included seven nights of each protocol. In practice, subjects may use these apparatuses for multiple nights (e.g., 2 nights, 3 nights, 1 week, 2 weeks, one month, etc.) concurrently to enhance sleep.

For example, seven nights of Program_B (e.g., using a high F ensemble TES waveform similar to that shown in FIG. 15A, running for 15 min. beginning prior to falling asleep) and seven nights of Program_A (e.g., using a low F, approximately 750 Hz, pulsing TES waveform for 15 min., similar to FIG. 16, prior to falling asleep). In the studies shown in FIGS. 9-14B, morning and evening logs were kept for study duration, sleep monitoring (e.g., Actigraph and Polar chest strap, measuring HR and HRV) was performed for the study duration during sleep. Baseline, 7 Day and 14 Day general health screening was done, assessing (by self-reporting): overall sleep score (FIG. 9), Stress, Anxiety, Depression, Fatigue and the like (FIGS. 12A-12G).

Figure 10B:
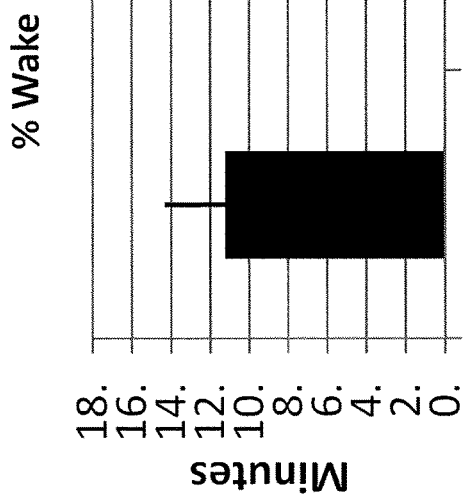
FIGS. 10A-10C compare the time to Wake after Sleep Onset (WASO, FIG. 10A), percentage of time awake (FIG. 10B), and self-reported WASO (FIG. 10C) of subjects in the trial illustrated in FIG. 9 that received either treatment A (Low F) or treatment B (High F).
Figure 10A:
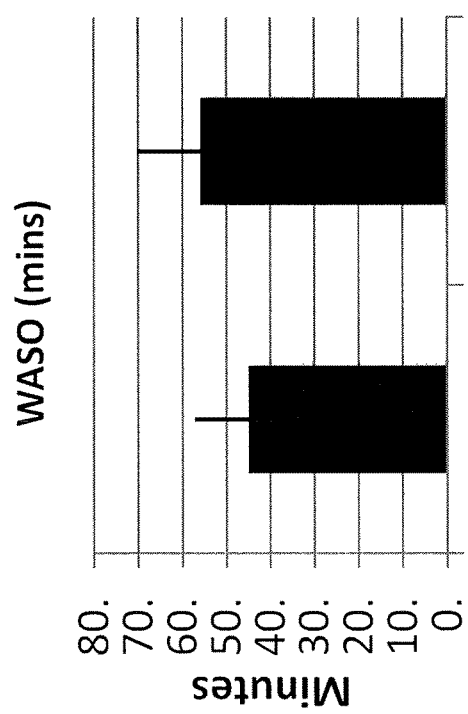
Figure 10C:
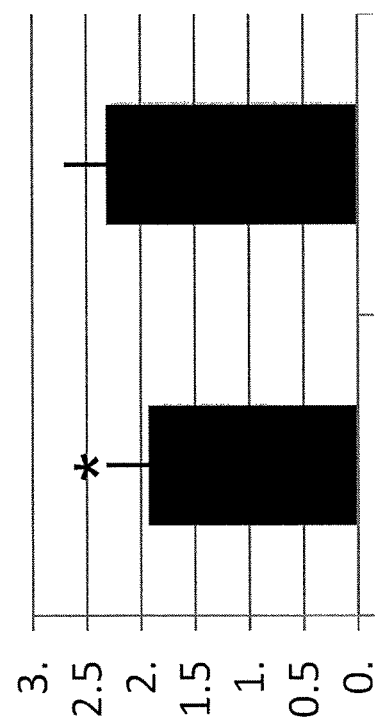

For example, as partially reflected in FIGS. 10A-10C, comparison between low F and high F stimulation protocols suggests that the improved sleep quality (compared to baseline) in these two exemplary stimulation protocols may come in part due to fewer awakenings, fewer unknown awakenings, and in particular, fewer awakenings caused by needing to use a bathroom. See, e.g., FIG. 10A, showing a bar graph of WASO in minutes, and FIG. 10B, showing comparison between the percentage of time, and FIG. 10C, showing the self-reported WASO events.

Similarly, FIGS. 11A-11C illustrate heart rate variability (FIG. 11A, showing HRV in very low frequency bands (e.g., oVLF of 57.5 to 75), HRV power in the low-frequency band, FIG. 11B shows pLF (between 15 and 20), while FIG. 11C compares the pHF indicating slight differences between the low F and high F protocols.

FIGS. 14A and 14B compare two empirical measures of sleep quality, morning amylase and morning cortisol, between the high F and low F groups. This biochemical analysis included collecting saliva on mornings during the treatment period for each of the high F and low F parameters. The user collected saliva was processed by a third party for alpha-amylase and cortisol, both of which are known to correlate to acute and chronic stress. The lower frequency regime (Low F) showed a slightly greater effect compared to the high F regime, consistent with the other (self-reported) data, e.g., in FIGS. 11A-13B.

In general, the methods of improving sleep by TES stimulation described herein show that, relative to baseline, both low F and high F TES ensemble waveforms improved sleep quality as assessed by the Pittsburgh Sleep Quality Index (for which higher scores correspond to lower quality sleep). Further, the Low F waveforms led to fewer awakenings and reduced the length of awake time after sleep onset relative to the high F waveform (see, e.g., FIGS. 10A-10C), and the low F waveforms caused a reduction in power in the very low frequency band relative to high F. Hear rate variability (HRV) in the low frequency and high frequency bands is slightly higher after low F TES waveform than the high F waveform. These frequency bands are typically described as high frequency (HF) brain activity, from 0.15 to 0.4 Hz, low frequency (LF) brain activity, from 0.04 to 0.15 Hz, and the very low frequency (VLF) brain activity, from 0.0033 to 0.04 Hz.

In general, the high F and low F waveforms were relatively similar, though both improved over baseline. For example, improvements were seen in the time it takes to fall asleep (sleep onset latency), reductions in the occurrence of nightmares, increased total sleep time, and improved mood. In a previous study, high F beat baseline on all above metrics except for those related to middle of the night and early morning awakenings.

Thus, in general, the application of TES before bed using either low F or high F waveforms led to improvements in subject's mood and energy in the morning as assessed with the positive and negative affect schedule (PANAS) scale. These beneficial effects on mood may include reduced anxiety (FIG. 12A), reduced depressive feelings (FIG. 12B), reduced stress (FIG. 12C), increased positive affect (FIG. 12D), reduced negative affect (FIG. 12E), reduced irritability (FIG. 12F), and reduced fatigue (FIG. 12G). Application of TES as described herein before sleeping may also improve depression, anxiety and stress, as indicated by the Depression, Anxiety and Stress Scale (DASS), a clinical measure with a 0 to 3 scale used for FIGS. 12A-12G. Affectivity was measured on a 5 point scale, ranging from 1 to 5, irritability was measured on a 0 to 3 scale, and fatigue was measured on a 0 to 10 scale.

The self-reported scores for PANAS and DASS are consistent with the biochemical markers examined (e.g., decreased Awakening Amylase and Increased Awakening Cortisol) for the high F, low F and very low F TES stimulation. Cortisol is on a diurnal pattern with its peak 30 min after waking; generally, the higher the morning rise in cortisol, the more 'normal' the indicator is, whereas a blunted rise in morning cortisol may be indicative of a disease state such as depression, post-traumatic stress disorder (PTSD), anxiety and/or sleep deprivation. In general, the majority (e.g., ⅔ or more) of subjects reported feeling more rejuvenated, less drowsy, less anxious, and less stressed the next day. Over ⅔ of subjects also reported having an easier time falling asleep and/or getting more sleep following the use of the TES methods described herein.

The TES waveforms that may be applied (e.g., to the subject's neck or head and neck) to enhance sleep as described herein include a range of parameters that may be adjusted for both efficacy and comfort. The data described herein suggest that in some variations it may be beneficial to provide relatively low frequency (e.g., 250 Hz to 750 Hz, 250 to 1 kHz, 250 to 3 kHz, 250 to 5 kHz, etc.) stimulation at relatively high current (e.g., >3 mA, greater than 4 mA, greater than 5 mA, etc.); however these two parameters alone, low frequency and high current, typically result in painful and/or unpleasant sensations on the head and/or neck when applied there. In order to achieve a combination of low (250-750 Hz) frequency and high current (>3 mA, 3-40 mA, >5 mA, etc.) it may be beneficial to include one or more of the modulation schemes described herein, including DC offset (biphasic, asymmetric stimulation in which the positive and negative going pulses are different durations and/or amplitudes), percent duty-cycles (e.g., between 10-80%, etc.) and the use of an AC (carrier) frequency (<250 Hz). In some variations, the use of just one or two of these modulation schemes may be sufficient (e.g., using just a DC offset and a percent duty cycle between 10-80%, or just a DC offset and an AC carrier frequency <250 Hz, or just a percent duty cycle between 10-80% and an AC carrier frequency of <250 Hz), while in some variations, all three may or must be used.

EXAMPLE

As discussed above, described herein are methods and apparatuses for noninvasive neuromodulation, and more specifically to configurations and methods for transdermal electrical stimulation systems adapted to improve sleep and mood. This has been shown experimentally as will be described below.

Achieving optimal human performance that involves cognitive or physical work requires quality sleep and a positive mental attitude. The ascending reticular activating system (RAS) represents a powerful set of endogenous neuromodulatory circuits that gate and tune global brain responses to internal and external cues, thereby regulating consciousness, alertness, and attention. The activity of two major RAS nuclei, the locus coeruleus (LC) and pedunculopontine nucleus (PPN), can be altered by trigeminal nerve modulation. Monosynaptic afferent inputs from the sensory components of trigeminal nerve branches project to the trigeminal sensory nuclear complex (TSNC), which has direct and polysynaptic connections to the LC and PPN. We previously found high-frequency (7-11 kHz) transdermal electrical neuromodulation (TEN) of the trigeminal nerve rapidly induces physiological relaxation, dampens sympathetic nervous system responses to acute stress, and suppresses levels of noradrenergic biomarkers. Given the established roles of LC and PPN neuronal activity in sleep regulation, psychophysiological arousal, and stress, we conducted three studies designed to test hypotheses that modulation of the TSNC can improve sleep quality and mood in healthy individuals (n=99). Across a total of 1,386 days monitored, we observed TEN modulation of trigeminal and cervical nerves prior to sleep onset produced significant improvements in sleep quality and affective states, quantified using clinically validated surveys, overnight actigraph and heart rate recordings, and biochemical analyses compared to baseline or sham controls. Moreover, we observed some frequency dependence in that TEN delivered at lower frequencies (TEN$_{LF}$; 0.50-0.75 kHz) was significantly more effective at improving sleep quality and reducing anxiety than higher frequency TEN waveforms. Collectively our results indicate that transdermal electrical neuromodulation of trigeminal and cervical nerve branches can influence TSNC activity in a manner that significantly improves sleep quality and significantly reduces stress. We conclude that biasing RAS network activity to optimize sleep efficiency and enhance mood by electrically modulating TSNC activity through its afferent inputs holds tremendous potential for optimizing mental health and human performance.

The ascending reticular activating system (RAS) is a collection of nuclei and circuits that sort, filter, integrate, and transmit incoming sensory information from the brain stem to the cortex to regulate sleep/wake cycles, arousal/alertness, attention, and sensorimotor behaviors. The endogenous neuromodulatory actions of the RAS on consciousness and attention are orchestrated by at least three distinct sets of brain stem nuclei that include cholinergic neurons of the pedunculopontine nucleus (PPN), noradrenergic neurons of the locus coeruleus (LC), and serotonergic neurons of raphe nuclei. Through a cytoarchitectural meshwork of interconnected brain stem nuclei in the pons and midbrain, sensory inputs first act upon the brain to engage ascending RAS networks, which generate global arousal ("waking"), alerting, and orienting cues as parsed sensory information projects through thalamic pathways onto the cortex for additional processing and integration. More specifically the local and distal synaptic circuits formed by axons of neuromodulatory RAS networks (including neurons of the LC, PPN, RN) gate information flow from the sensory environment to the cortex and, in an activity-dependent manner, are capable of rapidly triggering neurobehavioral transitions across different states of behavioral awareness and consciousness. Depending on their firing rates for example, neurons of the PPN can differentially mediate REM sleep states and neurons of the LC can trigger sleep/wake transitions. Disrupted activity of ascending RAS networks underlies several neuropsychiatric conditions and disorders, such as insomnia, anxiety, depression, post-traumatic stress disorder (PTSD), and attention deficit hyperactivity disorder (ADHD). Therefore, a neural interface capable of dynamically and electrically modulating RAS networks should be able to provide a chemical-free approach to restoring poor daily function attributable to sleep loss or attention and mood disorders. Such an interface would also support new approaches capable of optimizing normal human performance.

The trigeminal nerve or the fifth cranial nerve (cranial nerve V) bilaterally innervates the anterior half of the head and face including around the top of the scalp, the forehead, around eye orbits, nasal region, lips, jaw, and the oral cavity. Three main branches of the trigeminal nerve (ophthalmic, maxillary, mandibular branches) and their thousands of sub-branches transmit sensory information (chemical, thermal, mechanical, pain, and proprioceptive) via monosynaptic connections to the trigeminal sensory nuclear complex (TSNC). The TSNC itself is an elongated structure with several functional divisions (for example, the primary sensory nucleus and the spinal nucleus) spanning from the cervical spinal cord to the midbrain. The TSNC has been functionally mapped using multimodal trigeminal stimulation combined with fMRI and DTI in humans. The TSNC also receives some non-trigeminal sensory information from the neck via cervical afferents. In turn the TSNC projects incoming sensory information through ascending pathways to multiple brain regions that regulate arousal and coordinate neurobehavioral engagement with the environment, such as the thalamus, the superior colliculus, the cerebellum, and the inferior olive. Several other electrophysiological and neuroanatomical studies have provided definitive evidence of functional synaptic connectivity between trigeminal afferents and the PPN and LC.

Besides its robust functional connectivity to ascending RAS networks, a major advantage of the TSNC as a neuromodulation target is that its primary monosynaptic inputs can be noninvasively accessed and coupled to using safe and comfortable transdermal neurostimulation approaches. Transcutaneous trigeminal nerve stimulation (TNS) has been shown to be effective for treating neuropsychiatric conditions like depression, PTSD, generalized anxiety disorder (GAD), ADHD, as well as neurological disorders like epilepsy and headache. Interestingly, acute TNS at a frequency of 120 Hz has been demonstrated to induce sleepiness and sedative like effects in healthy adults while 2.5 Hz stimulation frequency did not. The observations made by Piquet and colleagues (2011) suggest that TNS may provide some benefit for some sleep disturbances and insomnia.

We recently described an approach to transdermal electrical neuromodulation of trigeminal and cervical nerve afferents that suppressed physiological and biochemical signatures of sympathetic tone and noradrenergic activity. We showed that pulsed (7-11 kHz) TEN of trigeminal and cervical afferents significantly suppressed basal sympathetic tone compared to sham as indicated by functional infrared thermography of facial temperatures, significantly lowered levels of tension and anxiety on the Profile of Mood States scale compared to sham, and in response to acute stress induction TEN significantly suppressed changes in heart rate variability, galvanic skin conductance, and salivary α-amylase levels compared to sham. Based on these findings, we hypothesized that repeated daily dampening of psychophysiological and biochemical arousal might improve mood if used nightly to increase the quality, duration or efficiency of sleep. Supportive of this hypothesis there are numerous lines of evidence that suggest insomnia is a "waking" disorder (hyper-arousal) of RAS networks rather than a sleep disorder per se. Viewed as such, we more specifically hypothesized that decreasing neurobehavioral and psychophysiological arousal by perturbing trigeminal LC/RAS networks prior to sleep onset for repetitive nights can enhance the restorative qualities of sleep on mood and mental health. Below we describe the results from our findings that demonstrate TEN of trigeminal afferents significantly improves sleep quality and mood on weeklong time scales. We speculate noninvasive modulation of the TSNC will provide a valuable platform approach to restoring and optimizing brain function and mental health.

Results

Repeated nightly TEN significantly improves waking mood and reduces weekly stress compared to baseline.

In a first experiment (experiment 1), we examined the impact of before bed TEN on mood and mental health. Volunteers (n=38) completed a week of baseline assessments followed by a week of nightly TEN treatments (20 min) self-administered within 30 min of going to bed (FIG. 18A). Each morning, participants reported their mood using the Positive and Negative Affectivity Scale (PANAS) and by rating their degree of waking drowsiness and refreshment (See Methods). Mental health was captured by weekly responses to the Depression, Anxiety and Stress Scale (DASS). The PANAS and DASS are validated and widely used scales that capture fluctuations in mood and indicators of mental health, respectively.

FIGS. 18A and 18B show experimental designs implemented for testing the effects of nightly repeated, self-administered transdermal electrical neuromodulation of trigeminal and cervical nerve sensory afferents on sleep and mood. A, The illustrations show that in Experiments 1 and 2 volunteers had one week or baseline assessment then self-administered transdermal electrical neuromodulation of trigeminal and cervical nerve afferents or an indistinguishable active sham waveform nightly before bed during the second week of testing. Several metrics were used to evaluate morning mood, weekly mental health indicators, and sleep quality (see Methods). B, In Experiment 3 we implemented a double-blinded crossover design where subjects self-administered an active sham treatment or real TEN (3-11 kHz, 5-7 mA average current amplitude) treatment nightly before bed for one week and then either real TEN or low-frequency TEN (TEN$_{LF}$; 0.50-0.75 kHz, <5 mA average current amplitude). Again an array of metrics were used to determine the impact of sham treatment, TEN-treatment, and TEN$_{LF}$-treatment on sleep quality and mood.

Figure 19A:
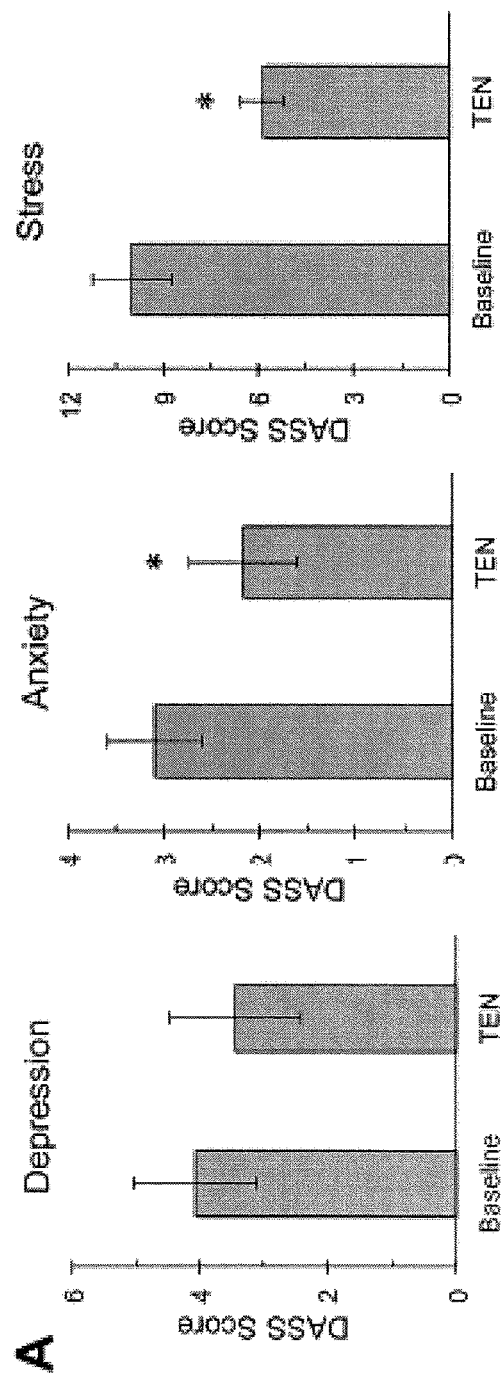
FIGS. 19A and 19B show acute transdermal neuromodulation of trigeminal and cervical afferents prior to sleep onset significantly reduces stress and anxiety.
Figure 19B:
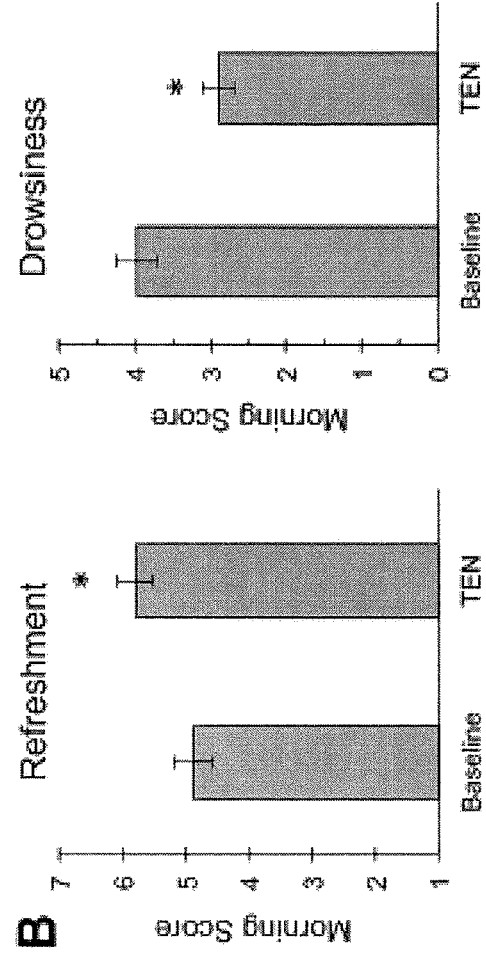

Relative to baseline, TEN treatment improved positive affect by 9% (t(35)=3.427, p=0.002) and reduced negative affect by 10% (t(35)=−3.147, p=0.003) according to the PANAS (FIG. 20). Compared to baseline, indicators of mental health recorded by the DASS (FIG. 20) revealed that TEN significantly reduced stress (t(30)=−3.982, p<0.001) and anxiety (t(29)=−2.177, p=0.038) by 41.3% and 30% respectively, whereas depression scores remained unchanged (p=0.469; FIG. 19A). Further, during the TEN treatment period, participants felt 27% less drowsy (t(36)=−4.859, p<0.001) and 17.92% more refreshed (t(36)=4.908, p<0.001) upon waking compared to the baseline period (FIGS. 19B and 20). These data indicate that nightly TEN treatments self-administered prior to bed improve morning mood, awakening affect and arousal, and reduces stress and anxiety on weeklong time scales. The enhanced morning affectivity and arousal combined with the mechanisms of action posited by Tyler et al (2015) suggest TEN may enhance sleep quality when used prior to bedtime.

FIGS. 19A and 19B illustrate acute transdermal neuromodulation of trigeminal and cervical afferents prior to sleep onset significantly reduces stress and anxiety. Data obtained from Experiment 1 are shown as a series of histograms. A, The histograms illustrate mean scores obtained from the Depression. Anxiety, and Stress Scale (DASS) and show a significant reduction in stress and anxiety following one week of nightly self-administered TEN compared to the baseline week. B, The histograms illustrate mean scores obtained on the daily-administered Awakening Drowsiness and Refreshment Scale (see Methods). These data show that nightly TEN significantly increased the feelings associated with refreshment and significantly decreased feelings associated with drowsiness in the mornings compared to baseline. An asterisk indicates a p<0.05.

Repeated nightly TEN significantly modulates autonomic activity, increases sleep quality, and improves indicators of mental health.

Based on our observations in experiment 1 and our previously described observations, we hypothesized that significantly elevated morning mood and rejuvenation is the result of improved sleep quality via TEN dampening sympathetic nervous system and LC activity prior to bedtime (FIGS. 20, 19A and 19B). Therefore in a second experiment (experiment 2) we implemented a mixed design (FIG. 18A) in a different group of participants to determine the repeatability of TEN effects on mood observed in Experiment 1, as well as to determine the impact of TEN treatment (20 min nightly for 7 nights) on sleep quality and sleep patterns, which are known to be regulated by the autonomic nervous system, LC and alterations in norepinephrine.

In experiment 2, participants completed one week of baseline followed by one week of sham (n=17) or TEN (n=18) treatments. Each morning, participants completed the PANAS, rated waking drowsiness and refreshment, reported number of awakenings, and rated overall sleep quality, and at the end of each week, they completed the DASS. Throughout the experiment, to capture objective sleep metrics, participants wore a Philips Actiwatch2, a clinically validated actigraph that reliably tracks sleep wake/ cycles (see Methods). Participants also wore a Polar H7 heart rate monitor to sleep each night to record electrocardiogram data (ECG), from which heart rate (HR) and heart rate variability (HRV) metrics were derived.

Figure 22A:
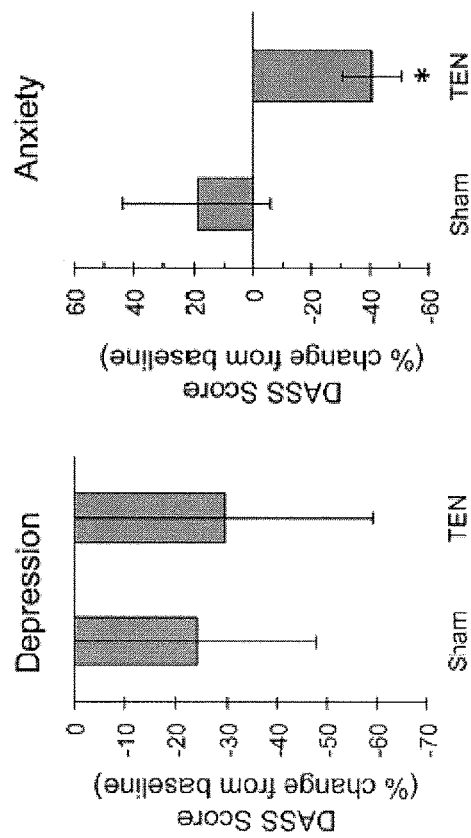
FIGS. 22A and 22B illustrate the effects of self-administered trigeminal and cervical afferent neuromodulation prior to sleep onset significantly improves mood and increases sleep time.

Building on the findings from experiment 1, relative to baseline, TEN treatment improved positive affect by 10.86% (t(17)=4.859, p<0.001), but failed to alter negative affect (t(17)=−0.237, p=0.815; FIG. 21). Further, during the TEN treatment period, participants felt 18.95% less drowsy (t(17)=−4.859, p<0.001) and 13.33% more refreshed upon waking (t(17)=4.908, p<0.001; FIG. 21). During the sham-treatment period, there were no changes from baseline in affectivity (PANAS) or waking arousal (p>0.200; FIG. 21). To examine the impact of TEN on stress, anxiety, and depression symptoms we conducted a series of one-way analyses of variance (ANOVA) comparing DASS score changes from baseline for the TEN- and sham-treatment groups. The TEN-treatment group reported a 59.53% greater reduction in stress (F(1, 25)=4.907 p=0.036) and 30.68% greater reduction in anxiety (F(1, 25)=4.392, p=0.047) compared to the sham-treatment group (FIG. 22A). The change in depression symptoms were similar across the two groups (F(1, 25)=0.091, p=0.766). These results suggest that relative to baseline, TEN-treatment prior to bed improves mood and symptoms of mental health whereas sham treatments do not.

Figure 22B:
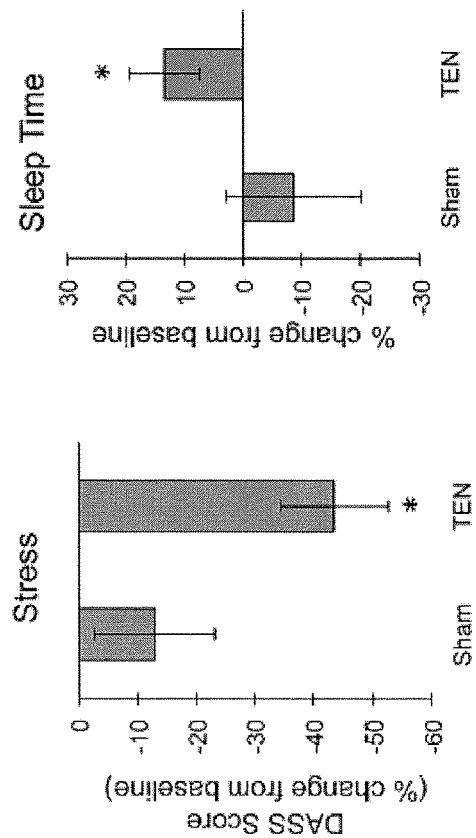

Beyond improvements in mood, we observed that TEN produced favorable changes in sleep quality and sleep patterns. Compared to baseline, TEN treatment resulted in a 36.68% reduction in self-reported middle of the night awakenings (t(17)=−3.531, p=0.003) and an improvement in sleep quality (t(17)=2.155, p=0.046; FIG. 21). There were no differences in middle of night awakenings and sleep quality between the baseline period and sham-treatment period (p>0.145). Self-reported sleep improvements mirrored sleep cycle changes captured by actigraphy, such that compared to baseline, the TEN-treatment period resulted in significantly increased sleep time (t(14)=2.255, p=0.041; FIG. 22B) and significantly decreased percent time awake (t(14)=−2.329, p=0.035).

FIGS. 22A and 22B show self-administered trigeminal and cervical afferent neuromodulation prior to sleep onset significantly improves mood and increases sleep time. Data from Experiment 2 are shown as histograms of the percent change in depression, stress, and anxiety as indicated by the DASS, as well as actigraphy-recorded sleep time for TEN and active sham treatment groups compared to baseline. An asterisk indicates a p<0.05.

Figure 23:
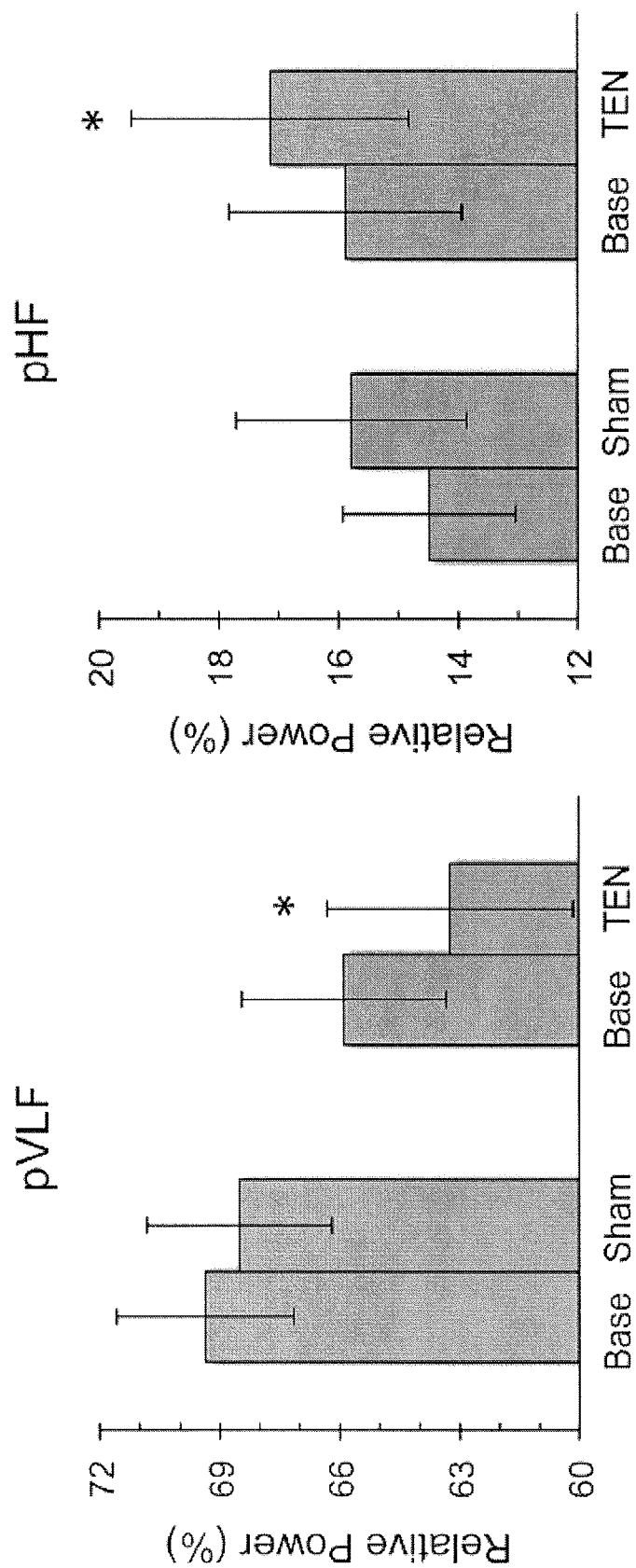
FIG. 23 illustrates the effect of nightly TEN influences autonomic nervous system activity overnight indicated by changes heart rate variability (pVLF on the left, pHF on the right).

There were no significant differences in sleep time or percent awake time recorded by actigraphy between the sham-treatment period and baseline (all p-values>0.466). Sleep changes due to TEN uses were also reflected by HRV outcomes. Compared to the baseline period, during the TEN-treatment period participants demonstrated a 4.04% decrease in the relative power of the very low frequency (pVLF) HRV band (t(14)=−2.469, p=0.027; FIG. 23) and 9.04% increase in the relative power of the high frequency (pHF) HRV band (t(14)=2.160, p=0.049), whereas no changes in other HRV metrics differed between sham treatments and baseline (all p-values>0.135).

TEN differentially impacts sleep patterns in a manner dependent on neuromodulation waveform pulse frequency.

Figure 27:
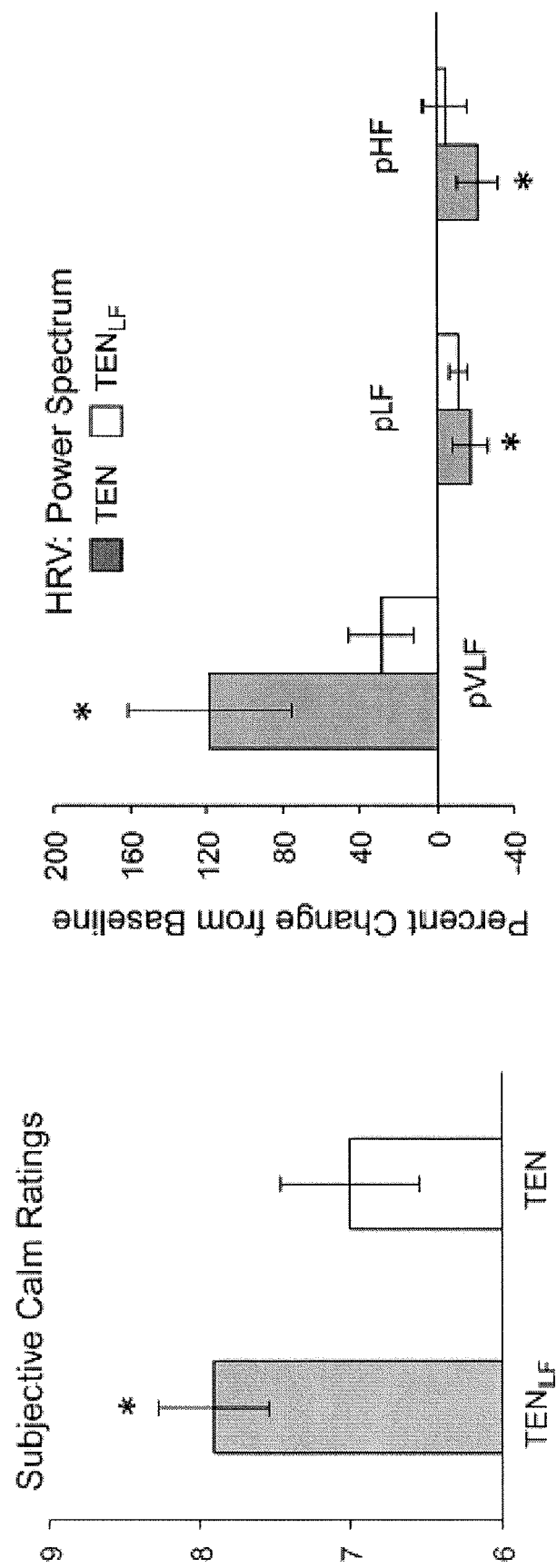
FIG. 27 illustrates the effects of a low-frequency TEN waveform on subjective relaxation (subjective calm ratings on the left) and heart rate variability (on the right).

In a third experiment (experiment 3) we implemented a randomized double-blinded crossover design (FIG. 18B) in a different set of participants (n=25) to determine if a frequency-shift in the neuromodulation waveform parameters used would produce the same impact on sleep quality and mood as we observed in Experiments 1 and 2. We specifically compared the TEN waveform (3-11 kHz pulse frequency, 5-7 mA average current amplitude) used in Experiments 1 and 2 to an active sham treatment (n=10) and a lower frequency TEN treatment ($TEN_{LF}$; 0.5-0.75 kHz, <5 mA average current amplitude; n=12). In pilot experiments we found $TEN_{LF}$, compared to higher frequency TEN, produced more robust effects on subjective reports of relaxation and physiological indicators of stress suggesting a more pronounced dampening of sympathetic nervous system activity (FIG. 27). We therefore hypothesized that $TEN_{LF}$ might produce stronger effects on sleep. TEN treatments were grouped as TEN and Control treatments, such that TEN and active sham served as Control treatment groups while $TEN_{LF}$ and TEN comprised the TEN treatment group as specified. Each treatment period lasted one week beginning on consecutive Fridays, with assessments at similar times for each week for each participant. At each of three office visits participants completed the Pittsburgh Sleep Quality Index (PSQI) and the DASS. Each morning during the treatment weeks participants completed the Karolinska Sleep Diary (KSD), a validated measure used to capture information about prior nights sleep (see Methods). As in Experiment 2, participants wore the Philips Actiwatch2 throughout the testing period and a Polar H7 heart rate monitor throughout each night.

FIG. 23 shows nightly TEN influences autonomic nervous system activity overnight indicated by changes heart rate variability.

Data from Experiment 2 are shown as histograms illustrating the relative powers of the very low-frequency (pVLF) and high-frequency (pHF) bands of heart rate variability (HRV) spectra recorded overnight for one week per treatment condition. The histograms illustrate TEN- and active sham-treatment compared to baseline. An asterisk indicates a p<0.05.

We first found that TEN produced the same effects on sleep quality and mood compared to control as we observed in Experiments 1 and 2 (data not shown). We next examined the changes that TEN produced on stress, anxiety and depression (DASS) compared to control. We observed that TEN produced a 36.13% greater reduction in anxiety than sham Control (t(20)=−3.406, p=0.003). There were no perceptible changes in symptoms of stress (t(20)=0.670, p=0.510) or depression (t(20)=−1.418, p=0.172) between the two conditions. Further, across the two conditions (TEN vs active sham Control), there were no changes in self-reported sleep patterns, including sleep quality, time till sleep onset, number of awakenings, and sleep duration. However, the objective actigraph measurements captured changes in sleep/wake cycles such that TEN treatment resulted in 12.12% less wake time (t(19)=−2.381, p=0.028), 9.50% fewer middle of the night wake-ups (t(19)=−3.781, p=0.001), and a 9.13% reduction in the percent of wake time (t(19)=−2.241, p=0.037) compared to sham Control (FIG. 24A). Despite stability of self-reported sleep pattern data between TEN and control treatments, the data obtained using actigraphy reliably suggest clear improvements in the sleep/wake cycle when using TEN compared to sham Control. We also observed effects reflecting changes in autonomic balance as indicated by significant differences in HR and HRV between TEN and sham control treatment. Relative to active sham Control, TEN decreased the R-R (t(14)=−2.372, p=0.033), marginally increased HR (t(14)=1.927, p=0.075), decreased RMSDD (t(14)=−4.144, p=0.050), marginally increased the relative power of the LF band of the HRV spectrum (t(14)=1.878, p=0.081), and significantly increased the peak LF (t(14)=3.873, p=0.002; FIG. 24B). All other HRV metrics remained stable across the two conditions (all p-values>0.289).

FIGS. 24A and 24B shows actigraphy shows that TEN significantly improves sleep quality. Results from Experiment 3 showing differences in actigraphy metrics and HRV are shown for TEN and Control groups as histograms. A, The mean number of nightly wakeups, time awake after sleep onset (WASO), and percent time awake recorded using actigraphy illustrate that TEN exerted a significant improvement in sleep quality compared to active sham Controls. B, The mean R-R interval and root mean square of the standard deviation (RMSDD) for HRV, as well as the relative power of the low-frequency (pLF) band of HRV spectra are shown for TEN and active sham Control treatments. An asterisk indicates a p<0.05.

In the subset of participants that received the $TEN_{LF}$ and TEN treatments, we found that $TEN_{LF}$ improved sleep quality and mood outcomes beyond the effects evidenced by TEN in Experiments 1 and 2. Compared to TEN, $TEN_{LF}$ reduced self-reported actiwatch-recorded number of wakeups (t(9)=2.796, p=0.021), wake time after sleep onset (t(9)=2.808, p=0.020), and percent of time awake after sleep onset (t(9)=3.006, p=0.015; FIG. 25A). In addition, we observed that $TEN_{LF}$ produced a 32.17% greater reduction in anxiety from baseline than TEN (t(8)=−2.382, p=0.044), but there were no changes in symptoms of stress (t(8)=0.928, p=0.381) or depression (t(8)=−0.769, p=0.467; FIG. 25B).

We also examined the effect of TENs as described herein on stress and sleep biomarkers, cortisol and salivary α-amylase. The protein enzyme α-amylase is widely recognized as a biochemical marker of sympathetic nervous system activity and sympathoadrenal medullary (SAM) axis activation. More specifically, salivary levels of α-amylase directly correlate with plasma norepinephrine (NE) concentrations following the induction of acute stress. It has been shown in animals ranging from flies to humans that α-amylase is a reporter of sleep drive as it increases with accumulating sleep debt. To assess the impact of TEN on SAM axis activity as it relates to sleep/wake cycles and daily stress, we examined fluctuations in salivary α-amylase (sAA) and cortisol levels upon waking, in the evening and before bed the final 3 days in each week of the TEN vs $TEN_{LF}$ treatments during Experiment 3 (N=8, FIG. 18B). We found that the mean waking levels of sAA were significantly lower in the $TEN_{LF}$ group ($TEN_{LF}$=133.78±85.83 U/mL) compared to the TEN group (TEN=217.33±134.23 U/mL); t(5)=−3.524, p=0.017; FIG. 25C). There were no differences between TEN treatments in afternoon and bedtime sAA (p>0.5). These data indicate that compared to TEN, $TEN_{LF}$ produced changes reflecting lower levels of the sleep debt and stress upon awakening.

FIGS. 25A-25C shows low-frequency TEN improves the efficacy of trigeminal and cervical afferent modulation for improving sleep quality. Results from Experiment 3 showing differences in actigraphy metrics and HRV are shown for TEN low-frequency ($TEN_{LF}$) and the Control TEN groups as histograms. A, The mean number of nightly wakeups, time awake after sleep onset (WASO), and percent time awake recorded using actigraphy illustrate that $TEN_{LF}$ exerted a significant improvement in sleep quality compared to TEN Controls. B, Histograms illustrating data obtained from the DASS across treatment groups are illustrated. C, The histograms illustrate the results obtained from biochemical quantification of waking cortisol concentrations and α-amylase activity in saliva across treatment conditions. An asterisk indicates a p<0.05.

While sAA reflects NE levels and acute SAM axis activity, cortisol is another biomarker, which is under complex hormonal control of the hypothalamic-pituitary-adrenal (HPA) axis. Elevated salivary cortisol levels prior to bedtime are a predictor of insomnia often related to hyper-arousal, metabolic dysfunction and other mood disorders, but its causal importance in poor sleep remains unclear. Reflective of adrenal fatigue however, insomnia and poor sleep have been shown to significantly dampen the cortisol awakening response (CAR), which is a specific phase of the diurnal cortisol rhythm. We observed no differences in afternoon or bedtime cortisol levels across the treatment groups (all p-values>0.5). We did find that when participants used $TEN_{LF}$ prior to bed they exhibited a stronger CAR, a significant 26.3% higher salivary cortisol concentration compared to when they used TEN ($TEN_{LF}$ waking cortisol concentration=1.44±0.41 µg/dL, TEN waking cortisol concentration=1.14±0.322 µg/dL; t(5)=2.850, p=0.036; FIG. 25C). These particular observations indicate that $TEN_{LF}$ produced more robust effects than TEN on the restorative features of sleep by significantly improving the quality of the sleep/wake cycle.

The ascending reticular activating system (RAS) represents a collection of brain stem nuclei and neuromodulatory projections, such as noradrenergic radiations from the locus coeruleus (LC) and cholinergic axons from the pedunculopontine nucleus (PPN) to higher brain circuits including the thalamus, hippocampus, amygdala, and vast regions of cortex. These ascending networks are known to provide strong neurophysiological control of consciousness, sleep/wake cycles, attention, alertness, other aspects of cognition including behavioral flexibility. Starting from the periphery, primary trigeminal and cervical afferent inputs to the trigeminal sensory nuclear complex (TSNC) from sensory and proprioceptive fibers located on the sides and front of the face, oral cavity, and anterior and posterior cervical regions of the neck provide robust disynaptic and polysynaptic regulation of LC and PPN neuron activity. Demonstrating functional effects on ascending RAS circuitry, we have shown that high-frequency (7-11 kHz) transdermal electrical neuromodulation (TEN) of trigeminal and cervical afferents can rapidly suppress psycho- and neuro-physiological arousal as indicated by a significant dampening of sympathetic nervous system activity and suppression of noradrenergic and sympathomedullary (SAM) axis biomarkers in response to an acute stress challenge. Given this context, in the present report we tested the hypothesis that self-administered, nightly TEN prior to bedtime would improve sleep quality and mood. Our conclusions based on data and observations gathered from the three independent experiments described in this study are that nightly TEN does cause a significant improvement in the quality of sleep and mood across weeklong timescales.

Thus, it may be possible to interface with the trigeminal sensory nuclear complex to functionally regulate ascending neuromodulatory systems, using the apparatuses and methods described herein.

Figure 26:
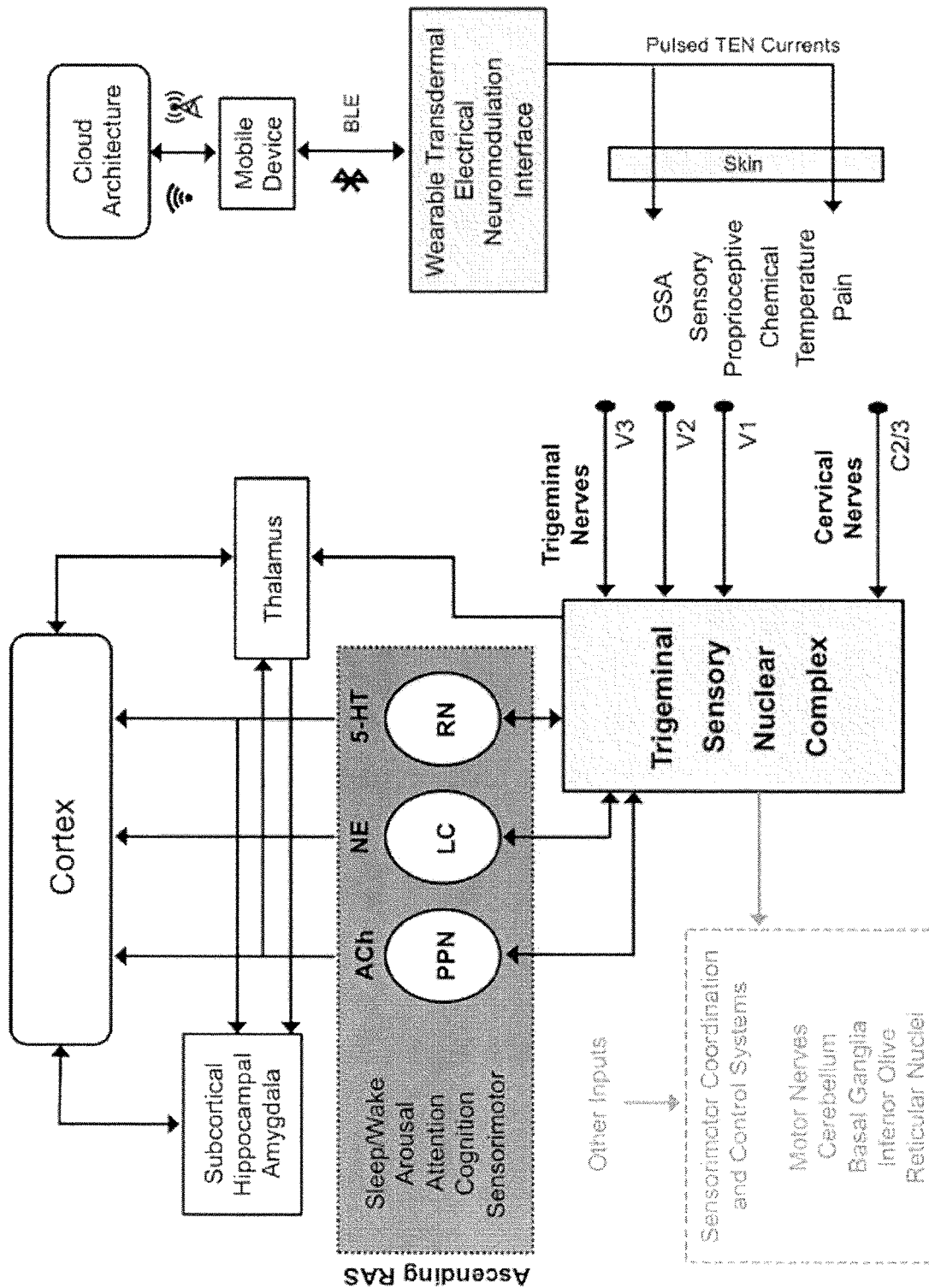
FIG. 26 is an example of a schematic illustrating interfacing with the ascending reticular activating system through the trigeminal sensory nuclear complex.

There is a growing need for neural interfaces capable of modulating brain function and behavior in the least invasive manner possible. For the past several years we have explored the potential of utilizing peripheral nerve pathways to tap into brain function. Specifically, we have been focused on developing novel approaches to trigeminal and cervical nerve modulation (FIG. 26). Each of these nerves, as well as other peripheral and cranial nerves offer unique (and overlapping) structural inroads to deep-brain nuclei responsible for regulating psychophysiological arousal, attention, neurobehavioral responses, and physiological performance through ascending and descending circuitry. Based on the evidence we have accumulated from observations in thousands of participants we have strong beliefs that modulation of trigeminal and cervical nerve pathways can offer a chemical-free way of regulating autonomic arousal to improve and optimize mental health and human performance. With continued research and development, there will be some near-term opportunities to offer treatments for some of the most broadly debilitating mental health disorders facing the modern world using transdermal trigeminal and cervical nerve modulation. Attention must be paid to what behavioral paradigms and treatment regimes best support implementation for a specific indication, but the core neurobiological outcomes strongly suggest that treatment of daily stress, anxiety, and comorbid sleep disturbances would be efficient and practical using TEN of the trigeminal and cervical nerves. Likewise, we believe that there will be an opportunity to modulate certain cognitive processes using the same or similar bottom-up modulation approaches via cranial and cervical nerves to induce higher-order plasticity in cortical and subcortical brain regions. For example, pairing of bottom-up NE and ACh modulation using TEN of trigeminal and cervical nerves with top-down cortical processing that occurs during skill training could prove to be a powerful method of accelerating learning or acquiring expert proficiency. Future studies using peripheral nerve modulation to enhance plasticity will directly address this possibility.

FIG. 26 illustrates interfacing with the ascending reticular activating system through the trigeminal sensory nuclear complex. The illustration depicts the approach to modulating trigeminal and cervical nerve afferents, which provide primary sensory inputs to the trigeminal sensory nuclear complex (TSNC). Similar to previously described methods volunteers modulated their trigeminal and cervical nerves using a wearable transdermal neurostimulator for 20 min each night prior to sleep onset. The TSNC coordinates motor behaviors by sending projections through a series of ascending and descending pathways communicating with various targets (greyed out). An emphasis is placed however on the ascending reticular activating system (RAS), which includes the pedunculopontine nucleus (PPN), the locus coeruleus (LC), and raphe nuclei (RN). These pathways transmit neuromodulatory acetylcholine (ACh), norepinephrine (NE), and serotonin (5-HT) signals to higher-order brain structures to gate attention and regulate awareness, arousal, and sleep. As discussed in the text, the TSNC and its inputs have been shown provide functional connections to the LC and PPN and thereby provides a path for the ability of trigeminal and cervical nerve modulation to influence sleep as described in the present study. These pathways also open the possibility of regulating attention, cognition, and sensorimotor behaviors using trigeminal and cervical nerve modulation paired with training or other approaches.

The use of TEN to modulate neural activity is supported by a long history of safety obtained over four decades. There are numerous methods and devices intended for modulating peripheral nerve structures using transcutaneous delivery of voltage/current waveforms from electrodes applied to various locations on the body. These devices such as transcutaneous electrical nerve stimulation (TENS), powered muscle stimulation (PMS), electrical muscle stimulation (EMS) and others have amassed such a high degree of physical safety that they have been moved to an over-the-counter product rather than a medical device requiring a prescription depending on the intended use and design characteristics. For example, legally marketed electrical nerve stimulation devices are already commercially available and have output levels far greater than the ones we implemented here. These devices intended for over-the-counter cosmetic applications of TENS target similar anatomical regions and nerve targets such as the trigeminal nerve. One example is an over-the-counter cosmetic TENS device (Bio-medical Research Face), which is designed to target the trigeminal nerve and provide neuromuscular electrical stimulation (NMES) to encourage facial rejuvenation for aesthetic purposes. A recent study examined the safety and efficacy of this device at a peak current intensity (35 mA) that was nearly twice the one used in our study when used five days per week for 20 minutes each day for 12 weeks. There were no significant adverse events in this study and the only reported side effects were minor skin redness following stimulation, which disappeared with 10-20 minutes following use. Another device, which modulates supraorbital branches of the trigeminal nerve to treat headache has also demonstrated a high safety threshold when used daily for multiple weeks. Other reports using trigeminal nerve stimulation for the treatment of epilepsy, depression, and other disorders have likewise shown a high degree of safety. Although there is a high degree of confidence in the safety of trigeminal nerve modulation, caution is always warranted when delivering electrical currents to the human body and we advise investigators to learn and implement safe practices using qualified devices.

The effects of nightly self-administered TEN on mood and sleep quality in a natural environment We also examined the effects of trigeminal and cervical TEN on sleep quality and mood in healthy volunteers having mild to moderate sleep disturbances (PSQI>5). Various tools and sensors were deployed in real world environments such that data could be acquired from within the homes of volunteers under baseline conditions or following self-administered TEN or sham treatments in a double-blinded fashion depending on the experimental protocol (see Methods). Through a cloud computing architecture, we were able to remotely monitor treatment sessions in order to ensure compliance throughout the study (FIG. 26). We found that one-week of nightly self-administered TEN of trigeminal and cervical afferents (20 min/night) significantly improved mood and sleep quality in home environments. In Experiment 1, we found that one-week of nightly TEN (20 min/night) significantly reduced stress and anxiety compared to baseline DASS scores (FIGS. 19A and 19B). This improvement in mental health indicators was accompanied by a significant reduction in morning drowsiness and significant increase in morning refreshment following TEN of trigeminal and cervical afferents compared to baseline mornings (FIG. 20 and FIGS. 19A and 19B). TEN also caused a significant increase in positive affect and a significant decrease in negative affect according to the PANAS administered on mornings after real treatments compared to sham treatments or baseline nights (FIGS. 20 and 21). In Experiments 2 and 3 we more closely inspected how TEN affected sleep quality using actigraphy. We found that compared to active sham treatment, TEN significantly increased the amount of sleep time and significantly reduced the time awake after sleep onset (WASO; FIGS. 22A, 22B, 24A and 24B). As discussed in more detail below, a low-frequency (0.5-0.75 kHz) shifted TEN waveform (TEN$_{LF}$) caused a significant improvement in sleep quality (FIGS. 25A-25C) compared to the standard high-frequency TEN waveform we used that has been previously described (see Transdermal neuromodulation waveform considerations below). We suspect that the reduction in stress and anxiety, as well as the improved positive affect on weeklong timescales was a secondary outcome of the primary effect that TEN of trigeminal and cervical nerves had on improving sleep quality in a natural or home environment. Future studies examining how TEN of trigeminal and cervical nerves affects sleep structure using polysomnography will inform the design of enhanced approaches to improving general sleep quality, as well as to optimizing the time spent asleep or resting. Such approaches will have a significant impact on our ability to improve daily mental health and restore or enhance human performance.

There is known to be a tight coupling of central nervous system sleep regulation and the activity of the autonomic nervous system where heart-rate control under different stages of sleep in healthy subjects is apparent. During REM sleep heart rate is known to increase. The relative power of the VLF and HF components of the HRV spectra have been shown to be dominant during REM sleep and deep sleep respectively. There is a marked decrease in the relative power of the VLF and LF HRV spectral bands during deep sleep and an increase during REM sleep compared to HF. Since we captured data related to overall sleep quality rather than sleep structure, we cannot draw strong conclusions related to the effects of TEN on HRV as it relates to the stages of sleep. We do conclude however that given the specific changes observed in the HRV power spectra, compared to controls both TEN and TEN$_{LF}$ produce significant alterations to sleep/wake cycling throughout the night. This is somewhat expected given anatomical connectivity and the functional ability of trigeminal nerve and TSNC activity to modulate the activity of the PPN and LC, which are both known to be central regulators of sleep patterns including REM sleep and waking behaviors. More detailed investigations examining sleep structure with additional polysomnography measures will be required to provide further insight into how TEN affects the specific stages of sleep.

TEN methods utilizing pulse frequencies in the 2-20 kHz range may be used. Stimulating neuronal activity in the LC and PPN at specific frequencies can trigger state changes in sleep/wake cycles. Therefore, we questioned whether altering the pulse parameters of high-frequency TEN waveforms would produce different effects on sleep quality or mood. We specifically chose to lower the frequency of the TEN waveforms by about an order of magnitude such that we maintained a neuromodulation frequency above 0.12 kHz. We did this because it had previously been shown that transcutaneous modulation of supraorbital branches of trigeminal nerve afferents at 0.12 kHz induces sedative-like states in humans whereas 0.025 kHz did not. This observation indicated to us that frequencies higher than 0.12 kHz could be even more effective at inducing deep states of relaxation and perhaps, alter sleep quality. Based therefore on our previous observations and those made by Piquet and colleagues (2011) we investigated the effects of low-frequency TEN (TEN$_{LF}$; 0.5-0.75 kHz) waveforms that utilized a base neuromodulation frequency <7 kHz and >0.12 kHz on sleep quality and mood to compare and contrast them to those obtained with high-frequency TEN waveforms. We found that TEN$_{LF}$ caused a significant reduction in the number of nightly wake-ups, a significant reduction in WASO, and a significant reduction in the percentage of time spent awake during the night compared to high-frequency TEN, which itself was significantly effective at improving sleep quality compared to sham and baseline observations (FIGS. 22A, 22B, 24A, 24B, and 25A-25C). Interestingly, the effects of TEN$_{LF}$ on sleep were observed at lower average current amplitudes than those used for standard TEN treatments (see Methods). We also found that TEN$_{LF}$ produced a significant reduction in DASS anxiety scores compared to high-frequency TEN (FIGS. 25A-25C). There was additional biochemical evidence that $TEN_{LF}$ was significantly better at improving restorative sleep than high-frequency TEN.

The protein enzyme α-amylase is as a biochemical marker of noradrenergic activity and sympathoadrenal medullary (SAM) axis activation. Further, it has been shown that α-amylase is a reporter of sleep drive as it increases with accumulating sleep debt. Compared to high-frequency TEN treatments, the waking levels of salivary α-amylase (sAA) were significantly lower following treatment with $TEN_{LF}$ waveforms prior to bed (FIG. 25C). Cortisol is another stress biomarker, which is under the complex control of the hypothalamic-pituitary-adrenal (HPA) axis. Insomnia and sleep debt can lead to adrenal fatigue and significantly dampen the cortisol awakening response (CAR), which specific phase of the diurnal cortisol rhythm. We did find that when participants used $TEN_{LF}$ prior to bed they exhibited a significantly stronger CAR compared to when they used TEN (FIG. 25C). These particular observations indicate that $TEN_{LF}$ produced more robust effects than TEN on the restorative features of sleep by significantly improving the quality of the sleep/wake cycle, as well as altering morning levels of stress biomarkers and sleep debt. In other words, TEN produces a positive impact on mood and sleep quality in a frequency-dependent manner. These observations illustrate the need for systematic research exploring how discrete waveform parameters, such as pulse frequency affect physiological and biochemical responses in humans. Studies in humans can be supported by studies in other animal models where understanding circuit level input-output relationships by conducting electrophysiological recordings from different brain regions is more feasible.

Projections from the TSNC to brain structures like the LC and PPN provide a foundation for the formulation of alternative hypotheses that oppose conventional views on top-down mechanisms of action underlying "transcranial" electrical stimulation (tES) approaches. We believe that noninvasive RAS modulation via the TSNC and other ascending cranial/cervical neural (sensory) pathways offer a solid framework for explaining many of the observations made using the passage of low-intensity direct currents (≤5 mA peak) across the skin and presumably the scalp, dura, and cerebrospinal fluid before influencing the cortical surface (for example, as has been proposed to be a mechanism for transcranial direct current stimulation or tDCS). We cannot imagine a situation where the ascending endogenous neuromodulatory pathways carrying sensory information via cranial nerves do not contribute a significant degree to the observations made using tDCS and some other tES methods. Our studies as well as the studies of many others on electrical neuromodulation or stimulation of cranial nerves indicate that investigators applying electrical currents (DC, AC, or other) to the skin of the head should consider the impact of bottom-up pathways as illustrated in FIG. 26. The possible involvement of bottom-up pathways has been almost entirely overlooked by the scientific community that implements tES. Modulation of afferent pathways via cranial nerves, cervical spinal nerves, and other peripheral systems can explain many if not most of the outcomes observed in studies implementing tES approaches. A simple inspection of neuroanatomy illustrates that cranial nerves carrying afferent signals to the brain stem and RAS structures cannot be avoided when placing electrodes on the head. Further, electrical stimulation of the dura has been shown to activate neurons in the TSNC, which then project to numerous ascending neuromodulatory nuclei.

Highlighting mechanistic inconsistencies regarding tES approaches, explanations underlying the top-down modulation of PFC function using tDCS have led to a high-degree of variability and uncertainty regarding the robustness of behavioral, neurophysiological, and cognitive outcomes. Modulation of the LC activity and noradrenergic signaling, which can be achieved via cranial nerve modulation as previously discussed, has been shown to effect: vigilance and sustained attention, alertness and arousal, working memory and decision making, the amplitude of motor evoked potentials, brain oscillations, sensory gating and processing, and others. These same outcomes have also been claimed via direct modulation of cortical circuits by numerous tES investigations.

Due to spatial and temporal resolution limits it seems that fMRI, EEG, and other neurophysiological or psychological measurements of slowly (hundreds of milliseconds to seconds) evolving biological processes would have difficulty resolving direct cortical effects versus those delayed by transmission at only a couple synapses, which happen to mediate some of the most powerful endogenous neuromodulatory actions upon the human brain. For example, transcranial alternating current stimulation (tACS) of the prefrontal cortex was recently shown to exert an effect on dreaming. It was reported that 25-40 Hz tACS delivered to the prefrontal cortex triggered lucid dreaming and increased conscious self-awareness during dreaming. However trigeminal nerve entrainment of PPN neurons, which as previously mentioned are known to regulate REM sleep at those frequencies, could also explain the effects of tACS on dream (sleep) and conscious self-awareness. Thus to challenge the dogma, we urge the neuromodulation community to explore cranial nerve modulation as an alternative hypothesis capable of mechanistically explaining many of the outcomes observed in response to conventional tES.

The trigeminal nerves may provide a unique opportunity to tap deep into human brain function and may be modulated as described herein. The embedded connectivity of the TSNC with RAS structures like the LC and PPN make trigeminal nerves a high priority peripheral nerve target when using neuromodulation to regulate stress, attention, arousal, and sleep/wake cycles (FIG. 26). TEN of trigeminal and cervical nerves can significantly dampen sympathetic nervous system activity in response to acute stress. Repeated, nightly TEN significantly improves sleep quality and significantly reduces stress and anxiety over the course of a week in healthy volunteers. Transcutaneous trigeminal neurostimulation may be effective at treating drug-resistant epilepsy and depression. Trigeminal neurostimulation may have therapeutic value in managing the symptoms of PTSD, generalized anxiety disorder, and ADHD. Peripheral nerves may induce brain plasticity, and may regulate brain function and behavior through peripheral nerve modulation. Trigeminal and cervical nerve modulation of ascending RAS circuits may be useful for optimizing human performance by regulating states of consciousness, such as sleep/wake cycles, neuro- and psychophysiological arousal, and attention or vigilance.

Methods

All experimental procedures were conducted on human volunteers using protocols approved by an independent Institutional Review Board (Solutions IRB, Little Rock, Ark.). All subjects provided written informed consent prior to experimentation. Exclusion criteria were as follows: diagnosed sleep disorder, actively medicated for sleep difficulties, neurological or psychiatric disorder, cranial or facial metal plate or screw implants, severe face or head trauma, recent concussion or brain injury, recently hospitalized for surgery/illness, high blood pressure, heart disease, diabetes, pregnant, acute eczema on the scalp, and uncorrectable vision or hearing. In Experiment 3, we examined participants with moderate sleep impairment, screened as presenting with a score of 5 or greater on the Pittsburgh Sleep Quality Index. A subset of these participants was selected to provide saliva samples for biometric assays for which several additional exclusion criteria applied: nicotine use, recreational drug use, and dental work during the experimental period. Further, to minimize experimental complexity due to health and due to female hormone fluctuations, which impact the biometric markers being assayed, age range was restricted to 20 to 40 years old and males were oversampled.

Experiment 1 was designed to examine the impact of TEN prior to bedtime on acute and long-term mood, assessed each morning with the Positive and Negative Affectivity Scale (PANAS) and ratings of drowsiness and refreshment, and at the end of each week with the Depression, Anxiety and Stress Scale (DASS). Participants completed a weeklong baseline assessment period followed by a weeklong TEN-treatment period. We enrolled 43 participants, 5 of which were withdrawn for failing to comply with study procedures. Twenty-one participants were men, 17 were women, their ages ranged from 20 to 62 (mean age=29.68±10.88 years), and 67.6% were white, 23.5% were Asian, 2.9% were Black and 5.9% were Hispanic.

Experiment 2 was designed to examine the impact of before bed TEN treatments on sleep patterns and sleep quality, using actigraphy, heart rate monitoring, self-reported number of wake-ups, ratings of sleep quality and the same mood assessment administration as Experiment 1. We enrolled 42 participants, 6 of whom withdrew due to scheduling conflicts and time commitments and 1 that was removed for failing to comply with study procedures. Of these participants, 62.1% were female; their ages ranged from 19 to 59 (mean age=27.66±9.9) and 62.1% were white, 17.2% were Asian, 17.2% were Black and 3.4% were Hispanic.

Experiment 3 was designed to directly compare the impact of bedtime TEN treatments to Sham treatments (active or inactive) on sleep patterns and sleep quality. Experiment 3 employed the same metrics as Experiment 2, with the addition of administration of the DASS during the initial training visit and the PSQI at each visit. In addition, a subset of male participants (N=7) were randomly selected to provide waking, afternoon and before bed saliva samples during the 3 final days of each treatment week. The enrolled sample comprised 27 participants, 2 of which were removed for failing to comply with study procedures or failing to report for scheduled appointments. Ninety-three percent of participants were male, their average age was 32 years old (SD±5.29) and 79% were Caucasian, 11% were Black, 7% were Asian and 4% were Hispanic. As mentioned above, all participants reported active sleep disturbance with PSQI scores ranging from 5 to 15 (mean=9.56±2.55) and 50% of the sample had a score of 9 or below. In addition, participants reported trouble falling asleep or trouble staying asleep at least once or twice a week, with more than 50% of participants on average taking more than 30 minutes to fall asleep each night (mean=34.63±24.02).

The transdermal electrical neuromodulation (TEN) waveform used in these experiments was a pulse-modulated (3-11 kHz), biphasic electrical current producing average amplitudes of 5-7 mA for 20 min as similarly described in above. The sham waveform was an active stimulation control, in which the waveform parameters outlined above were active for only the first and last 30 secs of the 20 min treatment, providing a significantly lower dosage of the TEN treatment and offering skin sensations that mimicked real treatment. Participants were not able to distinguish between real TEN and sham waveforms. In a subset of participants in Experiment 3, the real TEN waveform described above was compared to a lower-frequency TEN waveform (TEN$_{LF}$; pulse frequency 0.50-0.75 kHz, <5 mA average amplitude), which in lab tests produced more pronounced changes on autonomic nervous system balance (FIG. 27). During both the real TEN and sham stimulus protocols, subjects were instructed to adjust the current output of a wearable TEN device (Thync, Inc., Los Gatos, Calif.) using an iPod touch connected to the device over a Bluetooth low energy network such that it was comfortable. TEN and sham waveforms were delivered to the right temple (10/20 site F8) and base of the neck (5 cm below the inion) using custom-designed electrodes comprising a hydrogel material and a conductive Ag/AgCl film secured to the wearable TEN device. The anterior electrode positioned over F8 was a 4.9 cm$^2$ oval having a major axis of 2.75 cm and a minor axis of 2.25 cm while the posterior electrode was a 12.5 cm$^2$ rectangle with a length of 5 cm and a height of 2.5 cm. The average current density was <2 mA/cm$^2$ at all times to keep in accordance with general safety practices to prevent any damage to the skin. Across all experiments, participants were trained to use the TEN device on their first visit and were instructed to use within 30 min prior to bed. In Experiments 2 and 3, subjects were assigned to experimental conditions using a randomization method or a counterbalancing approach, and subjects and researchers were always kept blind to experimental conditions.

We utilized several scales and schedules to evaluate the impact of TEN on mood and sleep quality. The self-reported scales used in the present study are described below. The Awakening Drowsiness and Refreshment scale was a 5-item self-report measure that is administered in the mornings, within a half hour of waking, to assess feelings of awakening drowsiness (tired and lethargic) and refreshment (refreshed, alert and clear-headed). Items were rated on a 1—low to 10—high scale. Across baseline and TEN treatment periods for Experiments 1 and 2 internal consistencies ranged from 0.72 to 0.83 for drowsiness and 0.72 to 0.89 for refreshed. The Positive Affect and Negative Affect Schedule (PANAS) is a clinically validated scale that comprises two 10-item scales: positive affectivity and negative affectivity. Participants rate "how they feel right now" on a 5 point scale: 1—very slightly/not at all to 5—extremely. Across all phases of experiments 1 and 2 internal consistencies ranged from 0.94 to 0.96 for positive affectivity and 0.65 to 0.93 for negative affectivity. The Karolinska Sleep Diary (KSD) is a self-report questionnaire administered in the mornings that captures information about the prior nights sleep (e.g., time in bed, time asleep, number of wake-ups, and ratings of degree of dreaming, calm sleep, and sleep quality). This questionnaire has been validated against polysomnography and is correlated with objective EEG sleep metrics (for example, the amount of slow-wave sleep and sleep efficiency). The Depression, Anxiety, Stress Scale (DASS) is a reliable clinically validated self-report measure that comprises 42 negative emotional symptoms. Each item is rated on a 4-point severity/frequency scale and indexed to the past week. Scores for the Depression, Anxiety and Stress scales are determined by summing the scores for the relevant 14 items. Reliabilities on the subscales ranged from 0.53 to 0.95 across all baseline and treatment weeks for all experiments. The Pittsburgh Sleep Quality Index (PSQI) is a 20-item assessment that gauges overall sleep patterns over the past month, including duration of sleep, type of sleep disturbance, sleep latency, sleep efficiency, overall sleep quality, and day dysfunction due to sleepiness. The PSQI was administered in Experiment 3. The baseline administration was indexed to the past month, and subsequent assessments were indexed to past week, capturing sleep changes due to TEN or sham treatment. Scores for the PSQI were calculated according the algorithm outlined by Buysse and colleagues (1989).

In Experiments 2 and 3, to monitor sleep/wake cycles, participants wore the clinically validated Phillips Respironics Actiwatch 2 (Phillips Healthcare) on their non-dominant wrist throughout the course of the study. The Actiwatch 2 was equipped with solid-state piezoelectric accelerometer to capture actigraph data at 32 Hz and event markers were used to capture bedtime and morning waking. The Actiwatch 2 has been shown to reliably tracks sleep/wake cycles and calculates duration, wake after sleep onset (WASO), sleep time, wake time, number of wake-ups, and percent sleep/wake.

In Experiments 2 and 3, we acquired cardiac output using the Polar H7 heart rate monitor. Recordings started immediately prior to bed, after sham/TEN use, and were terminated upon waking. During participants first office visit they were trained according to manufacturers instructions on preparation and usage of the device. Electrocardiogram (ECG) data were live streamed to the HRV Logger application, which converted the ECG to R-R data that was exported daily to secure servers. We had previously confirmed that HRV Logger recorded data accurately using independent HRV analyses conducted with Kubios and Matlab. We computed an average nightly HR, R-R interval, standard deviation of the normal-to-normal heartbeat (SDNN), and root mean square of the standard deviation (RMSSD). Nightly R-R data were transformed into frequency domain data to examine the relative power of the very low-frequency (pVLF; 0.0033-0.04 Hz), low-frequency (pLF; 0.04-0.15 Hz) and high-frequency (pHF; 0.15-0.4 Hz) bands of the HRV spectra, including peak low frequency (pkLF), peak high frequency (pkHF) and the LF/HF ratio.

In Experiment 3, participants provided awakening, afternoon and bedtime saliva samples Tuesday, Wednesday and Thursday of each week of the study. Participants were instructed not to eat or brush their teeth within an hour of providing a sample. Timing of saliva collection varied across participants, but participants provided samples at the same times each day. All morning samples were taken immediately upon waking since this has been shown to reduce variability in assaying the cortisol awakening response. Afternoon saliva samples were taken between 3 PM and 5 PM, and bedtime samples were taken within 30 minutes before bed, which was just prior to TES usage. Salvia was collected via that passive drool method. As per manufacturers instructions (SalivaBio, Inc., State College, Pa.), saliva is pooled at the front of the mouth and eased through a tube, centered on the lips, directly into a cryovial. Saliva samples were immediately stored at −20° C. and were transported back to the testing facility on ice, from there saliva samples were sent to Salimetrics, LLC (State College, Pa.) where ELISA methods were employed to assess α-amylase (Salimetrics 1-1902) and cortisol levels (Salimetrics 3002). Salivary α-amylase is a biomarker for sleep in humans and is widely recognized as a biochemical marker of sympathetic nervous system activity and sympathoadrenal medullary (SAM) axis activation. The glucocorticoid hormone cortisol has a diurnal rhythm, which peaks within 45 of waking. The cortisol awakening response (CAR) is sensitive to sleep disturbances where poor sleep correlates with a blunted CAR.

Given the quick but steep learning curve with fitting the device and given that during training sessions participants received a TEN treatment, we excluded the first baseline and TEN-treatment day from all analyses in Experiments 1 and 2. All statistical analyses were completed with IBM SPSS Statistics Software (IBM Corporation, Armonk, N.Y.). In Experiments 1 and 2, unless otherwise stated, all statistical analyses were conducted using paired sample t-tests. In Experiment 3, order effects were examined using two-way repeated measures analyses of variance (RMANOVA). All tests were not significant and were followed by a series of one-way RMANOVA. Across all studies, metrics that were assessed daily were averaged separately across the each assessment period (baseline/TEN/Sham). Participants with fewer than 3 days of data on any metric for any phase of an experiment were considered to have incomplete data on the given metric. Missing or incomplete data were deleted listwise. Thresholds for statistical significance were set at $p<0.05$. All data reported and shown are mean±SD.

In general, any of the apparatuses described herein (e.g., within the processor of the neurostimulator) may include firmware and communication protocols for receiving and responding to the command messages. Any of the processors (neurostimulators) described herein may also be configured to transmit error codes back to the controller. For example, the processor may, during communication (e.g., via a communication circuit) check whether received waveform parameters comply with limitations of hardware and safety standards. Examples of error codes that may be safety conditions (e.g., current requested too high, electrode contact lost or poor connection, DC limit reached, communication lost), error codes related to the received command messages/communication (e.g., too many wave segments, fewer segments received than expected, received segments too short, received segments too long, etc.)

Any of the apparatuses for neurostimulation described herein may be configured to receive a plurality of neurostimulation command messages, including in particular the new waveform message and subsequent segment messages, which may include parameters from a controller such as a computing device (e.g., smartphone, etc.) and apply them as stimulation. The neurostimulator may also adjust them and/or send one or more response error messages back to the controller if the parameters contained in the messages do not comply with hardware limitations and/or safety limits which may be included in the neurostimulator.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of non-invasively reducing sleep onset and increasing sleep duration, the method comprising:
attaching a first electrode to a subject's head or neck at a first location and a second electrode to the subject's head or neck at a second location, wherein the first and the second electrode are coupled to a transdermal electrical stimulation (TES) applicator worn by the subject;

applying a sleep inducing ensemble waveform characterized by an electrical stimulation between the first and second electrodes, wherein the electrical stimulation has a peak amplitude of greater than 3 mA, a frequency of greater than 250 Hz, and a duty cycle of greater than 10%; and continuing application of the electrical stimulation for a stimulation duration of at least one minute to enhance sleepiness, sustain sleep or to enhance sleepiness and sustain sleep.

2. The method of claim 1, wherein attaching comprises adhesively attaching.

3. The method of claim 1, wherein attaching comprises attaching the first electrode to the subject's temple region.

4. The method of claim 1, wherein attaching comprises attaching the second electrode to the subject's neck above the subject's vertebra prominens.

5. The method of claim 1, further comprising allowing the subject to select a set of parameters for the electrical stimulation to be applied, wherein the set of parameters includes one or more of: stimulation duration, frequency, peak amplitude, and duty cycle.

6. The method of claim 1, further comprising wearing the electrodes while the subject sleeps.

7. The method of claim 1, further comprising removing the first and second electrodes and TES applicator prior to the subject sleeping.

8. The method of claim 1, wherein applying comprises applying a biphasic electrical stimulation.

9. The method of claim 1, wherein applying comprises applying a biphasic electrical stimulation and further wherein the biphasic electrical stimulation is asymmetric with respect to positive and negative going phases.

10. The method of claim 1, wherein applying comprises applying the electrical stimulation having a duty cycle of between 10% and 90%.

11. The method of claim 1, wherein applying comprises applying the electrical stimulation having a duty cycle of between 30% and 60%.

12. The method of claim 1, wherein applying comprises applying the electrical stimulation having a peak amplitude of 5 mA or greater.

13. The method of claim 1, wherein applying comprises applying the electrical stimulation having a frequency of greater than 500 Hz.

14. The method of claim 1, wherein applying comprises applying the electrical stimulation having a frequency of greater than 750 Hz.

15. The method of claim 1, wherein applying comprises applying the electrical stimulation having a frequency of greater than 5 kHz.

16. The method of claim 1, wherein continuing application of the electrical stimulation for a stimulation duration comprises continuing for a stimulation duration of at least five minutes.

17. The method of claim 1, wherein applying comprises applying the electrical stimulation having amplitude modulation.

18. The method of claim 1, wherein applying comprises applying the electrical stimulation having amplitude modulation, and further wherein the amplitude modulation has a frequency of less than 250 Hz.

19. The method of claim 1, wherein applying comprises applying the electrical stimulation having a burst mode.

20. The method of claim 1, wherein the first location is on the subject's head and the second location is on the subject's neck.

21. A wearable transdermal electrical stimulation (TES) applicator for facilitating, inducing, and/or maintaining sleep in a subject, the device comprising:
a body;
a first electrode;
a second electrode; and
a TES control module at least partially within the body and comprising a processor, a timer and a waveform generator, wherein the TES control module is adapted to deliver a sleep inducing ensemble waveform characterized by a transdermal biphasic electrical stimulation signal of 10 seconds or longer between the first and second electrodes having a duty cycle of greater than 10 percent, a frequency of 250 Hz or greater, and an intensity of 3 mA or greater, wherein the biphasic transdermal electrical stimulation is asymmetric with respect to positive and negative going phases;
wherein the wearable TES applicator weighs less than 50 grams; and
at least one sensor configured to be coupled to the body for sleep monitoring of the subject.

22. The device of claim 21, wherein the duty cycle is between 30% and 60%.

23. The device of claim 21, wherein the transdermal electrical stimulation has a frequency greater than 750 Hz.

24. The device of claim 21, wherein the transdermal electrical stimulation has a frequency greater than 5 kHz.

25. The device of claim 21, wherein the transdermal electrical stimulation comprises amplitude modulation.

26. The device of claim 21, wherein the transdermal electrical stimulation comprises amplitude modulation and wherein the amplitude modulation has a frequency of less than 250 Hz.

27. The device of claim 21, wherein the transdermal electrical stimulation comprises a burst mode.

28. The device of claim 21, wherein the transdermal electrical stimulation comprises a burst mode and wherein the frequency of bursting is less than 250 Hz.

29. The device of claim 21 wherein the at least one sensor is configured to measure the subject's autonomic function.

30. The device of claim 21 wherein the at least one sensor is configured to measure the subject's autonomic function, further wherein the measurement of autonomic function measures one or more of: galvanic skin resistance, heart rate, heart rate variability, or breathing rate.

31. The device of claim 21 wherein the at least one sensor comprises a sensor to detect the subject's movements.

32. A method for improving sleep comprising delivering a sleep inducing ensemble waveform characterized by transdermal electrical stimulation of a subject's peripheral nerves of the head and neck and inducing a change in cognitive state that improves sleep and mood in the subject, wherein the transdermal electrical stimulation is 10 seconds or longer, has a duty cycle of greater than 10 percent, a frequency of 250 Hz or greater, and an intensity of 3 mA or greater, wherein the transdermal electrical stimulation is asymmetric with respect to positive and negative going phases.

* * * * *